US008466154B2

(12) United States Patent
Fernandez et al.

(10) Patent No.: US 8,466,154 B2
(45) Date of Patent: Jun. 18, 2013

(54) METHODS AND COMPOSITIONS RELATED TO WRAPPING OF DEHYDRONS

(75) Inventors: Ariel Fernandez, Houston, TX (US); William Bornmann, Missouri City, TX (US); Gabriel Lopez-Berestein, Bellaire, TX (US); Angela Sanguino, Pittsburgh, PA (US); Zheng-Hong Peng, Missouri City, TX (US); Anil K. Sood, Pearland, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 1632 days.

(21) Appl. No.: 11/927,329

(22) Filed: Oct. 29, 2007

(65) Prior Publication Data

US 2013/0131076 A1    May 23, 2013

Related U.S. Application Data

(60) Provisional application No. 60/863,255, filed on Oct. 27, 2006.

(51) Int. Cl.
*A61K 31/496*    (2006.01)
*C07D 403/14*    (2006.01)

(52) U.S. Cl.
USPC ..................... 514/252.11; 544/295

(58) Field of Classification Search
USPC ..................... 514/252.11; 544/295
See application file for complete search history.

(56) References Cited

U.S. PATENT DOCUMENTS

| | | | | |
|---|---|---|---|---|
| 4,623,486 | A | 11/1986 | Lombardino | 514/217.05 |
| 5,399,363 | A | 3/1995 | Liversidge et al. | 424/490 |
| 5,459,127 | A * | 10/1995 | Felgner et al. | 424/450 |
| 5,521,184 | A | 5/1996 | Zimmermann | 514/252 |
| 5,543,158 | A | 8/1996 | Gref et al. | 424/501 |
| 5,580,579 | A | 12/1996 | Ruddy et al. | 424/489 |
| 5,641,515 | A | 6/1997 | Ramtoola | 424/489 |
| 5,792,451 | A | 8/1998 | Sarubbi et al. | 424/85.4 |
| 5,885,613 | A | 3/1999 | Holland et al. | 424/450 |
| 6,114,333 | A | 9/2000 | Davis et al. | 514/252.18 |
| 6,710,048 | B2 | 3/2004 | Kuo et al. | 514/252.11 |
| 6,894,051 | B1 | 5/2005 | Zimmermann et al. | 514/252.18 |
| 7,910,586 | B2 * | 3/2011 | Netzer et al. | 514/247 |
| 2004/0248918 | A1 | 12/2004 | Kim et al. | 514/275 |
| 2010/0249122 | A1 * | 9/2010 | Kalman | 514/230.5 |

FOREIGN PATENT DOCUMENTS

| | | |
|---|---|---|
| WO | WO 03/027100 | 4/2003 |
| WO | WO 2004/108699 | 12/2004 |
| WO | WO 2006/108405 | 10/2006 |
| WO | WO 2006/133046 | 12/2006 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Grant & Hackh's Chemical Dictionary (5th ed. 1987) (p. 542).*
Byrn et al., Solid-State Chemistry of Drugs (2nd Ed. 1999) (pp. 233-247, 234).*
Golub et al. Science (1999), vol. 286 531-537.*
Lala et al. Cancer and Metastasis Reviews (1998), 17(1), 91-106.*
Béni et al., "Molecular interactions in imatinib-DPPC liposomes," *European Journal of Pharmaceutical Sciences*, 27:205-211, 2006.
Capdeville et al., "Glivec (STI571, imatinib), a rationally developed targeted anticancer drug," *Nature Reviews Drug Discovery*, 1:493-502, 2002.
Chen et al., "Molecular basis for specificity in the druggable kinome: sequence-based analysis," *Bioinformatics*, 23:563-572, 2007.
Crespo and Fernández, "Kinase packing defects as drug targets," *Drug Discovery Today*, 12:917-923, 2007.
Deremble and Lavery, "Macromolecular recognition," *Curr. Opin. Struc. Biol.*, 15:171-75, 2005.
Donato and Talpaz, "Clinical use of tyrosine kinase inhibitors: therapy for chronic myelogenous leukemia and other cancers," *Clin. Cancer Res.*, 6:2965-66, 2000.
Fabian et al., "A small molecule-kinase interaction map for clinical kinase inhibitors," *Nature Biotechnology*, 23:329-336, 2005.
Faderl et al., "The biology of chronic myeloid leukemia," *N. Engl. J. Med.*, 341:164-172, 1999.
Fernández and Berry, "Molecular dimension explored in evolution to promote proteomic complexity," *Proc. Natl. Acad. Sci. USA*, 101:13460-13465, 2004.
Fernández and Scheraga, "Insufficiently dehydrated hydrogen bonds as determinants of protein interactions," *Proc. Natl. Acad. Sci. USA*, 100:113-118, 2003.
Fernández and Scott, "Adherence of packing defects in soluble proteins," *Phys. Rev. Lett.*, 91:018102, 2003.
Fernández and Scott, "Dehydron: a structurally encoded signal for protein interaction," *Biophys. J.*, 85:1914-1928, 2003.
Fernández et al., "An anticancer C-kit kinase inhibitor is re-engineered to make it more active and less cardiotoxic," *J. Clin. Invest.*, 117:4044-4054, 2007.
Fernández et al., "Inhibitor design by wrapping packing defects in HIV-1 proteins," *Proc. Natl. Acad. Sci. USA*, 101:11640-11645, 2004.
Fernández et al., "Packing defects as selectivity switches for drug-based protein inhibitors," *PNAS*, 103:323-328, 2006.
Fernández et al., "Rational drug redesign to overcome drug resistance in cancer therapy: imatinib moving target," *Cancer Research*, 67:4028-4033, 2007.

(Continued)

*Primary Examiner* — Samantha Shterengarts
(74) *Attorney, Agent, or Firm* — Parker Highlander PLLC

(57) ABSTRACT

This application describes a novel technology in drug discovery and drug-based imaging/detection: the wrapping technology. This technology is based on identified singularities in the structure of soluble proteins. In contrast with drug-design approaches based on standard structural considerations, the packing of a protein, or more precisely, its dehydron pattern, may be used as a selectivity filter to design small-molecule inhibitors. The wrapping technology described herein is a novel form of rational drug design for avoiding side effects in drug therapy and sharpening the inhibitory impact of drugs on the oncokinome.

20 Claims, 16 Drawing Sheets

OTHER PUBLICATIONS

Fernández, "Incomplete protein packing as a selectivity filter in drug design," *Structure*, 13:1829-1836, 2005.
Fernández, "Keeping dry and crossing membranes," *Nature Biotechnol.*, 22:1081-1084, 2004.
Kellenberger et al., "Comparative evaluation of eight docking tools for docking and virtual screening accuracy," *Proteins*, 57:225, 2004.
Ma et al., "Protein-protein interactions: structurally conserved residues distinguish between binding sites and exposed protein surfaces," *Proc. Natl. Acad. Sci. USA*, 100:5772-5777, 2003.
International Search Report and Written Opinion, issued in Application No. PCT/US2007/082893, dated Oct. 6, 2008.
Ramsay et al., "The formulation of lipid-based nanotechnologies for the delivery of fixed dose anticancer drug combinations," Database accession No. EMB-2005408894 abstract, 2005.
Schindler et al., "Structural mechanism for STI-571 inhibition of abelson tyrosine kinase," *Science*, 289:1938-1942, 2000.
Tanis et al., "Synthesis and biological activity of metabolites of the antidiabetic, antihyperglycemic agent pioglitazone," *J. Med. Chem.*, 39:5053-5063, 1996.
Wang and Wang, "How does consensus scoring work for virtual library screening? An idealized computer experiment," *J. Chem. Inf. Comput. Sci.*, 41:1422, 2001.
Zimmerman et al., "Potent and selective inhibitors of the abl-kinase: phenylamino-pyrimidine (PAP) derivatives," *Bioorganic & Medicinal Chemistry Letters*, 7:187-192, 1997.
Zhang et al., "Turning promiscuous kinase inhibitors into safer drugs," *Trends in Biotech.*, in press, 2008.

* cited by examiner

SEQUENCE LISTING

```
<160> NUMBER OF SEQ ID NOS: 11

<210> SEQ ID NO 1
<211> LENGTH: 16
<212> TYPE: PRT
<213> ORGANISM: Artificial
<220> FEATURE:
<223> OTHER INFORMATION: Synthetic peptide

<400> SEQUENCE: 1

Ala Glu Glu Glu Ile Tyr Gly Glu Phe Glu Ala Lys Lys Lys Lys Gly
1               5                   10                  15

<210> SEQ ID NO 2
<211> LENGTH: 21
<212> TYPE: PRT
<213> ORGANISM: Artificial
<220> FEATURE:
<223> OTHER INFORMATION: Synthetic peptide

<400> SEQUENCE: 2

Lys Val Val Glu Glu Ile Asn Gly Asn Asn Tyr Val Tyr Ile Asp Pro
1               5                   10                  15

Thr Gln Leu Pro Tyr
            20

<210> SEQ ID NO 3
<211> LENGTH: 21
<212> TYPE: PRT
<213> ORGANISM: Artificial
<220> FEATURE:
<223> OTHER INFORMATION: Synthetic peptide

<400> SEQUENCE: 3

Gly Leu Ala Arg Leu Ile Glu Asp Asn Glu Tyr Thr Ala Arg Glu Gly
1               5                   10                  15

Ala Lys Phe Pro Ile
            20

<210> SEQ ID NO 4
<211> LENGTH: 21
<212> TYPE: PRT
<213> ORGANISM: Artificial
<220> FEATURE:
<223> OTHER INFORMATION: Synthetic peptide

<400> SEQUENCE: 4

Gly Cys Ser Pro Ala Leu Lys Arg Ser His Ser Asp Ser Leu Asp His
1               5                   10                  15

Asp Ile Phe Gln Leu
            20

<210> SEQ ID NO 5
<211> LENGTH: 21
```

```
<212> TYPE: PRT
<213> ORGANISM: Artificial
<220> FEATURE:
<223> OTHER INFORMATION: Synthetic peptide

<400> SEQUENCE: 5

Glu Gly Leu Gly Pro Gly Asp Thr Thr Ser Thr Phe Cys Gly Thr Pro
1               5                   10                  15

Asn Tyr Ile Ala Pro
            20

<210> SEQ ID NO 6
<211> LENGTH: 15
<212> TYPE: PRT
<213> ORGANISM: Artificial
<220> FEATURE:
<223> OTHER INFORMATION: Synthetic peptide

<400> SEQUENCE: 6

Lys Val Glu Lys Ile Gly Glu Gly Thr Tyr Gly Val Val Tyr Lys
1               5                   10                  15

<210> SEQ ID NO 7
<211> LENGTH: 7
<212> TYPE: PRT
<213> ORGANISM: Artificial
<220> FEATURE:
<223> OTHER INFORMATION: Synthetic peptide

<400> SEQUENCE: 7

His His Ala Ser Pro Arg Lys
1               5

<210> SEQ ID NO 8
<211> LENGTH: 20
<212> TYPE: DNA
<213> ORGANISM: Artificial
<220> FEATURE:
<223> OTHER INFORMATION: Synthetic primer

<400> SEQUENCE: 8
agctgctgga gctgataaga                                              20

<210> SEQ ID NO 9
<211> LENGTH: 20
<212> TYPE: DNA
<213> ORGANISM: Artificial
<220> FEATURE:
<223> OTHER INFORMATION: Synthetic primer

<400> SEQUENCE: 9
ttacagccca aacgactgac                                              20

<210> SEQ ID NO 10
<211> LENGTH: 26
<212> TYPE: DNA
<213> ORGANISM: Artificial
<220> FEATURE:
<223> OTHER INFORMATION: Synthetic primer

<400> SEQUENCE: 10
atctggcacc acaccttcta caatga                                       26

<210> SEQ ID NO 11
<211> LENGTH: 26
<212> TYPE: DNA
<213> ORGANISM: Artificial
```

```
<220> FEATURE:
<223> OTHER INFORMATION: Synthetic primer

<400> SEQUENCE: 11
cgtcatactc ctgcttgctg atccac                                           26
```

METHODS AND COMPOSITIONS RELATED TO WRAPPING OF DEHYDRONS

This application claims priority to U.S. Provisional Patent application Ser. No. 60/863,255 filed Oct. 27, 2006, which is incorporated herein by reference in its entirety.

This invention was made with government support under R01 GM072614-01 awarded by National Institutes of Health. The government has certain rights in the invention.

BACKGROUND OF THE INVENTION

I. Field of the Invention

The present invention relates to the general fields of biochemistry, oncology, computational bioengineering/bioinformatics, structural biology/molecular biophysics, medicinal chemistry, pharmacology, X-ray crystallography, cellular biology, and/or molecular imaging. More particularly, the compositions and methods of the invention relate to the optimization of various parental drugs and the design of a wrapping optimized drug ("wrapper compound") using complementation of packing defects in a drug target.

II. Background

Molecularly targeted therapy and diagnosis are powerful tools in the fight against cancer. In this regard, signal-transducing molecules, the kinases, have become quintessential drug targets. However, the evolutionary relatedness of kinases makes most inhibitory drugs cross reactive, with a high likelihood of off-target associations, yielding highly uncertain and often dangerous results. The most alarming aspect of such treatments is the actual unpredictability in the extent of specificity, including the associated health-related risks and side-effect complications.

Ligand cross reactivity, amply illustrated by drug-based kinase inhibition, has been identified as a major cause of side effects and of misleading or ambiguous diagnosis. Additional methods are needed that use molecular design to modulate cross reactivity within the oncokinome to sharpen the specificity of a new generation of drugs on clinically relevant targets for therapeutic and imaging purposes. (A kinome is a subset of the genome consisting of the protein kinase genes and an oncokinome is a subset of kinome that is associated with or related to cancers.) This is a challenging problem since the extent of structural conservation of kinases, especially at the primary (ATP-) binding sites, is staggering. The starting point is the observation that there is a molecular marker for ligand specificity so far overlooked, i.e., the packing defects that are not conserved across evolutionary related proteins (Fernandez and Berry, 2004). Packing defects are functionally critical because they are indicators of protein interactivity, or markers for protein-ligand association (Fernandez and Scheraga, 2003; Fernandez, 2004) and constitute a decisive factor in macromolecular recognition (Ma et al., 2003; Deremble and Lavery, 2005). These defects consist of intramolecular hydrogen bonds incompletely packed, or poorly protected from water attack. They are termed dehydrons (Fernandez, 2004; Fernandez and Scott, 2003 a,b), because they promote their own dehydration as a means to strengthen and stabilize the electrostatic interaction. Dehydrons may be identified from protein structure by quantifying the extent of intramolecular desolvation of the hydrogen bonds. This parameter indicates the number of "wrapping" nonpolar groups within a microenvironment around the hydrogen bond. Thus, there is a need to engineer drugs that "wrap" packing defects that are not conserved across paralogs.

Thus, additional compositions and methods are needed to solve this critical biomedical problem and create a translational platform to promote target specificity in drug development and drug-based imaging diagnosis.

SUMMARY OF THE INVENTION

This application describes compounds designed using a novel technology in drug discovery and drug-based imaging/detection, i.e., the wrapping technology. This technology is based on identified singularities in the structure of soluble proteins. In contrast with drug-design approaches based on standard structural considerations, the packing of a protein, or more precisely, its dehydron pattern, may be used as a selectivity filter to design small-molecule inhibitors. The wrapping technology described herein is a novel form of rational design for avoiding side effects in drug therapy and sharpening the inhibitory impact of drugs on the oncokinome.

Embodiments of the invention are based on packing or wrapping defect not conserved across related proteins. Thus, the inventors introduce an additional technology, the wrapping technology, to target packing defects and turn molecular prototypes into therapeutic and diagnostic tools.

Embodiments of the invention include a protein ligand engineered by the methods described herein. A protein ligand of the invention can bind and inhibit the activity of an enzyme, such as a kinase, and/or the interactivity of a protein, such as a cell surface receptor.

Embodiments of the invention include protein ligand having following chemical formula:

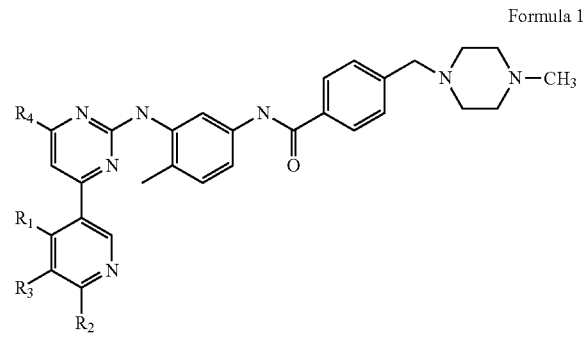

Formula 1

R1 may include one or more of, or exclude one or more of hydrogen, alkyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl.

R2 may include one or more of, or exclude one or more of hydrogen, alkyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl.

R3 may include one or more of, or exclude one or more of hydrogen, alkyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl.

R4 may include one or more of, or exclude one or more of hydrogen, alkyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl.

As used herein, the term "aliphatic linker" or "aliphatic group" is a non-aromatic, consisting solely of carbon and hydrogen and may optionally contain one or more units of saturation, e.g., double and/or triple bonds (also refer herein as "alkenyl" and "alkynyl," respectively). An aliphatic or aliphatic group may be straight chained, branched (also refer herein as "alkyl") or cyclic (also refer herein as "cycloalkyl). When straight chained or branched, an aliphatic group typically contains between about 1 and about 10 carbon atoms, more typically between about 1 and about 6 carbon atoms. When cyclic, an aliphatic typically contains between about 3 and about 10 carbon atoms, more typically between about 3 and about 7 carbon atoms. Aliphatics are preferably $C_1$-$C_{10}$ straight chained or branched alkyl groups (i.e., completely saturated aliphatic groups), more preferably $C_1$-$C_6$ straight chained or branched alkyl groups. Examples include, but are not limited to methyl, ethyl, propyl, n-propyl, iso-propyl, n-butyl, sec-butyl, and tert-butyl. Additional examples include, but are not limited to, cyclopropyl, cyclopentyl, cyclohexyl, cyclopentyl, cyclohexylyl and the like.

The term "alkyl," unless otherwise indicated, refers to those alkyl groups of a designated number of carbon atoms of either a straight or branched saturated configuration. As used herein, "$C_0$ alkyl" means that there is no carbon and therefore represents a bond. Examples of "alkyl" include, but are not limited to, methyl, ethyl, n-propyl, isopropyl, n-butyl, isobutyl, sec-butyl and tert-butyl, pentyl, hexyl, isopentyl and the like. Alkyl as defined above may be optionally substituted with a designated number of substituents as set forth in the embodiment recited above. As used herein, the term "alkyloxo" means an alkyl group of the designated number of carbon atoms with a "=O" substituent.

The term "alkenyl" means hydrocarbon chain of a specified number of carbon atoms of either a straight or branched configuration and having at least one carbon-carbon double bond, which may occur at any point along the chain, such as ethenyl, propenyl, butenyl, pentenyl, vinyl, alkyl, 2-butenyl and the like. Alkenyl as defined above may be optionally substituted with designated number of substituents as set forth in the embodiment recited above.

The term "alkynyl" means hydrocarbon chain of a specified number of carbon atoms of either a straight or branched configuration and having at least one carbon-carbon triple bond, which may occur at any point along the chain. Example of alkynyl is acetylene. Alkynyl as defined above may be optionally substituted with designated number of substituents as set forth in the embodiment recited above.

The term "heteroalkyl" refers to a hydrocarbon chain of a specified number of carbon atoms wherein at least one carbon is replaced by a heteroatom selected from the group consisting of O, N and S.

The term "cycloalkyl" refers to a saturated or partially saturated carbocycle containing one or more rings of from 3 to 12 carbon atoms, typically 3 to 7 carbon atoms. Examples of cycloalkyl includes, but are not limited to cyclopropyl, cyclobutyl, cyclopentyl, cyclohexyl, and cycloheptyl, and the like. "Cycloalkyaryl" means that an aryl is fused with a cycloalkyl, and "Cycloalkylaryl-alkyl" means that the cycloalkylaryl is linked to the parent molecule through the alkyl. Cycloalkyl as defined above may be optionally substituted with a designated number of substituents as set forth in the embodiment recited above.

The term "halo" refers to fluoro, chloro, bromo and iodo.

The term "haloalkyl" is a $C_1$-$C_6$ alkyl group, which is substituted with one or more halo atoms selected from F, Br, Cl and I. An example of a haloalkyl group is trifluoromethyl ($CF_3$).

The term "alkoxy" and "alkyloxy" represents an alkyl group of indicated number of carbon atoms attached through an oxygen bridge, such as methoxy, ethoxy, propoxy, isopropoxy, butoxy, tert-butoxy, pentoxy, and the like. Alkoxy as defined above may be optionally substituted with a designated number of substituents as set forth in the embodiment recited above.

The term "haloalkyloxy" represents a $C_1$-$C_6$ haloalkyl group attached through an oxygen bridge, such as $OCF_3$. The "haloalkyloxy" as defined above may be optionally substituted with a designated number of substituents as set forth in the embodiment recited above.

The term "oxo" means a group of the formula: "=O". The term "sulfo" means a group of the formula "=S".

The term "aryl" includes carbocyclic aromatic ring systems (e.g., phenyl), fused polycyclic aromatic ring systems (e.g., naphthyl and anthracenyl) and aromatic ring systems fused to carbocyclic non-aromatic ring systems (e.g., 1,2,3,4-tetrahydronaphthyl). "Aryl" as defined above may be optionally substituted with a designated number of substituents as set forth in the embodiment recited above.

As used herein, the term "fused phenyl" means that the phenyl ring is fused with the group to form a bicyclic group of the formula and wherein such group is substituted, as defined herein.

The term "arylalkyl" refers to an aryl alkyl group which is linked to the parent molecule through the alkyl group, which may be further optionally substituted with a designated number of substituents as set forth in the embodiment recited above. When arylalkyl is aryl $C_0$ alkyl, then the aryl group is bonded directly to the parent molecule. Likewise, arylheteroalkyl means an aryl group linked to the parent molecule through the heteroalkyl group.

The term "acyl" refers to alkylcarbonyl species.

The term "heteroaryl" group, as used herein, is an aromatic ring system having at least one heteroatom such as nitrogen, sulfur or oxygen and includes monocyclic, bicyclic or tricyclic aromatic ring of 5- to 14-carbon atoms containing one or more heteroatoms selected from the group consisting of O, N, and S. The "heteroaryl" as defined above may be optionally substituted with a designated number of substituents as set forth in the embodiment recited above. Examples of heteroaryl are, but are not limited to, furanyl, indolyl, thienyl (also referred to herein as "thiophenyl") thiazolyl, imidazolyl, isoxazoyl, oxazoyl, pyrazoyl, pyrrolyl, pyrazinyl, pyridyl, pyrimidyl, pyrimidinyl and purinyl, cinnolinyl, benzofuranyl, benzothienyl, benzotriazolyl, benzoxazolyl, quinoline, isoxazolyl, isoquinoline and the like. The term "heteroarylalkyl" means that the heteroaryl group is linked to the parent molecule through the alkyl portion of the heteroarylalkyl.

The term "heterocycloalkyl" refers to a non-aromatic ring which contains one or more oxygen, nitrogen or sulfur and includes a monocyclic, bicyclic or tricyclic non-aromatic ring of 5 to 14 carbon atoms containing one or more heteroatoms selected from O, N or S. The "heterocycloalkyl" as defined above may be optionally substituted with a designated number of substituents as set forth in the embodiment recited above. Examples of heterocycloalkyl include, but are not limited to, morpholine, piperidine, piperazine, pyrrolidine, and thiomorpholine. As used herein, alkyl groups include straight chained and branched hydrocarbons, which are completely saturated.

As used herein, sulfonamide means the group —NHSO$_2$—, e.g., when A is sulfonamide, E-A is C(R3)(R4)-NHSO$_2$—. As used herein, acylsulfonamide means —C(O)NHSO$_2$—, e.g., when A is acylsulfonamide, E-A is C(R3)(R4)-C(O)NHSO$_2$—.

In Structural Formulas depicted herein, when more substitutents are indicated on a group than are chemically possible one skilled in the art will appreciate that excess substituents are intended in the alternative.

A bond to the center of a cyclic group indicates that the bond is to any substitutable atom in the ring. When a bond passes through a ring and ends in the center of a second ring, the bond is to any substitutable ring atom in either ring.

In certain aspects the ligand is: N-{5-[4-(4-methyl piperazine methyl)-benzoylamido]-2-methylphenyl}-4-[3-(4-methyl)-pyridyl]-2-pyrimidine amine; N-{5-[4-(4-methyl piperazine methyl)-benzoylamido]-2-methylphenyl}-4-[3-(4-ethyl)-pyridyl]-2-pyrimidine amine; N-{5-[4-(4-methyl piperazine methyl)-benzoylamido]-2-methylphenyl}-4-[3-(4-(2-propyl)-pyridyl)]-2-pyrimidine amine; N-{5-[4-(4-methyl piperazine methyl)-benzoylamido]-2-methylphenyl}-4-[3-(4-methyl)-pyridyl]-2-pyrimidine amine; N-{5-[4-(4-methyl piperazine methyl)-benzoylamido]-2-methylphenyl}-4-[3-(5-phenyl)-pyridyl]-2-pyrimidine amine; N-{5-[4-(4-methyl piperazine methyl)-benzoylamido]-2-methylphenyl}-4-[3-(5-(4-pyridinyl)-pyridyl]-2-pyrimidine amine; or N-{5-[4-(4-methyl piperazine methyl)-benzoylamido]-2-methylphenyl}-6-methyl-4-(3-pyridyl)-2-pyrimidine amine.

In a further aspect, the ligand is comprised in a lipid formulation. The lipid formulation can comprise one or more cationic lipids. The cationic lipid can include, but is not limited to 1,2-dimyristoyl-sn-glycero-3-phosphocholine (DMPC), N,N-dioleyl-N,N-dimethylammonium chloride (DODAC); N-(2,3-d-ioleyloxy)propyl-N,N—N-triethylammonium chloride (DOTMA); N,N-distearyl-N,N-dimethylammonium bromide (DDAB); N-(2,3-dioleoyloxy)propyl)-N,N,N-trimethylammonium chloride (DOTAP); 313-(N—(N',N'-dimethylaminoethane)-carbamoyl)cholesterol (DC-Chol), N-(1-(2,3-dioleyloxy)propyl)-N-2-(sperminecarboxamido)ethyl)-N,N-dimethylammonium trifluoracetate (DOSPA), d-ioctadecylamidoglycyl carboxyspermine (DOGS), 1,2-dileoyl-sn-3-phosphoethanolamine (DOPE), 1,2-dioleoyl-3-dimethylammonium propane (t1DODAP), or N-(1,2-dimyristyloxyprop-3-yl)-N,N-dimethyl-N-hydroxyethyl ammonium bromide (DMRIE). The composition may also comprise cholesterol or cholesterol derivative.

Embodiments of the invention also include methods of treating a hyperproliferative condition comprising providing an effective amount of a protein ligand to a subject having, suspected of having, or at risk of developing the hyperproliferative condition, wherein the protein ligand selectively inhibits a protein kinase, wherein the protein ligand is represented by one or more of the compounds described herein. In certain aspects, the protein kinase is associated with a hyperproliferative condition, including but not limited to cancer. In further aspects, the cancer is a blood borne cancer, including but not limited to leukemias.

Aspects of the invention include methods of optimizing a target protein-first ligand complex, and the products of such a method, that include the steps of: (a) assessing one or more nonconserved packing defects in the target protein-first ligand complex; and (b) engineering a second ligand having a structural feature that complements the nonconserved packing defect. The target protein can be an enzyme, such as a kinase, particularly a protein kinase. In further embodiments, the activity of the protein kinase is associated with a hyperproliferative condition. In still further embodiments the hyperproliferative condition is cancer. A cancer may include, but is not limited to leukemia. The first ligand and/or the second ligand (wrapper compound) inhibit an activity of the target protein. In a further aspect, the specificity of the second ligand for the target protein is greater than that of the first ligand. In still further aspects, the specificity and affinity of the second ligand for the target protein is greater than that of the first ligand for the target protein. In still further aspects, the undesirable interactions of the first ligand are reduced or eliminated in the second ligand.

The methods of the invention can include the step of assessing nonconserved packing defects by modeling hydrogen bond desolvation. The modeling of hydrogen bond desolvation can comprise (a) defining desolvation domains as a fixed radii extending from alpha carbons of a pair of residues forming a hydrogen bond; and (b) determining the extent of desolvation of hydrogen bonds within a protein-ligand or protein-protein complex.

Typically, structural features of the second ligand comprise nonpolar groups capable of penetrating a desolvation domain of the target protein. In certain aspects the extent of hydrogen bond desolvation is quantified as the number of nonpolar groups contained within the desolvation domain. In particular aspects, a packing defect includes a hydrogen bond with a hydrogen bond desolvation of less that about 20, 19, 18, 17 or fewer nonpolar groups. The methods can include a step comprising assessing packing similarity between two related proteins.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

where $X_n, Y_n$ represent respectively the normalized values of the negative logarithm of binding constants for complexation of kinase and kinase with drug n.

Figure 3:
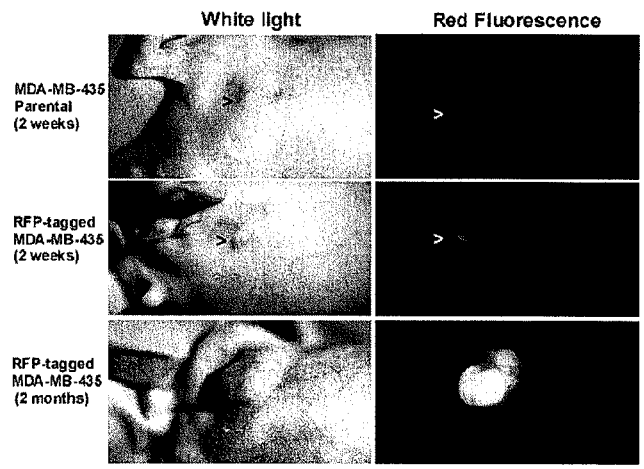

FIG. 3 Multi-spectral images of nude mice with subcutaneous tumors (MDA-MB-435 cells). The top row shows white light and fluorescence images of tumors formed with the parental cell line. Middle row after 2 weeks following injection. The bottom row shows white light and fluorescence images of tumors formed.

Figure 4:
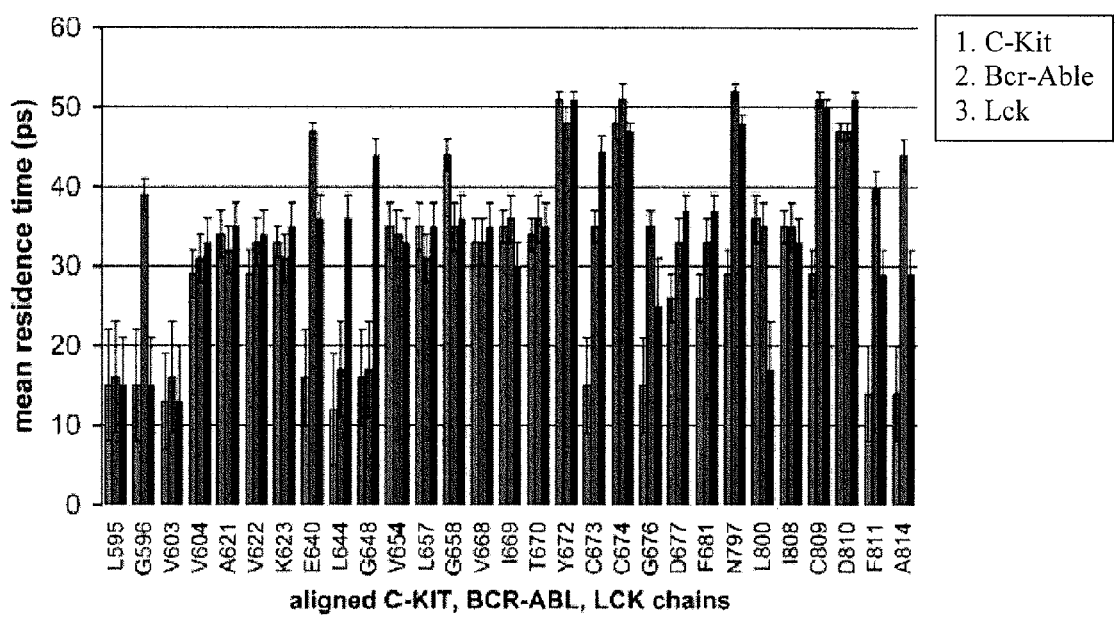

FIG. 4 Dewetting propensities of C-Kit residues in contact with imatinib (PDB.1T46) and of aligned residues in Bcr-Abl kinase (PDB.1FPU) and Lck (PDB.3LCK). Residue i is in contact with the ligand if an atom of the latter lies within its domain D(i). The de-wetting propensity is quantified by the mean lifetime of solvating water molecules. Error bars denote Gaussian dispersion over 5 MD runs.

Figure 5A:
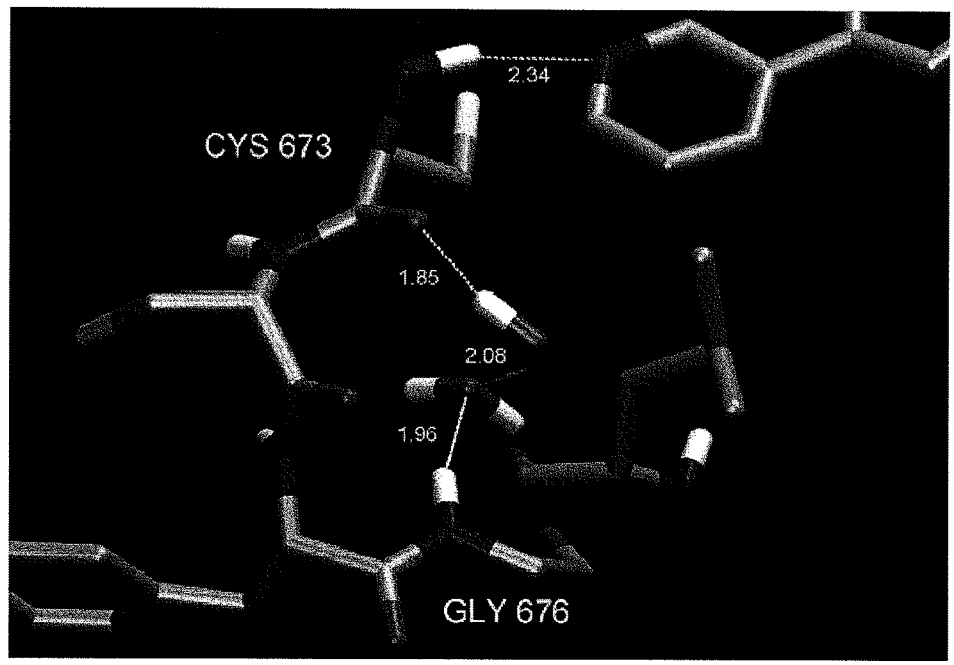
Figure 5B:
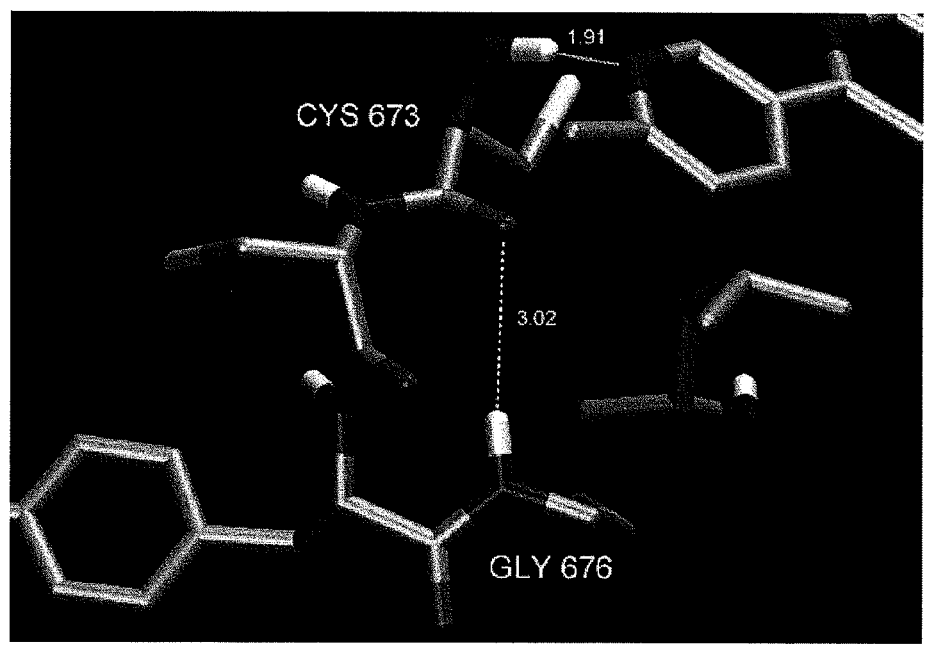

FIGS. 5A-5B (FIG. 5A) Snapshot of the SBMD simulation for C-Kit kinase bound to imatinib at 1 ns. The main-chain hydrogen bond between Cys673 and Gly676 is competitively and irreversibly replaced by hydrogen bonding to a water molecule, revealing the instability of the intramolecular interaction. (FIG. 5B) Snapshot of the SBMD simulation of C-Kit kinase in complex with WBZ_4 at 1 ns. The main-chain hydrogen bond between Cys673 and Gly676 is stabilized by the water expulsion promoted by the added methyl on the inhibitor.

Figure 6A:
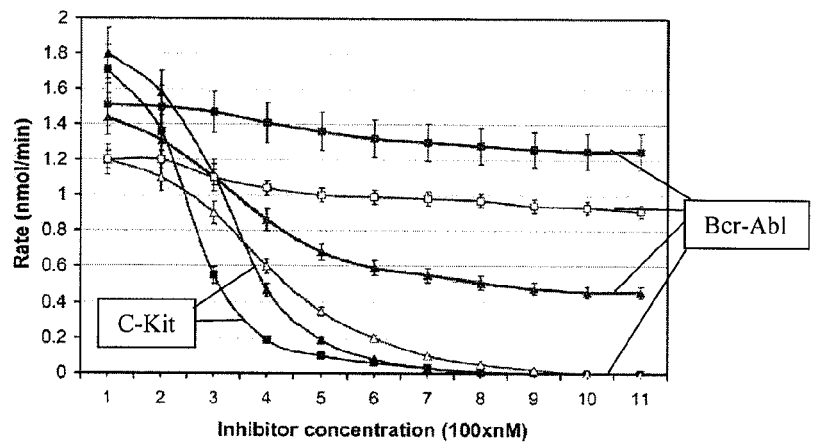
Figure 6B:
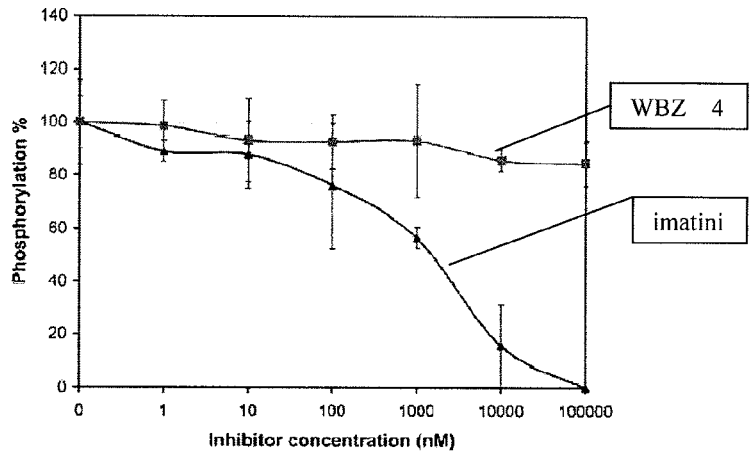
Figure 6C:
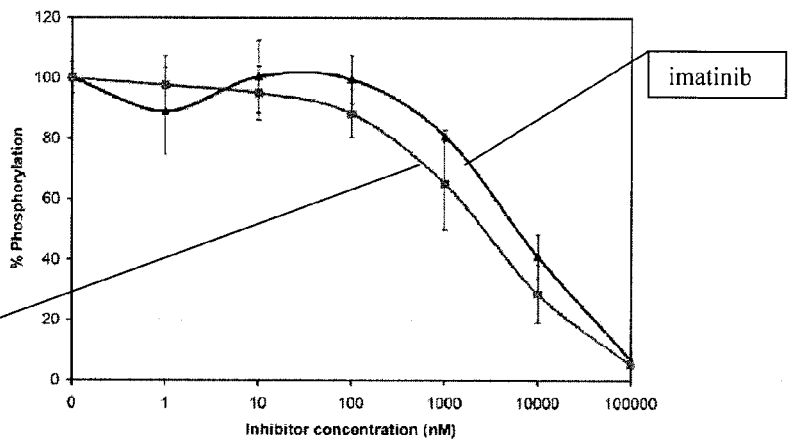

FIGS. 6A-6C. Kinetic inhibitory impact of compounds WBZ_4 and imatinib determined by measuring phosphorylation rates through spectrophotometric assays of C-Kit and Bcr-Abl kinase activity. (FIG. 6A) The kinases are inhibited by WBZ_4 (squares), and by the parental compound (triangles). Phosphorylation rate plots are given for Bcr-Abl and C-kit. The open symbols correspond to inhibition of unphosphorylated Bcr-Abl, while the full symbols correspond to the Tyr412-phosphorylated form. Error bars represent dispersion over 5 runs for each kinetic assay. Notice the selective enhancement of C-kit inhibition by WBZ_4, in contrast with the high impact of imatinib on both kinases. (FIG. 6B) Test-tube phosphorylation inhibition assay for Abl enzyme in the presence of WBZ_4 or imatinib. Active recombinant Abl enzyme (1 µg/mL) and its substrate (Abl-tide, 1 µg/ml) were incubated for 1 hour at 37° C. in the presence of various WBZ_4 or imatinib concentrations. ATP (100 nM) was added to the reaction mixture. Phosphorylation of Abl-tide peptide was detected by incubation in consecutive order with anti-rabbit phospho-Abl-tide antibody and anti-rabbit horseradish peroxidase (HRP) antibody. TMB (3,3,5,5-tetramethylbenzidene) was added to initiate the chromophore reaction and a couple of minutes were allowed for color development. The reaction was terminated by the addition of 1M $H_2SO_4$. Phosphorylation of the substrate was quantified as absorbance units (AU) by spectrophotometry at 450 nm. Values obtained with the enzyme without the inhibitors (WBZ_4 or imatinib) were assumed to be 100% phosphorylation and were compared to the values obtained with the addition of the inhibitors. (FIG. 6C) Test-tube phosphorylation inhibition assay for C-Kit in the presence of WBZ_4 or imatinib. Active recombinant C-Kit kinase (25 ng/ml) and its substrate Poly (Glu4-Tyr, 150 nM) were incubated for 1 hour at 37° C. in the presence of various WBZ_4 or imatinib concentrations. ATP (100 nM) was added to the reaction mixture. Phosphorylation of Poly (Glu4-Tyr) peptide was detected by incubation in consecutive order with anti-phosphotyrosine antibody and antirabbit horseradish peroxidase (HRP) antibody. The prototype WBZ_4 has a higher inhibitory impact on C-Kit than imatinib.

Figure 7A:
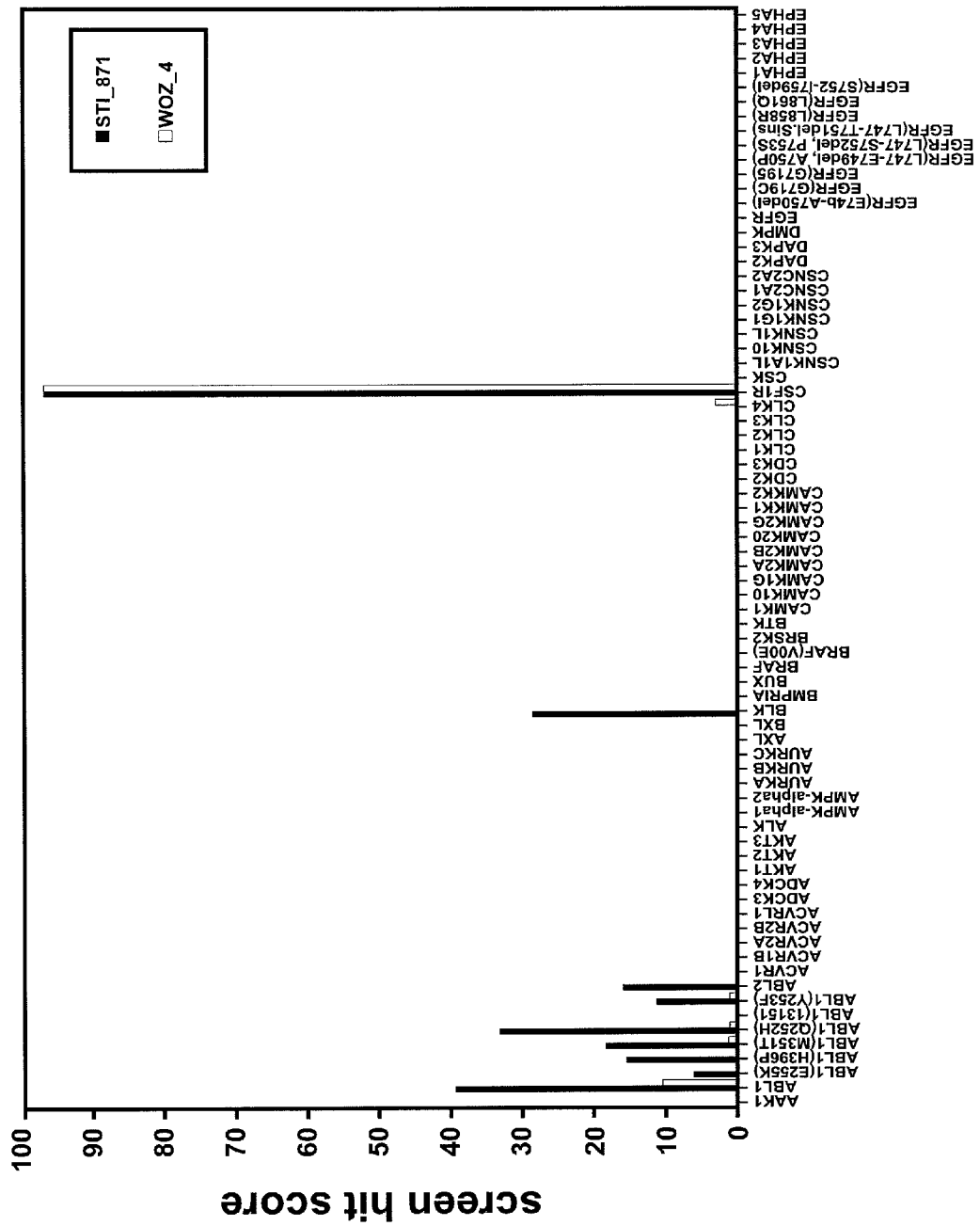
Figure 7B:
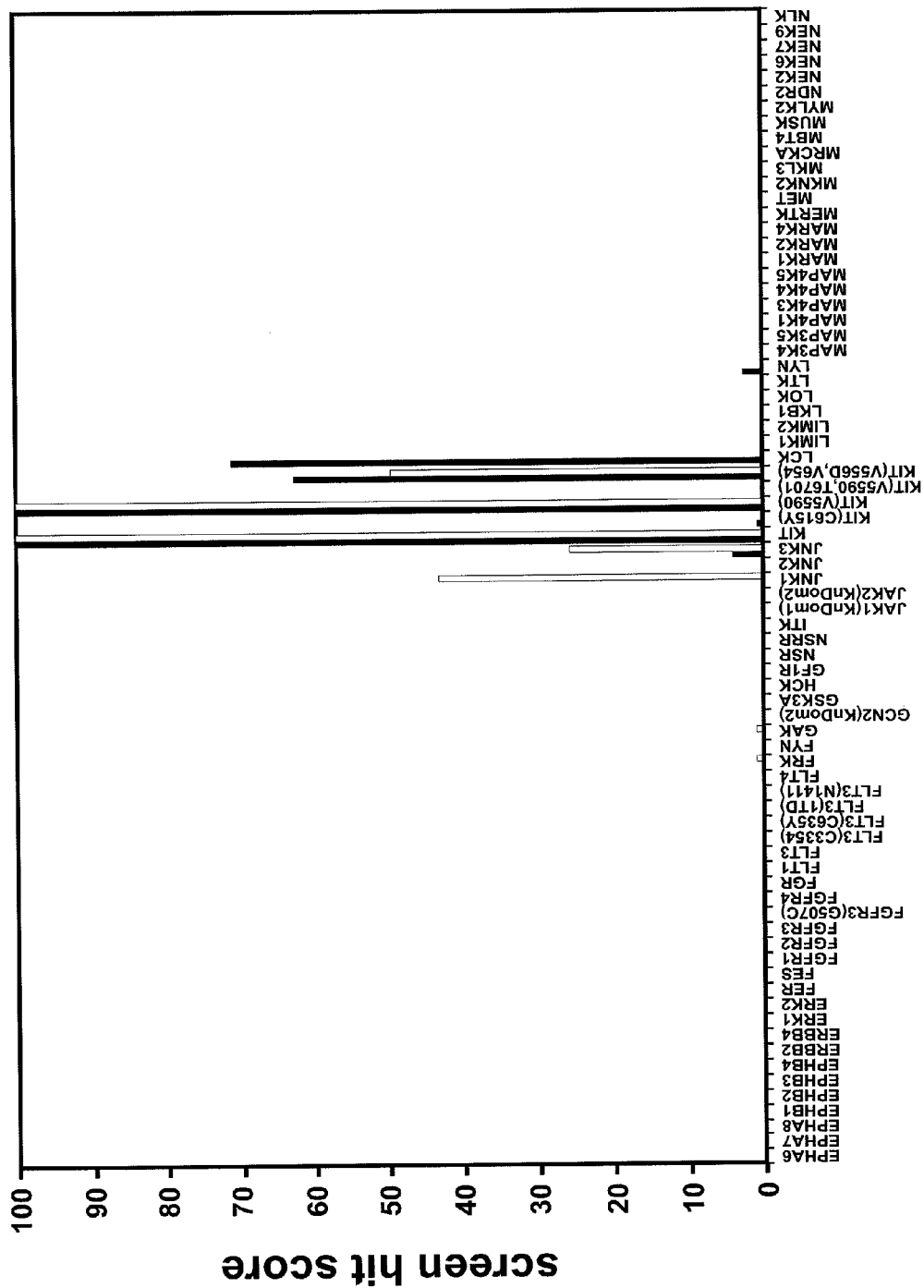
Figure 7C:
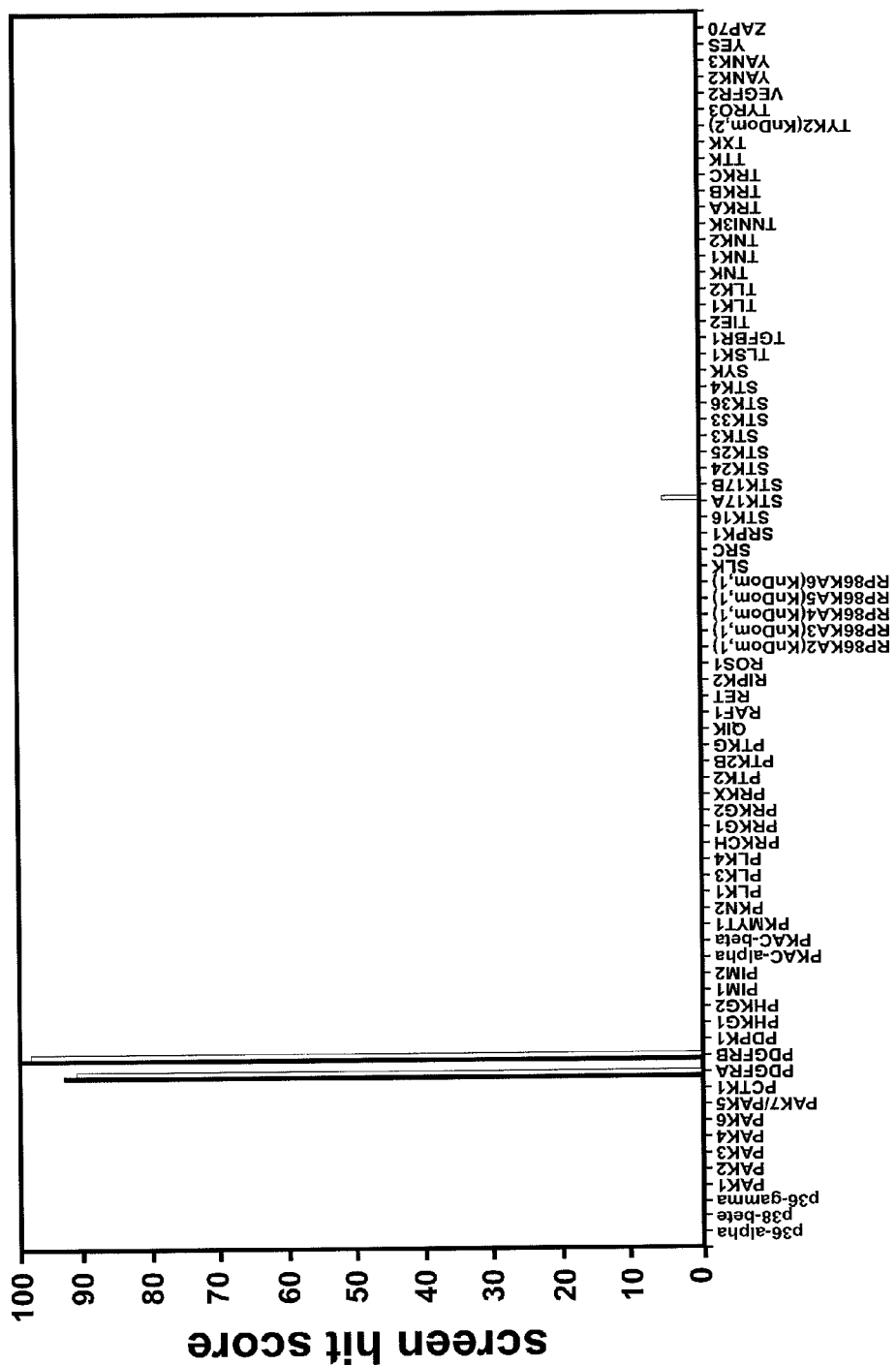

FIGS. 7A-7C High-throughput screening at 10 mM for WBZ_4 and imatinib (STI_571, control) over a battery of 228 human kinases displayed in a T7-bacteriophage library (Ambit Biosciences, San Diego, Calif.). Hit values are reported as percentage bound kinase.

FIGS. 8A-8D. WBZ_4 inhibits cell proliferation of C-Kit positive ST-882 cells. (FIG. 8A) GIST cancer cells ST882 were seeded in 96 wells plates at a density of $8 \times 10^3$ cells per well. The cells were treated with various concentrations of WBZ_4 and imatinib for an additional 48 h. Cell proliferation was determined by Alamar Blue assay. Cell proliferation is expressed as the percentage of proliferating cells relative to untreated cells. The WBZ_4 compound was incorporated into liposomes to facilitate cellular delivery. (FIG. 8B) WBZ_4 does not significantly inhibit cell proliferation of Bcr-Abl positive K562 cells. K562 cells were seeded in 96 wells plates at a density of $1 \times 10^4$ cells per well in 50 µl of medium. Two hours later, 50 µl medium containing different concentrations 0.01, 0.1, 1 µM of liposome-encapsulated WBZ_4 or soluble imatinib were added to the wells to reach a final volume of 100 µl per well. Following 48 h of exposure, the Alamar blue assay was performed. Plates were read at dual wavelength (570-595 nm) in an Elisa plate reader. (FIG. 8C) WBZ_4 inhibits phosphorylation of C-Kit kinase in ST-882 GIST cells. Gel bands from the Western blot assays (Methods) of C-Kit in unphosphorylated and phosphorylated (P—) forms in GIST cells treated with WBZ_4 and imatinib. The β-actin assay was adopted as control. (FIG. 8D) Phosphorylation of Bcr-Abl kinase is not significantly inhibited by WBZ_4 in K562 CML cells. Electrophoretic gel bands for Western blots for phosphorylated (P—) and unphosphorylated Bcr-Abl kinase in CML cells treated with WBZ_4 and imatinib.

Figure 9A:
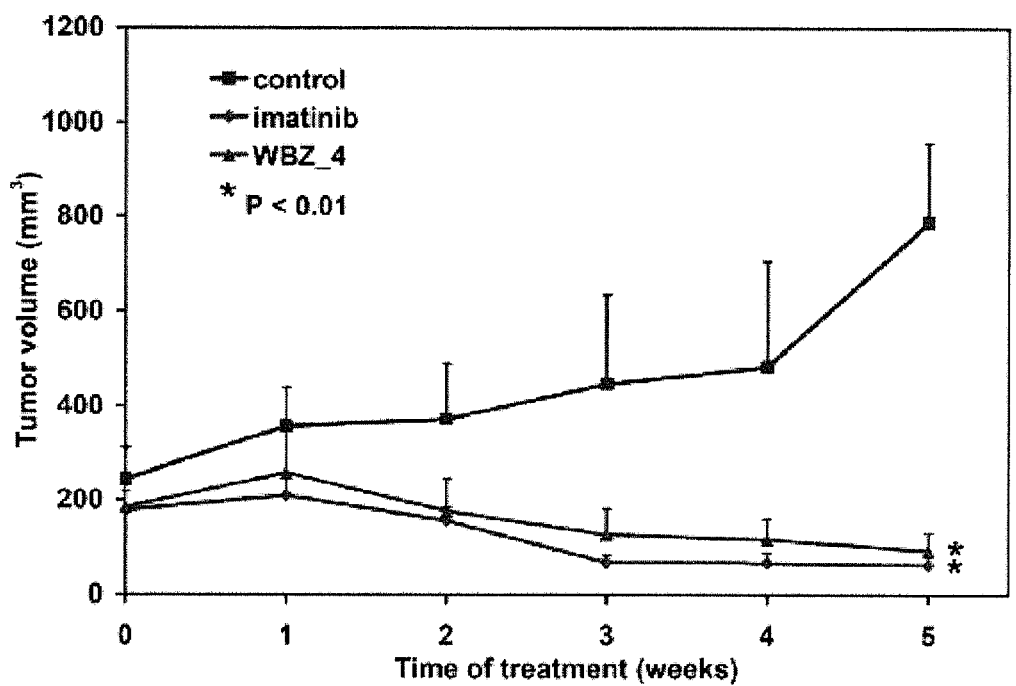
Figure 9B:
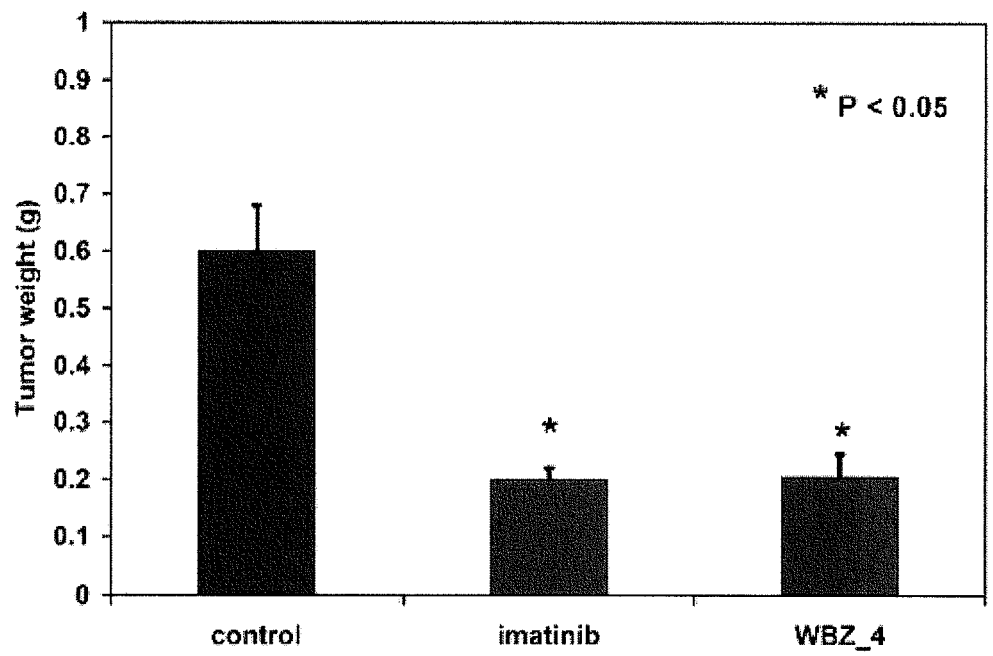
Figure 9C:
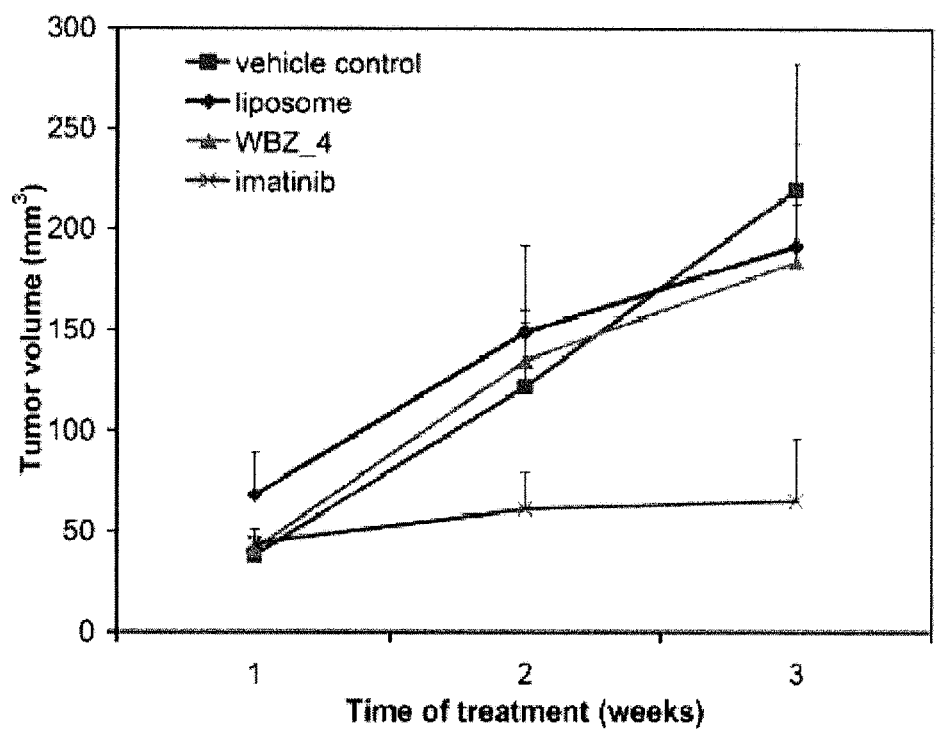

FIGS. 9A-9C Xenograft models of anticancer activity. (FIG. 9A) Effect of WBZ_4 or imatinib therapy on in vivo GIST growth determined by longitudinal tumor volume measurements. Mice were randomized to treatment with either control (normal PBS and empty liposomes give indistinguishable results within experimental uncertainty), imatinib or liposome-formulated WBZ_4. (FIG. 9B) Effect of WBZ_4 or imatibib therapy on in vivo GIST growth determined by weight measurements. Animals from all groups were sacrificed after 6 weeks of therapy, tumors were excised, and the weight was recorded. (FIG. 9C) Effect of WBZ_4 or imatibib therapy on in vivo CML growth induced through a xenograft of K562 tumor cells, determined by longitudinal tumor volume measurement. The WBZ_4 selectivity is hereby corroborated in vivo.

Figure 10:
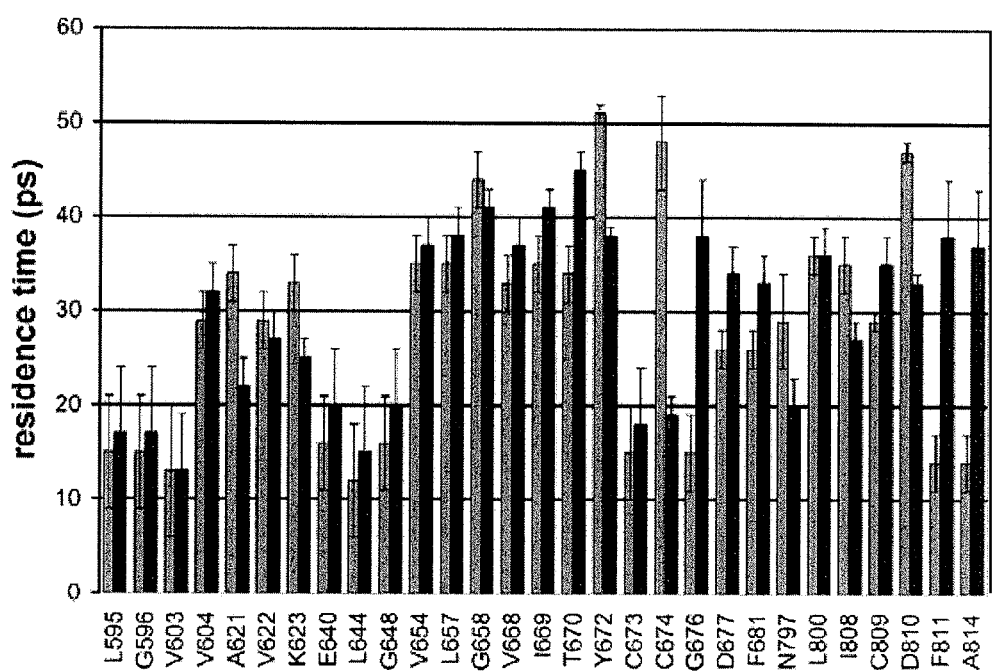

FIG. 10 Aligned de-wetting patterns for C-Kit kinase and JNK1 restricted to the C-Kit residues in contact with imatinib.

Figure 11A:
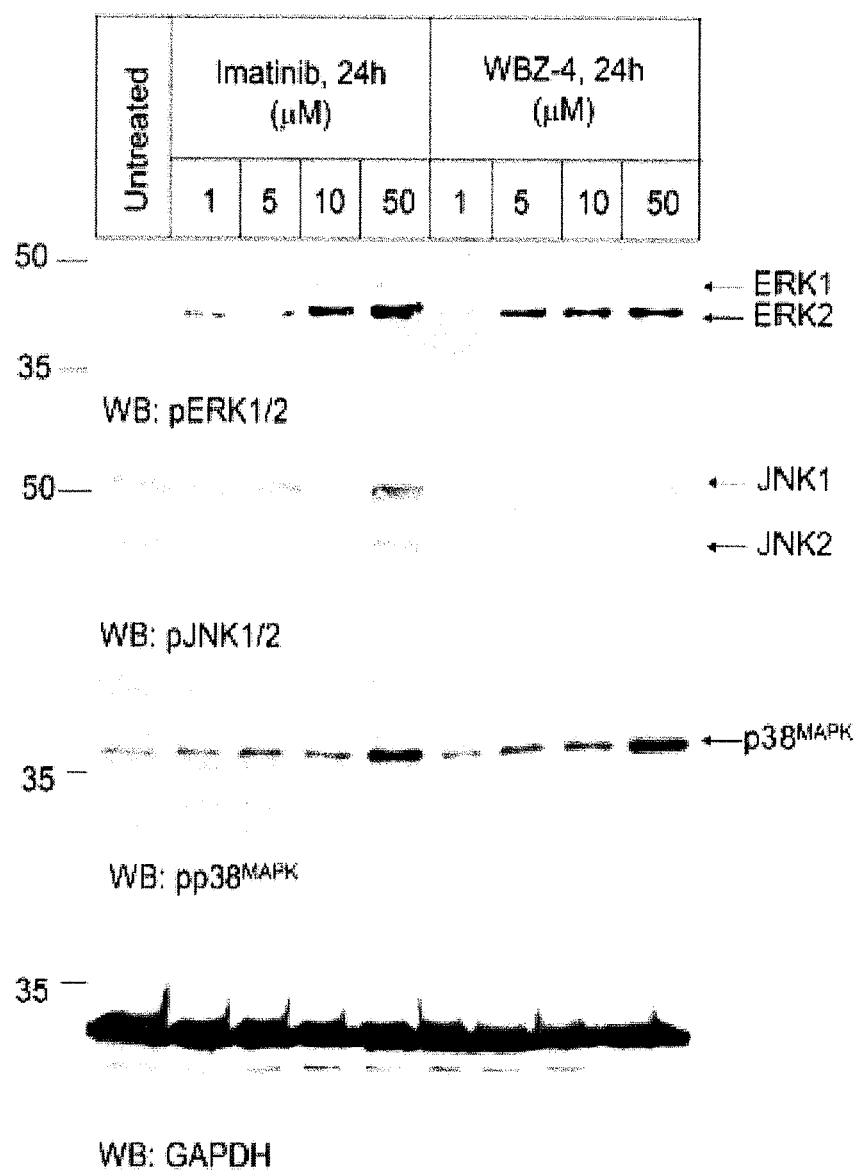
Figure 11B:
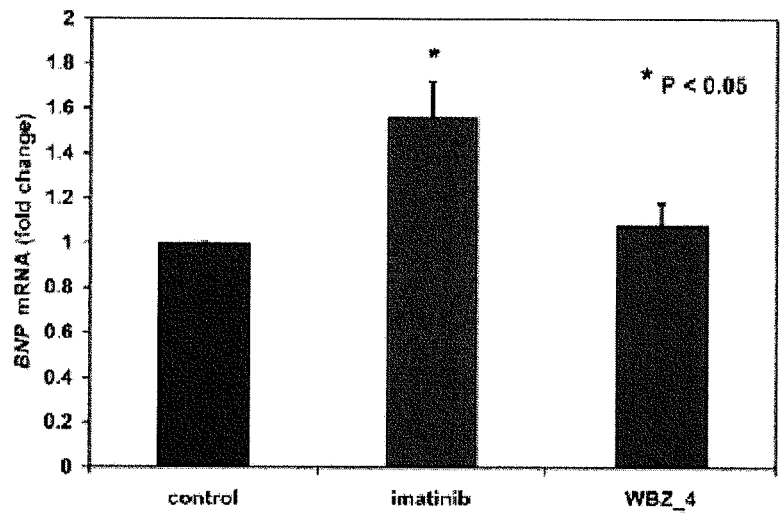
Figure 11C:
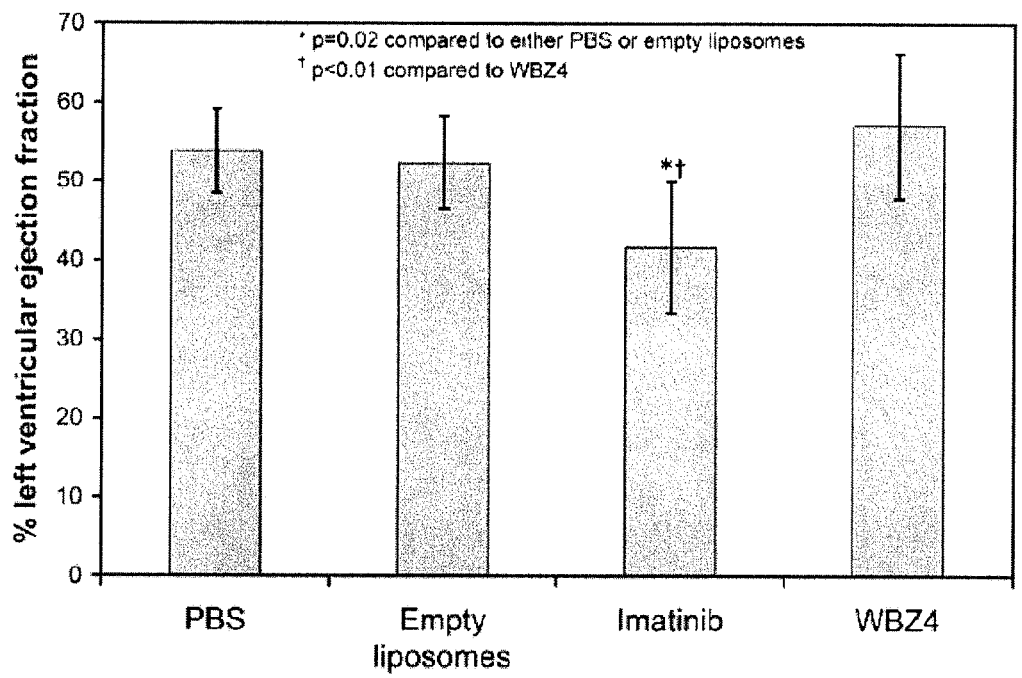

FIGS. 11A-11C (FIG. 11A) Western blot of JNK inhibition in cardiomyocytes. Equal amounts of extracted cellular protein (50 μg per lane) were separated by SDS-PAGE and transferred to nitrocellulose membranes. Western blots were then probed with primary antibodies specific for the phosphorylated forms of ERKs, JNKs, and p38MAPK. To ensure equal loading, blots were also probed with an antibody specific for GAPDH. The position of molecular weight standards is indicated to the left of each blot. (FIG. 11B) Effect of WBZ_4 or imatinib therapy on mouse heart brain natriuretic peptide (BNP). The mRNA levels of BNP (a sensitive marker of myocardial hypertrophy and cardiac impairment) were examined in the left ventricle of mice from the groups in FIG. 9A. The BNP mRNA levels were about 58% higher in the ventricles from imatinib-treated animals (p=0.02), but no significant difference was noted in the WBZ_4 treated animals. (FIG. 11C) Comparison of left ventricular ejection fraction after 6 weeks of control (groups treated with either PBS or empty liposomes), imatinib, or WBZ_4 therapy in mice (doses are described in Methods).

Figure 12:
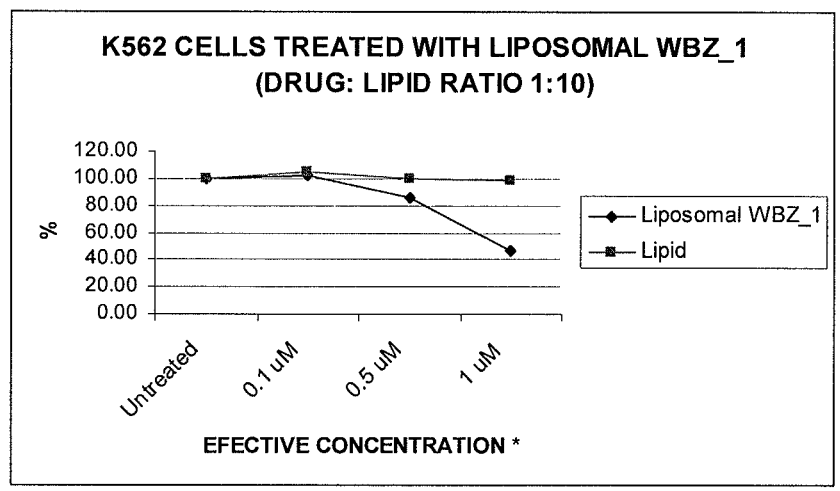

FIG. 12. K562 cells derived from chronic myeloid leukemia (CML) tumors and treated with WBZ_1 liposomal formulation using drug:lipid ratio 1:10. Cells were plated in a 96 well plate at a concentration of 10,000 cells per well and were treated 2 hours later. After 48 hours incubation, an Alamar blue assay was performed. Cells proliferation was expressed as the percentage of proliferating cells compared to the untreated. Anticancer activity of WBZ_1 is revealed by this preliminary assay. (*) This concentration is the maximum uptake that was calculated based on previous work using a similar system (Tari, 1996). The actual cellular uptake can be considerable lower, even $10^{-3}$ times the effective concentration. The inventors can determine the exact uptake in future experiments using a radiolabeled lipid and prototype compound.

Figure 13:
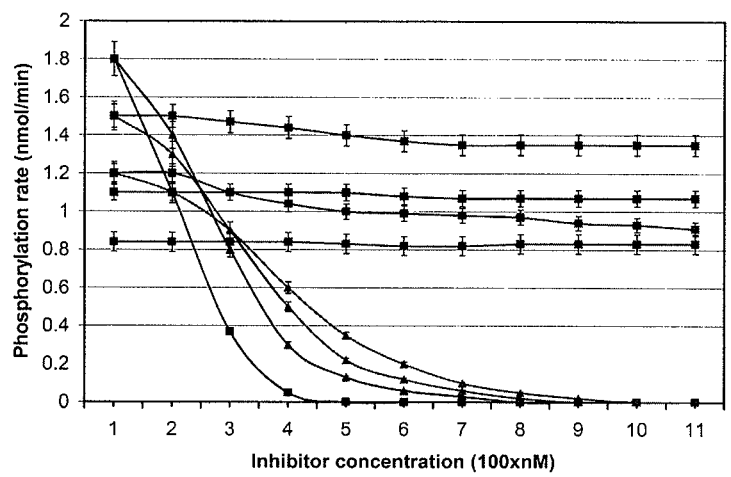

FIG. 13 Rate of phosphorylation of Bcr-Abl, C-kit, Lck, Chk1, and Pdk1 in the presence of imatinib (triangles) and in the presence of the I, II-methylated modified imatinib (squares). The latter compound was designed to better wrap the nonconserved dehydrons in Bcr-Abl. Within the means of detection, the kinase phosphorylation rates do not vary appreciably in the range 0-100 nM inhibitor concentration. To determine the level of selectivity of drug inhibitors designed by adopting the wrapping technology, kinetic assays of the inhibition of multiple kinases have been conducted. To measure the rate of phosphorylation due to kinase activity in the presence of inhibitors, a standard spectrophotometric assay has been adopted (Schindler et al., 2000) in which the adenosine diphosphate production is coupled to the NADH oxidation and determined by absorbance reduction at 340 nm. Reactions were carried out at 35° C. in 500 μl of buffer (100 mM Tris-HCl, 10 mM MgCl2, 0.75 mM ATP, 1 mM phosphoenol pyruvate, 0.33 mM NADH, 95 units/ml pyruvate kinase). The adopted peptide substrates (Invitrogen/Biaffin) for kinase phosphorylation are: AEEEIYGEFEAKKKKG (SEQ ID NO:1) for unphosphorylated Bcr-Abl (Schindler et al., 2000); KVVEEINGNNYVYIDPTQLPY (SEQ ID NO:2) for C-kit (Timokhina et al., 1998); GLARLIED-NEYTAREGAKFPI (SEQ ID NO:3) for LCK (Perlmutter et al., 1988); GCSPALKRSHSDSLDHDIFQL (SEQ ID NO:4) for Chk1 (Zhao et al., 2002); and EGLGPGDTTSTFCGTP-NYIAP (SEQ ID NO:5) for Pdk1 (Le Good et al., 1998).

Figure 14:
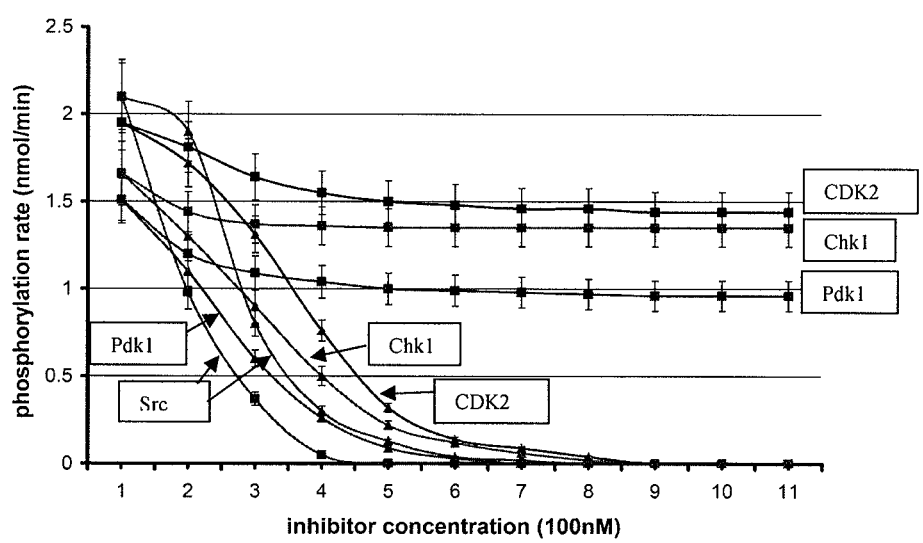

FIG. 14 Phosphorylation rates of Src, CDK2, Chk1 and Pdk1 in the presence of staurosporine (triangles) and in the presence of the staurosporine methylated at the imide N6 of the indole ring (squares). The latter compound was designed to better wrap the nonconserved dehydron Gln250-Glu267 in Src kinase. Error bars represent dispersion over 10 runs for each kinetic assay. Within the means of detection, the kinase phosphorylation rates do not vary appreciably in the range 0-100 nM inhibitor concentration. The following peptide substrates (Invitrogen/Biaffin) for kinase phosphorylation were chosen for their high specificity: KVEKIGEGTYGVVYK (SEQ ID NO:6) for SRC (Cheng, 1992); HHASPRK (SEQ ID NO:7) for CDK2 (Brown et al., 1999); GCSPALKRSHSD-SLDHDIFQL (SEQ ID NO:4) for Chk1 (Zhao et al., 2002); and EGLGPGDTTSTFCGTPNYIAP (SEQ ID NO:5) for Pdk1 (LeGood et al., 1998).

DETAILED DESCRIPTION OF THE INVENTION

Cancer remains an unsolved purge of modern society. Molecularly targeted drug-based therapy and image-based diagnosis are regarded as two of the most valuable tools in the struggle against the disease (Druker, 2004; Levitzki and Gazit, 1995; Tibes et al., 2005). However, due to the cross reactivity of available protein ligands (Patel et al., 2005; Bain et al., 2000; Couzin, 2005; Hopkins et al., 2006; Knight and Shokat, 2005), these procedures may become very noisy and rendered useless or potentially health-threatening. On the other hand, unforeseen cross reactivity has proven to be virtually unavoidable in current combinatorial approaches to drug discovery (Fabian et al., 2005).

Thus, target specificity and the modulation of selectivity towards targets of clinical relevance are critical issues in drug-based therapy and imaging diagnosis. In this regard, the fundamental problem of the molecular basis for noise or cross reactivity in drug therapy and for the lack of image contrast in detection can be addressed. In addition, this problem can be reduce to sharpen the focus and specificity on clinical targets such as kinases, particularly those implicated in disease states. The inventors introduce a novel concept in biomolecular design using a translational platform that contains basic, applied and clinical components giving rise to a new discipline: Molecular Theranostic Engineering.

Specificity is not essential for clinical activity. The therapeutic success of imantinib (Gleevec) is a good illustration of this fact (Donato and Talpaz, 2000). On the other hand, the knowledge acquired from intense clinical use of imatinib indicates that, although clinical activity is achieved, the non-selectivity for the target leads to side effects such as skin and hematopoietic toxicities (Donato and Talpaz, 2000; Faderl et al., 1999). Aspects of the present invention include controlled target selectivity directed towards a predetermined set of clinically relevant targets that can lead to reduced toxicity and enhanced antitumor activity. The inventors' contention is that although specificity may not be required for clinical activity, controlled selectivity focusing the impact on targets devoid of toxicity may improve the therapeutic index of kinase inhibitors. Thus, the inventors introduce a novel marker for specificity (a dehydron) and use it to re-design available drugs in order to modulate their selectivity towards targets of known clinical relevance for both diagnosis/detection and therapeutic purposes.

The methods described herein can be used to tackle central therapeutic problems involving selective drug-based inhibition of cancer-related kinases (Bain et al., 2003; Fabian et al., 2005). As a result, compositions will be designed as wrappers of packing defects and result in efficient selective inhibitors and/or imaging probes. The methodology is based on at least: (a) the discovery of the novel structural feature, the dehydron, that differentiates evolutionarily related proteins representing alternative drug targets; (b) the targeting of dehydrons, and (c) the selectivity of commercially available drugs that are unintentionally based on the dehydron footprint of the kinases, although the drugs were not purposely design to wrap packing defects.

Aspects of the present invention address a problem considered to be the graveyard of most drug-discovery or ligand design efforts: toxic side effects. Side effects may be due to at least two discernible causes: (a) the target protein is involved in several pathways, causing the drug/ligand to perturb off-target pathways, and/or (b) the drug/ligand is cross-reactive in the sense that its intended target possesses several paralogs which offer potential alternative binding sites (Fabian et al., 2005; Fernandez, 2005). Drug discovery remains a semi-empirical endeavor, essentially supplemented by structural intuition. Thus, it is unlikely that the high levels of cross reactivity detected in high throughput screening experiments (Fabian et al., 2005) will be tempered or modulated using rational design, unless a new approach is able to discern paralogs above and beyond what a structural characterization may reveal.

These properties make dehydrons ideal targets to minimize cross-reactivity in the inhibitory impact of a potential drug (Schindler et al., 2000), that is to wrap the packing defect or dehydron. Thus, dehydrons can be used in novel drug-design concepts (Fernandez et al., 2004) of enormous potential, i.e., a wrapping technology. Thus, the innovative concept of "an inhibitor as a wrapper of protein packing defects" will be described and exemplified herein.

I. Wrapping Technology

Figure 1:
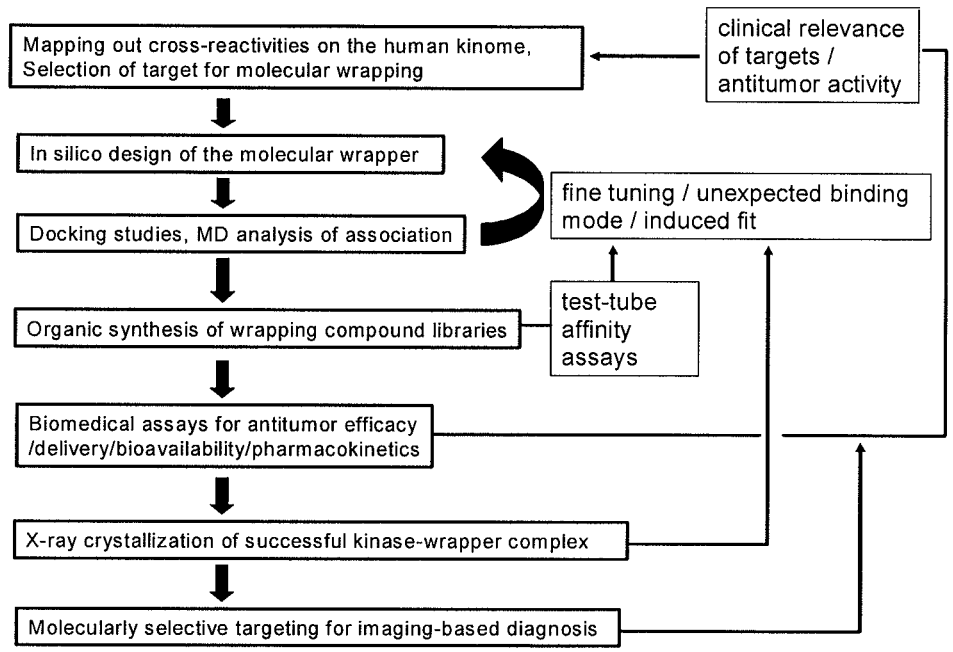
FIG. 1 Molecular Theranostic Engineering at work. Flow chart of the pipelined discovery/translational components, their interrelationships, and feedback mechanisms for adaptation and refinement needed to fine tune the design strategy.

An overview of molecular design method (Molecular Theranostic Engineering) of the present invention is illustrated in FIG. 1. As described herein, packing defects adopt the form of under-wrapped backbone hydrogen bonds, i.e., dehydrons, and may be identified from the atomic coordinates of protein structure, according to the following tenets: (1) The extent of intramolecular hydrogen-bond desolvation, $\rho$, in a monomeric structure is quantified by determining the number of nonpolar groups (carbonaceous, not covalently bonded to an electrophilic atom) contained within a desolvation domain. (2) The desolvation domain is defined as two intersecting spheres of fixed radius centered at the $\alpha$-carbons of the residues paired by the backbone amide-carbonyl hydrogen bond. The statistics of hydrogen-bond wrapping depend on the choice of desolvation radius, but the tails of the distribution invariably single out the same dehydrons in a given structure over a 6.2-7.0 Å range in the adopted radius. In certain examples 6.4 Å was used.

In folds for soluble proteins at least two thirds of the backbone hydrogen bonds are wrapped on average by $\rho=26.6\pm7.5$ nonpolar groups (Fernandez and Berry, 2005; for other measures of wrapping see Fernandez and Scheraga, 2003). Dehydrons are here defined as hydrogen bonds whose extent of wrapping lies in the tails of the distribution, i.e., with 19 or fewer nonpolar groups in their desolvation domains, so their $\rho$-value is below the mean, minus one Gaussian dispersion.

A "packing distance" is defined by comparing the different packing arrangements of the hydrogen bonds framing the ATP sites of different kinases. As indicated above, packing differences between ATP-sites may be turned into a useful distance between kinases by following one or more of four steps: (a) alignment of hydrogen-bond matrices; (b) derivation of dehydron matrices that inherit their alignment from step (a); (c) restricting dehydron matrices to the ATP sites; and (d) computing the Hamming distance between restricted dehydron matrices.

A hierarchical clustering of kinases based on the packing metric was determined across the 32 kinases reported in PDB for which affinity fingerprinting was experimentally and independently obtained (Fabian et al., 2005). Seventeen inhibitors were selected from a pool of 20 that have been independently assayed for cross reactivity against a set of 113 kinases. Three inhibitors, staurosporine, SU11248 and EKB243 were excluded from the computation since their high promiscuity is indicative of a mode of anchoring based on hydrophobic interactions with highly conserved nonpolar residues and not on dehydron wrapping, as indicated below. The packing-based hierarchical clustering of the kinases is built so that the minimum number of nodes along a walk from one protein-node to another is proportional to their Hamming distance. Typically, in computing packing distances for a protein chain of length N a matrix of dehydrons Dij, i, j= 1, 2, . . . , N is constructed by choosing Dij=1 if residues i and j are paired by a dehydron and Dij=0 otherwise. Then a Hamming distance MH (X,Y), which serves as an indicator of the packing distance between proteins X and Y is given by:

$$M_H(X, Y) = \sum_{i<j} |D_{i,j}(X) - D_{i,j}(Y)|$$

where D(X) and D(Y) represent respectively the dehydron matrices for kinases X and Y.

Figure 2:
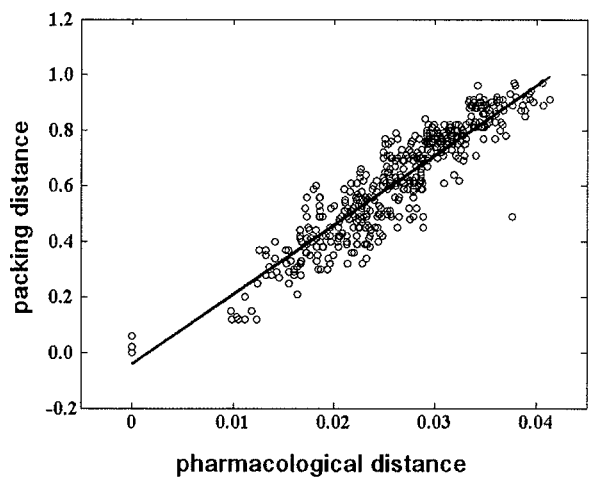
FIG. 2 Correlation between packing distance and pharmacological distance for all pairs constructed from a pool of 32 PDB-reported kinases independently fingerprinted for affinity against 17 drugs. The pharmacological distance between two kinases is defined as the Euclidean distance between the normalized affinity vectors with entries corresponding to the negative logarithm of the binding constants reported in Fabian et al. (2005). The pharmacological matrix (PM) is obtained by calculating the pharmacological distances between all kinase pairs $$PM_{X,Y} = \|X - Y\| = \sqrt{\sum_{n \in set\ of\ inhibitors} (X_n - Y_n)^2}$$

The hierarchical clustering is thus equivalent to a packing-distance matrix and, as such, contrasted with a pharmacological distance matrix. The latter is obtained by computing the Euclidean distance between ligand-affinity vectors in R17 with entries given in—in scale (or dimensionless $\Delta G/RT$ units, with $\Delta G$=Gibbs free energy change associated with binding, R=universal gas constant, T=absolute temperature). By plotting packing versus pharmacological distance (FIG. 2) for each pair of kinases reported in PDB and fingerprinted for affinity against the 17 drug ligands, the inventors establish a strong correlation ($R2=0.9028$). This correlation reveals that the pattern of packing defects is statistically an operational selectivity filter for drug design, even though individual drugs were not purposely designed to wrap packing defects in proteins. Thus, the inventors are taking advantage of this hitherto overlooked design feature to dramatically simplify the drug development effort and rationally enhance selectivity towards clinically significant targets. The combined use of a sequence-based selectivity filter and novel structure-threading algorithms enable us to focus on the entire human oncokinome.

A. Computational/In-Silico Design Phase

In certain aspects, the inventors have developed a new generation of highly selective drug-based inhibitors in the form of small-ligand molecules that wrap packing defects in kinases, protecting them from water attack. Such packing defects have been defined and characterized, and constitute markers for functionality and interactivity. The approach is motivated by the need to avert side effects resulting from alternative "off target" binding of the inhibitor. An enhanced specificity is achievable because packing defects are typically not conserved across evolutionarily related proteins. Thus, the packing of a protein may be used as a selectivity filter in drug design and possibly as a selectivity switch. The latter possibility arises as the inhibitory impact of a ligand is redirected based on packing differences among paralogs.

The in-silico design component comprises one or more of the following steps: First, identification of kinases known to be targets for lead compounds that exert a more or less diffuse inhibitory impact on the human kinome. Second, examination of the packing differences across the paralogs of the selected kinase. Since paralogs typically share the same fold, their structures (threaded or reported) may be aligned, and therefore their packing differences may be quantified. Because the parental ligand was not purposely designed to wrap nonconserved packing defects, the paralogs are likely to be engaged in off-target alternative associations with the ligand. In one embodiment, the inventors focus on inhibitors for which there exists a cross-reactivity profile against a significant number of kinases. The goal is to reduce and control cross reactivity by re-designing the inhibitor according to the data gathered, turning it into a wrapper of the packing defects that are not conserved across paralogs of the target kinase. To be able to design based on a trustworthy structural context, one may focus on inhibitors whose complexation with a selected target protein is reported in PDB, so that nonconserved packing defects may be identified with full certainty.

Once the chemical modifications of ligands are designed, the binding modes of these new compounds in the targeted binding site will be assessed and compare with the binding of the parental compound. This can be performed by computational docking. Docking, which is widely used to predict the binding modes and affinities of small molecules to receptors, is pivotal for molecular matching. Ever since Kuntz et al. (1982) published the first docking algorithm DOCK more than twenty docking programs have been developed. Recent reviews show that the maturation of the algorithms have significantly improved the prediction accuracy of docking programs (Kellenberg et al., 2004). Typically, three robust molecular docking programs will be used, Dock4.0 (dock.compbio.ucsf.edu), FlexX1.7 (biosolveit.de/flexx) and GOLD2.0 (ccdc.cam.ac.uk/products/life sciences/gold). These programs use different scoring algorithms. Therefore, consensus-ranking results can be used for determining final hits (Wang and Wang, 2001).

Dock 4.0 program, developed by Kuntz group at UCSF, uses shape matching algorithm running on a supercomputer, which highly accelerates the docking process (Shoichet et al., 1993; Taylor et al., 2002). In certain aspects, Dock 4.0 will be used as a tool for initial large-scale virtual screening to prefilter the binding modes. All hydrogen atoms and charges will be added by molecular simulation program SYBYL 7.0. For more rigid and accurate computation, analysis of the high priority compounds will be carried out using the programs FlexX and GOLD to increase the prediction accuracy and reliability (Wang and Wang, 2001; Jones et al., 1997; Schellhammer and Rarey, 2004; Kramer et al., 1999). These three programs use different docking algorithms, and using them together to generate consensus-ranking results will improve the chances of finding relevant hits. These combinatorial approaches have been proven very valuable in many instances (Wang and Wang, 2001).

Certain aspects of the invention focus on packing defects in the target kinase that are not conserved across paralogs, re-engineering of a ligand in-silico, and introducing nonpolar-group substitutions aimed at wrapping the nonconserved packing defects. Added nonpolar groups should contribute to the thermodynamically favorable removal of water surrounding the packing defect. The re-engineered ligand is expected to be a more selective inhibitor than the parental compound. While variable levels of selectivity response to packing differences have been observed for available drugs, the packing distance matrix constructed according to methods described herein will enable a strategy to design inhibitors with controlled cross reactivity. Thus, the inventors use imatinib as an exemplary parental compound and other structurally well documented pharmacokinomes to sharpen, modulate, and/or redirect the inhibitory impact. Embodiments of the invention also may use the wrapping strategy to single out clinically relevant targets that may be selectively inhibited by modifying very promiscuous ligands, such as staurosporine.

B. Organic Synthesis/Affinity Optimization

The synthetic methods used to produce the parental compound will be modified to synthesize libraries of inhibitor compounds intended to function as wrappers of the nonconserved packing defects of a chosen target. These wrappers or second ligands are designed according to the methods described herein. While the design of molecular prototypes is rationally directed by packing differences among paralogs, the optimization of their affinity and specificity has an empirical component: libraries of substitutions on lead compounds will be generated and optimized for affinity and specificity. Given the high probability of induced fit in loopy active sites of kinases, establishing a priori which substituent will work best as a wrapper of packing defects will be difficult.

C. Biomedical Assay Phase

In vitro assays can be performed to assess the efficacy of prototype inhibitors based on the wrapping technology, for example, on cancer-derived cell lines. First, the molecular prototypes will be assayed on cell lines to determine basic pharmacological parameters: bioavailability, delivery, cellular uptake, and therapeutic efficacy against tumors. Then, Western blot assays will be systematically performed to construct a cross-reactivity map for the designed ligands. The cross reactivity map will be contrasted against the packing-based distance matrix constructed according to the methods described herein. One of the final outcomes is to always improve over the specificity of the parental compound by following the packing-defect blueprint of the target kinase and taking advantage of the packing differences across its paralogs. These types of assays can be used as components for wrapping-drug development: (a) determination of the toxicity and antitumor activity of the prototypes on experimental murine tumor models; (b) determination of the pharmacokinetic and tissue distribution of the selected prototypes; and (c) determination of the in vivo target modulation of the prototypes in experimental tumors.

D. X-Ray Structural Characterization

Structural characterization of the protein-ligand complexes can be used to dissect the interface between a molecule and a protein target to establish the docking mode and interfacial arrangement of the wrapping molecular prototypes and of their derivative imaging agents. These studies provide a feedback for improvement on design strategies. Issues addressed include: (a) test whether the engineered modifications of lead compounds function as wrappers of packing defects of the target kinases; and (b) test whether the perturbations introduced do not affect the binding mode of the ligand relative to the parental compound.

One of the major issues in studying wrapping is the time-dependence of wrapping interactions. The hydrophobic groups that pack around hydrogen bonds fluctuate in time, therefore one would expect that the solvent accessibility of those dehydrons may change in time. The inventors contemplate using molecular dynamics (MD) simulation to investigate such a time dependence. For all the ligands finalized in design, MD simulation with a stochastic boundary condition will be conducted (Ma et al., 1998; Brooks and Karplus, 1989) in such a way that the sampling is focused in the vicinity of ligand binding site. Various molecular interactions critical for maintaining wrapping of hydrogen bonding in the presence of ligand will be examined. The MD simulation will also be able to help us to assess the local structural perturbation to the protein due to the ligand modifications.

II. Analysis and Synthesis of Compounds

Parental compounds may be selected or identified as those compounds effective against a particular disease state, cell line, or biological activity that for one reason or another is toxic or cross reacts with proteins or pathways that limit the clinical usefulness of the compound. Using commercially available ligands and drug inhibitors as parental compounds, the inventors contemplate introducing a variety of wrapping modifications and assess these compounds on cell lines for enhanced affinity and specificity for a target protein. To be able to design a compound based on a trustworthy structural context, the inventors contemplate focusing on inhibitors that have at least one of the following two conditions that make the wrapping design most reliable: First, cross reactivity must have been independently assessed by profiling the inhibitor for its affinity against a significant number of kinases (Fabian et al., 2005). Second, the complexation of the inhibitor with a selected target protein is structurally reported in PDB (together with paralogs of the target), so that the nonconserved packing defects in the target may be identified with full certainty. On the other hand, cross reactivity inferences will only require packing distances that may be inferred from sequence (Fernandez and Berry, 2004).

Thus, specificity will be molecularly engineered using the wrapping design concept on at least the following drug/target pairs:

| | |
|---|---|
| Staurosporin/CDK2 | (PDB.1AQ 1) |
| Staurosporin/SYK | (PDB.1XBC) |
| Gleevec/SYK | (PDB.1XBB) |
| Erlotinib/EGFR | (PDB.1M17) |
| SB202190/p38MAPK-ERK2 | (PDB.1PME) |
| SB203580/p38MAPK | (PDB.1A9U) |

-continued

| | |
|---|---|
| SP600125/JNK1 | (PDB.1UKH) |
| LY333531/PDK1 | (PDB.1UU3) |

A. Synthesis of Wrapper Compounds

As mentioned above modification of the synthetic methods can be made to produce the wrapper or optimized compounds of the invention. Alternatively the parental compound may be synthesized and then modified using known enzymatic or synthetic methods to produce the wrapper or optimized compounds. Retrosynthesis techniques will be extensively used to generate compound libraries of wrapping substitutions on lead compounds derived from commercially available kinase inhibitors. Such libraries will provide the screening substrate needed to optimize for wrapping/affinity. As an illustration, the retrosynthesis of WBZ_1 utilizing methodology described in the PCT publication WO03027100.

All chemicals and solvents can be obtained from sources known to those of ordinary skill in the art, such as Sigma-Aldrich (Milwaukee, Wis.) or Fisher Scientific (Pittsburgh, Pa.), and used without further purification. Analytical HPLC can be performed on, for example, a Varian Prostar system, with a Varian Microsorb-MW C18 column (250×4.6 mm; 5μ) using the following solvent system A=$H_2O$/0.1% TFA and B=acetonitrile/0.1% TFA. Varian Prepstar preparative system equipped with a Prep Microsorb-MWC18 column (250×41.4 mm; 6μ; 60 Å) was used for preparative HPLC with the same solvent systems. Mass spectra (ionspray, a variation of electrospray) can be acquired, for example, on an Applied Biosystems Q-trap 2000 LC-MS-MS, or the like. UV can be measured on Perkin Elmer Lambda 25 UV/Vis spectrometer or similar instrument. IR can be measured on Perkin Elmer Spectra One FT-IR spectrometer or the like. $^1$H-NMR and $^{13}$C-NMR spectra are recorded on a Brucker Biospin spectrometer with a B-ACS 60 autosampler. (600.13 MHz for $^1$H-NMR and 150.92 MHz for $^{13}$C-NMR), Chemical shifts (δ) are typically determined relative to d4-methanol (referenced to 3.34 ppm (δ) for $^1$H-NMR and 49.86 ppm for $^{13}$C-NMR). Proton-proton coupling constants (J) are given in Hertz and spectral splitting patterns are designated as singlet (s), doublet (d), triplet (t), quadruplet (q), multiplet or overlapped (m), and broad (br). Flash chromatography can be performed using Merk silica gel 60 (mesh size 230-400 ASTM) or using an Isco (Lincon, Nebr.) combiFlash Companion or SQ16x flash chromatography system with RediSep columns (normal phase silica gel (mesh size 230-400ASTM) and Fisher Optima™ grade solvents, or similar equipment and reagents. Thin-layer chromatography (TLC) can be performed on E.Merk (Darmstadt, Germany) silica gel F-254 aluminum-backed plates with visualization under UV (254 nm) and by staining with potassium permanganate or ceric ammonium molybdate.

B. Synthesis of WBZ1 Series:

Referencing scheme 1 below, the synthesis begins with treatment of 2-methyl-5-nitroaniline (1) with 65% nitric acid in ethanol followed by the addition of cyanoamide to give the corresponding 2-methyl-5-nitroaniline-guanidine nitrate (2). Once completed, 3-acetylpyridine (3) is first reacted with phenyl chloroformate at nitrogen position and then regioselectively alkylated using Grignard reagents and catalytic amounts of copper (I) iodide to obtain intermediate dihydropyridine. The dihydropyridine was further deprotected to obtain 3-acetyl-4-methyl-pyridine(4) (Tanis et al., 1996). Product (4) was treated with methyl dimethoxyforamide to give 3-dimethylamino-1-(3-(4-methyl-pyridyl)-2-propene- 1-one (5). Nitrate salt (2) is treated with (5) and sodium hydroxide in refluxing isopropanol to give N-(2-Methyl-5-nitrophenyl)-4-(3-(4-methyl-pyridyl))-2-pyrimidine-amine (6) which is subsequently hydrogenated with 10% palladium on carbon to give N-(2-Methyl-5-aminophenyl)-4-(3-4-methyl-pyridyl)-2-pyrimidine-amine (7). The first WBZ1 synthesis consists of the reaction of α-chloro-p-toluylic acid (8) with 4-methyl-piperazine in ethanol followed by treatment with concentrated HCl to give the corresponding dihydrochloride 4-(4-methyl-piperazin-1-ylmethyl)-benzoic acid (9) which is subsequently treated with thionyl chloride to give the corresponding acid chloride dihydrochloride (10). Subsequent condensation with N-(2-Methyl-5-aminophenyl)-4-(3-(4-methyl)-pyridyl)-2-pyrimidine-amine (7) in pyridine affords the Gleevec analog WBZ1 (PCT publication WO2004108699).

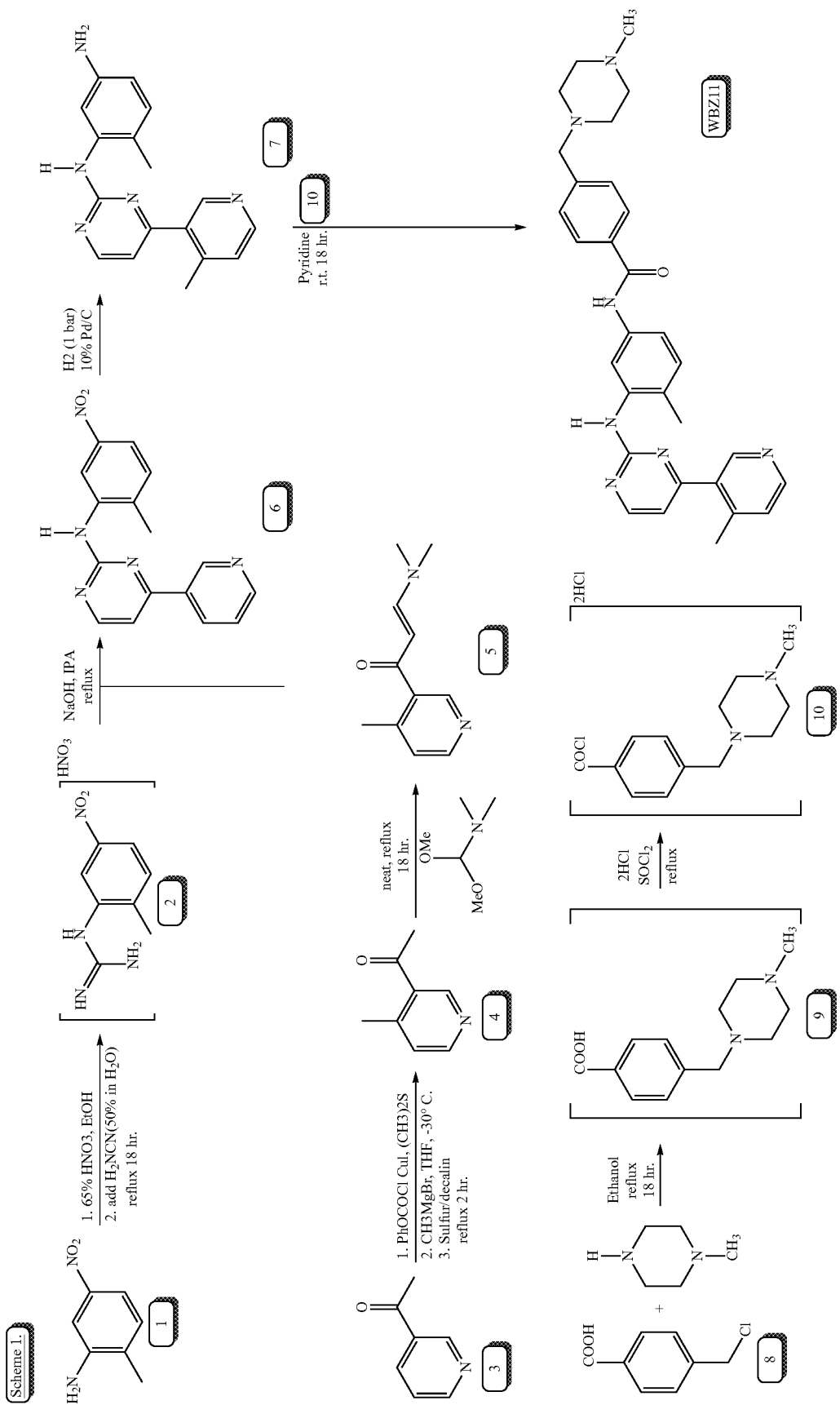

Step 1.1

Preparation of 3-acetyl-4-Methyl-pyridine (Tanis et al., 1996). A solution of 3-acetylpyridine (5 g, 41 mmol), dimethyl sulfide (20 mL, 270 mmol) and copper(I) iodide (7.94 g, 41 mmol) in anhydrous THF (100 mL) was stirred at room temperature under an Ar atmosphere for 15 minutes. Phenyl chloroformate (5.52 mL, 44 mmol) was then added dropwise in 15 minutes, producing a dark brown precipitate. After one hour, the mixture was cooled below −25° C. and methyl magnesium bromide (1.4 M in 3:1 toluene-THF, 30 mL, 42 mmol) was added over one hour, keeping the reaction temperature below −20° C. The color lightened as the mixture became a solution; a lime green precipitate formed near the end of the addition, but redissolved upon completion. The mixture was stirred and allowed to warm slowly; after 2 hours it had warmed to room temperature. Saturated aqueous $NH_4Cl$ solution (25 mL) was added; after stirring 10 minutes, the mixture was poured into a separatory funnel containing water (25 mL). The organic phase was separated, washed with brine (50 mL), dried ($Na_2SO_4$), filtered, and then concentrated in vacuum. The residue was purified by silica gel chromatography using a 5-30% EtOAc-hexane to afford 6.22 g (24 mmol, 57%) of the intermediate dihydropyridine: TLC Rf=0.12 (20% EtOAc/hexane); MS: 258.0 (M+H); $^1$H NMR (CDCl$_3$) δ 7.92 (s, 1H), 7.41 (t, J=7.70 Hz, 2H), 7.28 (t, J=7.70 Hz, 1H), 7.19 (d, J=7.70 Hz, 2H), 6.85 (m, 1H), 5.24 (m, 1H), 3.45 (m, 1H), 2.33 (s, 3H). 1.15 (d, J=6.89 Hz, 3H); $^{13}$C NMR δ 196.71, 150.39, 133.43, 129.64 (2C), 126.44 (2C), 121.31, 120.45, 119.92, 115.80, 26.31, 23.20, 21.04.

Step 1.2.

A solution of the intermediate dihydropyridine (6.22 g, 24 mmol) was added to a stirred suspension of sulfur (0.77 g, 24 mmol) in decalin and slowly heated to 160° C. under an argon sweep. After refluxing 5 h, the mixture was allowed to cool to room temperature, then filtered through a pad of silica gel. After eluting the decalin with hexane, elution with a hexane-EtOAc gradient afforded 1.2 g (40%) of 3-acetyl-4-Methyl-pyridine as a reddish-brown oil: TLC Rf 0.14 (1:1 hexane/EtOAc); MS: 136.4 (M+H); $^1$H NMR (CDCl$_3$) δ 8.96 (s, 1H), 8.5 (d, J=5.1 Hz, 1H), 7.2 (d, J=5.1 Hz, 1H), 2.64 (s, 3H), 2.57 (s, 3H); $^{13}$C NMR δ 199.53, 151.84, 150.51, 148.03, 132.95, 126.86, 29.37, 21.17.

Step 1.1 and 1.2

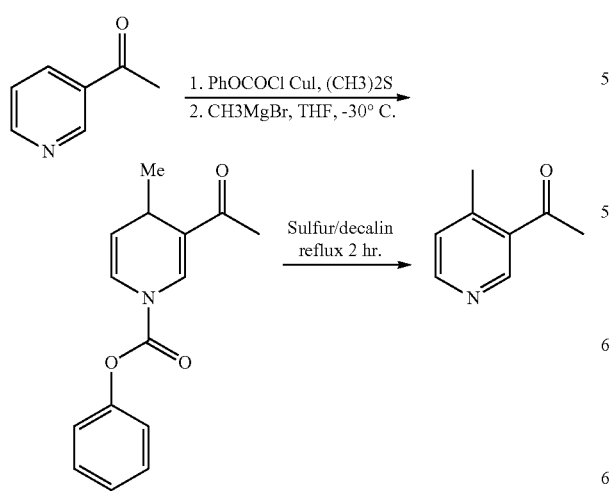

Step 1.3.

3-Acetyl-4-methyl-pyridine (1.2 g, 8.8 mmol) was added to dimethylformamide dimethylacetal (3 ml, 22 mmol), and the mixture was reacted under reflux for 18 hours. After the reaction mixture was cooled to 0° C., the solution was evaporated to dryness and a mixture of diethyl ether and hexane (3:2, v/v) (10 ml) was added and the whole mixture was stirred for 4 hours. The resulting solid was filtered and washed with a mixture of diethyl ether and hexane (10 ml, 3/2, v/v) to give 3-dimethylamino-1-(3-(4-methyl-pyridyl))-2-propen-1-one (1.5 g, 8 mmol, 90%) (U.S. Pat. No. 4,623,486). Rf=0.46 (Methylene chloride:Methanol=9:1). MS: 191.2 (M+H); $^1$H NMR (CDCl$_3$) δ 8.55 (s, 1H), 8.44 (d, J=4.8 Hz, 1H), 7.1-8.0 (br, 1H), 7.13 (d, J=4.8 Hz, 1H), 5.37 (d, J=12.7 Hz, 1H), 3.11 (s, 3H), 2.88 (s, 3H), 2.42 (s, 3H); $^{13}$C NMR δ 191.07, 155.23, 148.42, 147.87, 145.37, 137.01, 125.60, 97.09, 45.16, 36.48, 19.44.

Step 1.3

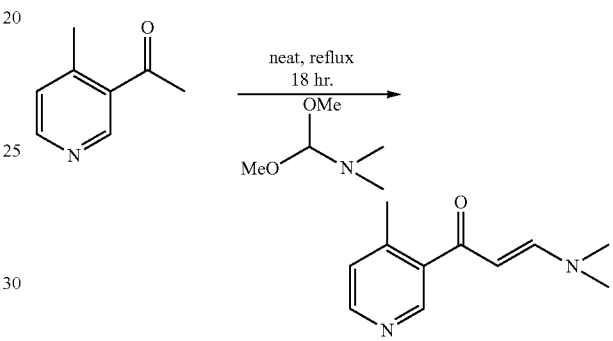

Step 1.4

2.Methyl-5-nitroaniline (100 g, 0.657 mol) was dissolved in ethanol (250 ml), and 65% aqueous nitric acid solution (48 ml, 0.65 mol) was added thereto. When the exothermic reaction was stopped, cyanamide (41.4 g) dissolved in water (41.4 g) was added thereto. The brown mixture was reacted under reflux for 24 hours. The reaction mixture was cooled to 0° C., filtered, and washed with ethanol:diethyl ether (1:1, v/v) to give 2-methyl-5-nitrophenyl-guanidine nitrate (98 g) (U.S. Pat. No. 4,623,486). Rf=0.1 (Methylene chloride:Methanol: 25% Aqueous ammonia=150:10:1). MS: 195.2 (M+H); $^1$H-NMR (DMSO-d$_6$)=1.43 (s, 3H), 6.59 (s, 3H), 6.72-6.76 (d, 1H), 7.21-7.27 (m, 1H), 8.63-8.64 (br, 1H).

Step 1.4

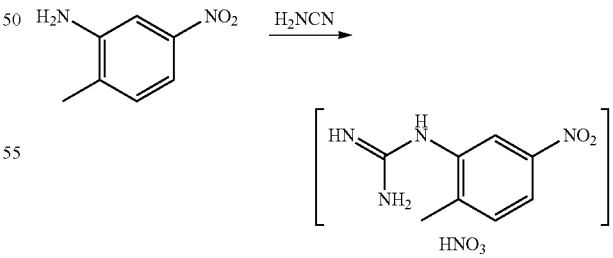

Step 1.5

3-dimethylamino-1-(3-(4-methyl-pyridyl))-2-propen-1-one (1.5 g, 8 mmol), 2-methyl-5-nitrophenyl-guanidine nitrate (2 g, 8 mol), and sodium hydroxide (350 mg, 9 mmol) were dissolved in isopropanol 100 ml and reacted under reflux for 18 hours. The reaction solution was cooled to 0° C., filtered, washed with isopropanol and methanol, and dried to give N-(2-methyl-5-nitrophenyl)-4-(4-methyl-pyridyl))-2-pyrimidine-amine. The crude product residue was purified by silica gel chromatography using a linear gradient EtOAc-hexane to afford the product (U.S. Pat. No. 4,623,486). TLC Rf=0.1 (50% EtOAc/hexane), Rf=0.6 (Methylene chloride: Methanol=9:1). MS 322.5 (M+H).

Step 1.5

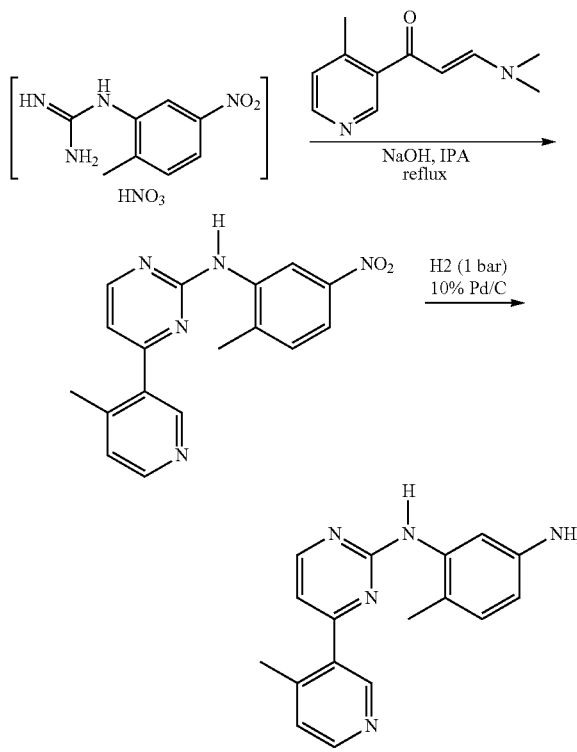

Step 1.6

The above N-(2-methyl-5-nitrophenyl)-4-(4-methyl-pyridyl))-2-pyrimidine-amine fractions after HPLC were subjected to hydrogenation with 10% Palladium on active carbon 200 mg at atmosphere for 18 hour. The solution were filtered through Whatman 0.45 μm PTFE Glass filter and the solvent were evaporated to give N-(2-methyl-5-aminophenyl)-4-(4-methyl-pyridyl))-2-pyrimidine-amine (250 mg). MS: 292.2 (M+H); $^1$H NMR (CDCl$_3$) δ 8.62 (d, 1H), 8.45 (t, 1H), 8.41 (t, 1H), 7.43 (t, 1H), 7.32 (t, 1H), 7.14 (t, 1H), 6.92 (m, 1H), 6.77 (m, 1H), 6.34 (m, 1H), 2.42 (s, 3H), 2.15 (s, 3H); $^{13}$C NMR δ 165.13, 160.52, 158.62, 149.81, 149.61, 145.54, 145.23, 137.82, 134.27, 130.99, 125.87, 118.65, 111.94, 110.97, 109.07, 20.05, 17.18.

Step 1.7.

To a well-stirred suspension consisting of 17.1 g. (0.10 mole) of α-chloro-p-toluylic acid in 150 ml of absolute ethanol under a nitrogen atmosphere at room temperature (~20° C.) a solution consisting of 44.1 g. (0.44 mole) of N-methylpiperazine dissolved in 50 ml of ethanol was added dropwise. The resulting reaction mixture was refluxed for a period of 16 hours and then cooled to room temperature. The cooled reaction mixture was concentrated in vacuo and the thus obtained residue partitioned between 100 ml of diethyl ether and 100 ml of 3N aqueous sodium hydroxide. The separated aqueous layer was then washed three times with 100 ml of diethyl ether, cooled in an ice-water bath and subsequently acidified with concentrated hydrochloric acid. The resulting solids were filtered and air-dried, followed by trituration with 150 ml of boiling isopropyl alcohol and stirring for a period of two minutes. After filtering while hot and drying the product there were obtained 9.4 g. (35%) of pure 4-(4-methylpiperazinomethyl)benzoic acid dihydrochloride as the hemihydrate, m.p. 310°-312° C. MS: 235.1 (M+H); $^1$H NMR (D$_2$O) δ 8.04 (d, J=8.21 Hz, 2H), 7.59 (d, J=8.21 Hz, 2H), 3.50 (s, 2H), 3.63 (br, 8H), 2.97 (s, 3H); $^{13}$C NMR δ 170.18, 133.13, 131.91, 130.90, 60.22, 50.61, 48.77, 43.25.

Step 1.7

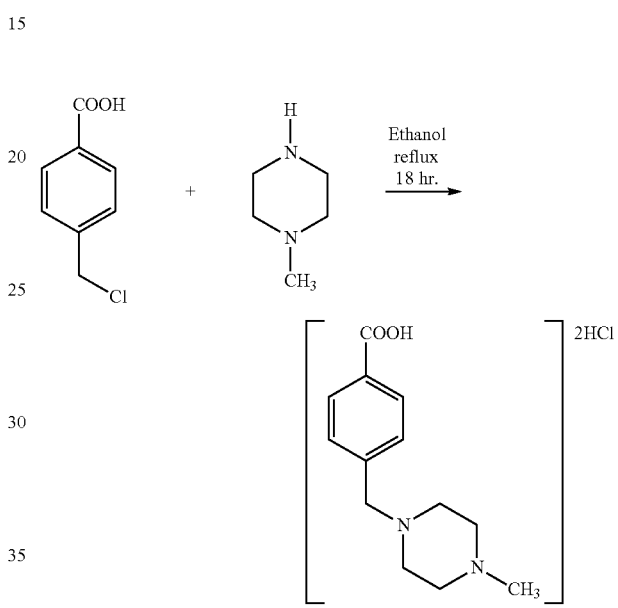

Step 1.8

To 20 g. (0.065 mole) of 4-(4-methyl-piperazin-1-ylmethyl)-benzoic acid dihydrochloride under a nitrogen atmosphere, there were added 119 ml of thionyl chloride (194 g., 1.625 mole) to form a beige-white suspension. The reaction mixture was refluxed for 24 hours and then cooled to room temperature (~20° C.). The resulting suspension was filtered, and the recovered solids were washed with diethyl ether and dried to ultimately afford 17.0 g (81%) of pure 4-(4-methylpiperazin-1-ylmethyl)-benzoyl chloride dihydrochloride.

Step 1.8

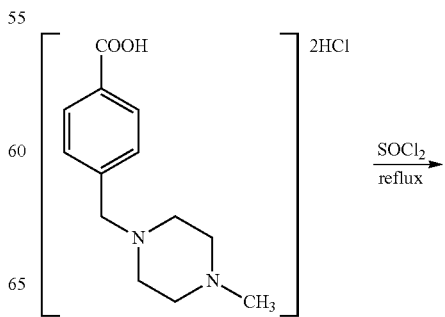

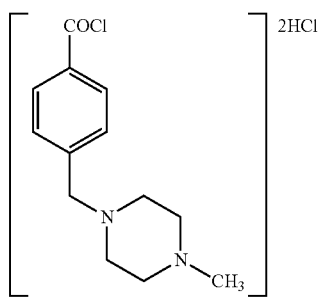

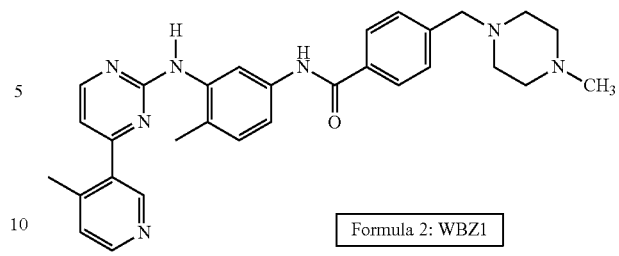

Formula 2: WBZ1

Step 1.9

Preparation of N-{5-[4-(4-methyl piperazine methyl)-benzoylamido]-2-methylphenyl}-4-[3-(4-methyl)-pyridyl]-2-pyrimidine amine (free base) (WBZ1). A mixture of 250 mg (0.85 mmol) N-(2-methyl-5-aminophenyl)-4-(4-methyl-pyridyl))-2-pyrimidine-amine from step 1.6 and 325 mg (1 mmol) 4-(4-methylpiperazinomethyl)benzoyl chloride dihydrochloride from step 1.8 were stirred in 20 ml anhydrous pyridine at 20° C. for 18 hours. The reaction mixture was concentrated in vacuum. The residue was subjected to silica gel chromatography using 5% Methanol (7M NH$_3$) in DCM. MS: 508.4 (M+H); $^1$H NMR (DMSO) δ 10.14 (s, 1H), 9.00 (s, 1H), 8.61 (s, 1H), 8.47 (dd, J=4.8, 1.6 Hz, 1H), 7.94 (s, 1H), 7.89 (d, J=7.7 Hz, 2H), 7.48 (dd, J=8.24, 2.1 Hz, 1H), 7.43 (d, J=8.61 Hz, 2H), 7.31 (d, J=5.0 Hz, 1H), 7.18 (d, J=8.24, 1H), 7.19 (dd, J=4.9, 1.1 Hz, 1H), 3.52 (s, 2H), 2.50 (s, 8H), 2.38 (s, 3H), 2.20 (s, 3H), 2.14 (s, 3H); $^{13}$C NMR δ 165.18, 164.23, 161.16, 158.72, 149.69, 149.32, 145.05, 142.10, 137.75, 137.17, 133.89, 133.69, 129.97, 128.61, 128.16, 127.53, 125.75, 117.88, 116.95, 111.31, 61.59, 54.68, 52.56, 45.73, 19.60, 17.57.

Step 1.9

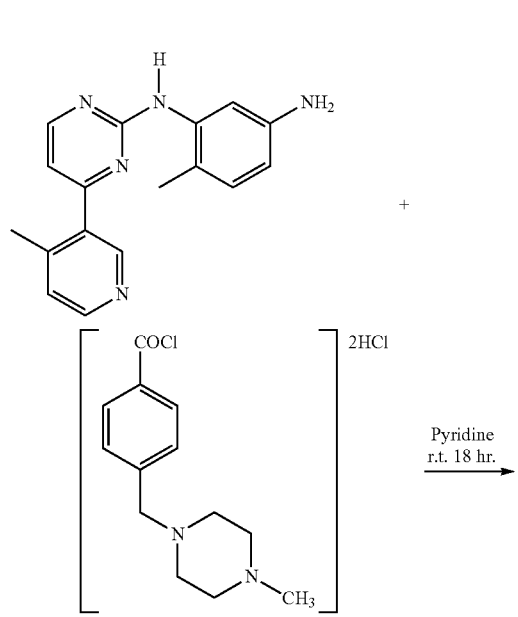

C. Synthesis of WBZ2

Preparation of Intermediate 3-acetyl-4-Ethyl-pyridine. Following the procedure of step 1.1, but substitute methyl magnesium bromide for ethyl magnesium bromide, the intermediate dihydropyridine was obtained as a solid. 4.63 g (17 mmol, 42%). TLC Rf=0.12 (20% EtOAc/hexane); MS: 272.2 (M+H); $^1$H NMR (CDCl$_3$) δ 7.98 (s, 1H), 7.41 (t, J=7.70 Hz, 2H), 7.28 (t, J=7.70 Hz, 1H), 7.19 (d, J=7.70 Hz, 2H), 6.85 (m, 1H), 5.24 (m, 1H), 3.45 (m, 1H), 2.33 (s, 3H). 1.55 (m, 2H), 0.86 (m, 3H); $^{13}$C NMR δ 196.77, 150.40, 134.23, 129.64 (2C), 126.43 (2C), 121.62, 121.31, 115.38, 113.41, 32.18, 28.41, 25.27, 9.43.

Following the procedure of step 1.2 (step 2.2), 3-acetyl-4-ethyl-pyridine was obtained as an orange oil. 1.8 g (12 mmol, 70%). TLC Rf 0.14 (1:1 hexane/EtOAc); MS: 150.2 (M+H); $^1$H NMR (CDCl$_3$) δ 8.94 (s, 1H), 8.59 (t, J=5.1 Hz, 1H), 7.25 (t, J=5.1 Hz, 1H), 2.92 (m, 2H), 2.66 (s, 3H), 1.23 (t, 3H); $^{13}$C NMR δ 199.78, 153.37, 152.57, 150.18, 132.95, 124.85, 29.65, 26.43, 14.49.

Step 2.2

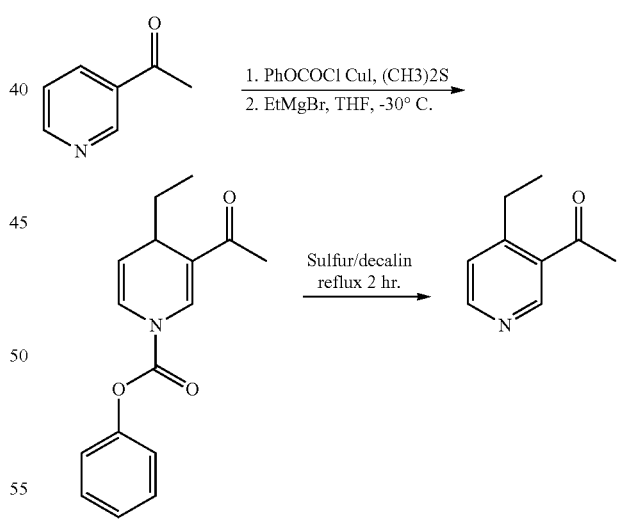

Following the procedure of step 1.3, but substituting 3-acetyl-4-methyl-pyridine for 3-acetyl-4-ethyl-pyridine, the title compound was obtained as a solid. (2 g, 90%). Rf=0.46 (Methylene chloride:Methanol=9:1). MS: 205.3 (M+H); 1H NMR (CDCl3) δ 8.48 (s, 1H), 8.47 (d, J=4.8 Hz, 1H), 7.1-8.0 (br, 1H), 7.18 (d, J=4.8 Hz, 1H), 5.37 (d, J=12.7 Hz, 1H), 3.10 (s, 3H), 2.86 (s, 3H), 2.00 (br, 2H), 5.37 (t, J=5.2 Hz, 3H); $^{13}$C NMR δ 191.24, 155.21, 150.93, 149.83, 147.82, 137.51, 124.05, 97.41, 45.11, 36.88, 25.88, 14.10.

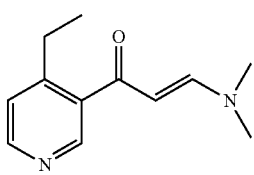

3-dimethylamino-1-(3-(4-Ethyl-pyridyl))-2-propen-1-one

Following the procedure of step 1.5 and 1.6, but substituting 3-dimethylamino-1-(3-(4-methyl-pyridyl))-2-propen-1-one for 3-dimethylamino-1-(3-(4-Ethyl-pyridyl))-2-propen-1-one, the title compound was obtained as a solid. MS: 306.2 (M+H); $^1$H NMR (DMSO) δ 8.48 (d, J=3.0 Hz, 1H), 8.42 (t, J=4.8 Hz, 1H), 8.34 (t, J=4.8 Hz, 1H), 7.29 (s, 1H), 7.26 (s, 1H), 7.10 (t, J=4.8 Hz, 1H), 6.83 (dd, J=8.0, 2.7 Hz, 1H), 6.66 (t, J=4.8 Hz, 1H), 6.26 (d, J=8.9 Hz, 1H), 2.70 (q, 2H), 2.10 (s, 3H), 1.04 (t, 3H). $^{13}$C NMR δ 165.34, 160.58, 158.48, 151.23, 150.26, 149.65, 145.30, 137.84, 134.00, 130.99, 123.86, 118.76, 111.93, 111.02, 109.22, 25.53, 21.03, 14.63.

Preparation of N-(2-methyl-5-aminophenyl)-4-(4-ethyl-pyridyl))-2-pyrimidine-amine. Following the procedure of Example 1, step 1.9, but substitute N-(2-methyl-5-aminophenyl)-4-(4-methyl-pyridyl))-2-pyrimidine-amine for N-(2-methyl-5-aminophenyl)-4-(4-ethyl-pyridyl))-2-pyrimidine-amine, the title compound was obtained as a solid. MS: 522.5 (M+H); $^1$H NMR (DMSO) δ 8.53 (s, 1H), 8.45 (d, 2H), 8.03 (d, 1H), 7.77 (d, J=8.1 Hz, 2H), 7.44 (m, 4H), 7.35 (d, J=5.1 Hz, 1H), 7.21 (d, J=8.1 Hz, 1H), 6.91 (d, J=5.1 Hz, 1H), 3.58 (s, 2H), 3.38 (s, 3H), 2.83 (q, 2H), 2.50 (br, 8H), 2.28 (s, 6H), 1.10 (t, 3H) $^{13}$C NMR δ 168.38, 166.60, 162.63, 159.96, 154.09, 150.51, 150.09, 142.90, 138.29, 135.82, 135.36, 131.66, 131.16, 130.83, 129.29, 128.73, 125.77, 119.37, 119.26, 112.77, 63.31, 55.75, 53.62, 46.06 26.77, 17.95, 14.97.

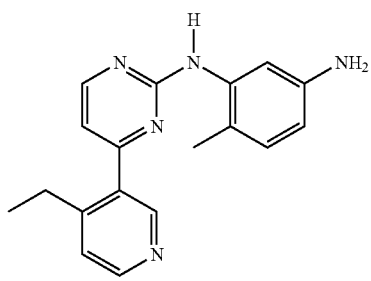

N-(2-methyl-5-aminophenyl)-4-(4-ethyl-pyridyl))-2-pyrimidine-amine

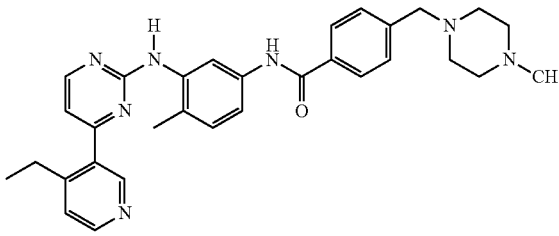

Formula 3 - WBZ2

D. Synthesis of WBZ3

Preparation of Intermediate: 4-(2-Propyl)-3-acetylpyridine. Following the procedure of step 1.1, but substitute methyl magnesium bromide for isopropyl magnesium chloride, the intermediate dihydropyridine was obtained as a solid. 4.65 g (16 mmol, 40%). TLC Rf=0.12 (20% EtOAc/hexane); MS: 286.3 (M+H); $^1$H NMR (CDCl$_3$) δ 8.00 (s, 1H), 7.41 (t, J=7.70 Hz, 2H), 7.28 (t, J=7.70 Hz, 1H), 7.19 (d, J=7.70 Hz, 2H), 7.04 (m, 1H), 5.20 (m, 1H), 3.46 (m, 1H), 2.34 (s, 3H). 1.93 (m, 1H), 0.95 (dd, J=2.41, 1.34 Hz, 3H), 0.77 (dd, J=2.41, 1.34 Hz, 3H); $^{13}$C NMR δ 196.80, 150.40, 134.29, 129.64 (2C), 126.43 (2C), 122.66, 121.32, 115.38, 110.54, 37.23, 31.57, 25.34, 19.46, 17.05.

Following the procedure of step 1.2 (step 3.2), 4-(2-Propyl)-3-acetylpyridine was obtained as an orange oil. 1.1 g (6 mmol, 42%). TLC Rf 0.14 (1:1 hexane/EtOAc); MS: 164.4 (M+H); $^1$H NMR (CDCl$_3$) δ 8.80 (s, 1H), 8.59 (t, J=5.1 Hz, 1H), 7.35 (t, J=5.1 Hz, 1H), 3.59 (m, 1H), 2.63 (s, 3H), 1.23 (m, 6H); $^{13}$C NMR δ 200.95, 157.36, 151.89, 149.27, 133.72, 121.42, 30.46, 28.87, 23.19 (2C).

Step 3.2

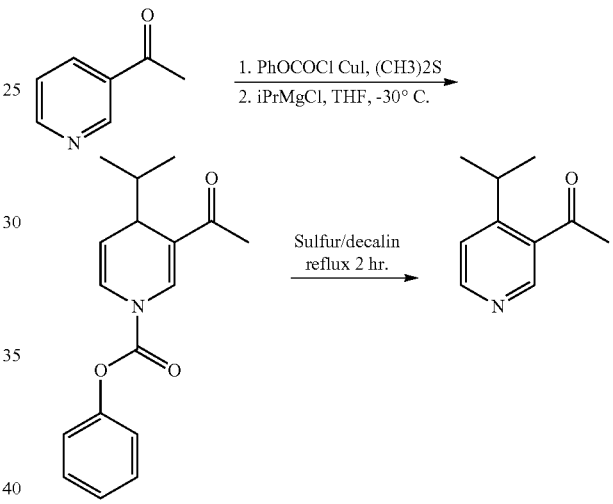

Preparation of 3-dimethylamino-1-(3-(4-(2-Propyl)-pyridyl))-2-propen-1-one. Following the procedure of step 1.3, but substitute 3-Acetyl-4-methyl-pyridine for 3-Acetyl-4-(2-Propyl)-pyridine, the title compound was obtained as a solid. (1.5 g, 90%). Rf=0.46 (Methylene chloride:Methanol=9:1). MS: 219.0 (M+H); 1H NMR (CDCl3) δ 8.50 (d, J=5.3 Hz, 1H), 8.48 (s, 1H), 7.1-8.0 (br, 1H), 7.26 (d, J=5.3 Hz, 1H), 5.35 (d, J=12.4 Hz, 1H), 3.44 (br, 1H), 3.10 (s, 3H), 2.89 (s, 3H), 1.24 (d, 6H); $^{13}$C NMR δ 191.93, 162.51, 155.44, 149.81, 147.68, 137.51, 120.86, 96.08, 44.68, 36.80, 29.02, 23.50 (2C).

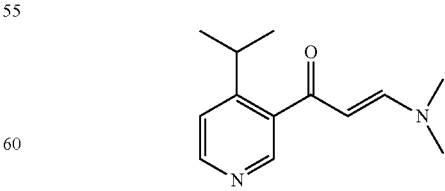

3-dimethylamino-1-(3-(4-(2-Propyl)-pyridyl))-2-propen-1-one

Preparation of N-(2-methyl-5-aminophenyl)-4-(2-Propyl)-pyridyl))-2-pyrimidine-amine. Following the procedure of Example 1, step 1.5 and 1.6, but substitute 3-dimethylamino-1-(3-(4-methyl-pyridyl))-2-propen-1-one for 3-dimethylamino-1-(3-(4-(2-Propyl)-pyridyl))-2-propen-1-one, the title compound was obtained as a solid. MS: 320.4 (M+H); $^1$H NMR (CDCl$_3$) δ 8.61 (d, J=5.3 Hz, 1H), 8.56 (d, J=4.8 Hz, 1H), 8.49 (t, J=5.1 Hz, 1H), 7.51 (t, 1H), 7.32 (t, J=5.0 Hz, 1H), 7.10 (t, 1H), 6.98 (m, 1H), 6.80 ((t, J=2.1 Hz, 1H), 6.39 (m, 1H), 3.41 (m, 1H), 2.22 (s, 3H), 1.23 (m, 6H); $^{13}$C NMR δ 165.60, 160.41, 158.40, 155.82, 150.32, 149.70, 145.20, 137.86, 134.27, 133.67, 131.02, 120.90, 118.29, 112.47, 110.78, 108.67, 28.93, 23.40, 17.21.

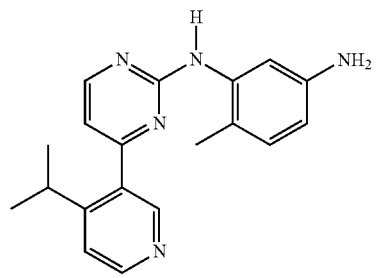

N-(2-methyl-5-aminophenyl)-4-(2-Propyl)-pyridyl))-2-pyrimidine-amine

Preparation of N-{5-[4-(4-methyl piperazine methyl)-benzoylamido]-2-methylphenyl}-4-[3-(4-(2-Propyl)-pyridyl)]-2-pyrimidine amine (free base). Following the procedure of Example 1, step 1.9, but substitute N-(2-methyl-5-aminophenyl)-4-(4-methyl-pyridyl))-2-pyrimidine-amine for N-(2-methyl-5-aminophenyl)-4-(2-Propyl)-pyridyl))-2-pyrimidine-amine, the title compound was obtained as a solid. MS: 536.5 (M+H); $^1$H NMR (CD$_3$OD) δ 8.52 (d, J=5.3 Hz, 1H), 8.48 (d, 1H), 8.48 (dd, J=5.1, 2.1 Hz, 1H), 8.02 (s, 1H), 7.90 (d, J=8.1 Hz, 2H), 7.50 (m, 4H), 7.46 (d, J=5.1 Hz, 1H), 7.26 (d, J=8.1 Hz, 1H), 6.91 (d, J=5.1 Hz, 1H), 3.63 (s, 2H), 3.45 (m, 1H), 2.50 (br, 8H), 2.30 (s, 6H), 1.19 (s, 3H), 1.18 (s, 3H). $^{13}$C NMR δ 169.40, 165.48, 163.89, 159.66, 156.98, 155.64, 147.68, 147.09, 139.94, 135.98, 135.29, 132.60, 132.40, 128.67, 127.80, 127.64, 127.42, 125.73, 125.22, 119.77, 116.50, 116.40, 110.04, 60.34, 52.00, 50.61, 43.60, 27.38, 23.80, 14.91.

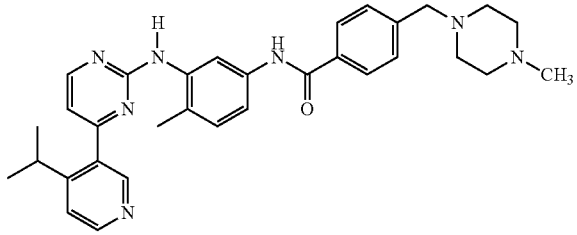

Formula 4 - WBZ3

E. Synthesis of WBZ4

The synthesis of WBZ4, as shown in scheme 3 below, begins with treatment of 2-methyl-5-nitroaniline (1) with 65% nitric acid in ethanol followed by the addition of cyanoamide to give the corresponding 2-methyl-5-nitroaniline-guanidine nitrate (2). Once completed, nicotinate (3) was first treated with sodium hydrate and refluxed with ethyl acetate to form methyl 6-methylnicotinylacetate. The intermediate acetate was then hydrolyzed to form 3-Acetyl-6-methylpyridine (4). The product (4) was treated with methyl dimethoxyforamide to give 3-dimethylamino-1-(3-(6-methyl-pyridyl)-2-propene-1-one (5). The nitrate salt (2) is treated with (5) and sodium hydroxide in refluxing isopropanol to give N-(2-Methyl-5-nitrophenyl)-4-(3-(6-methyl-pyridyl))-2-pyrimidine-amine (6) which is subsequently hydrogenated with 10% palladium on carbon to give N-(2-Methyl-5-aminophenyl)-4-(3-6-methyl-pyridyl)-2-pyrimidine-amine (7). The WBZ4 synthesis will consist of the reaction of α-chloro-p-toluylic acid (8) with 4-methyl-piperazine in ethanol followed by treatment with concentrated HCl to give the corresponding dihydrochloride 4-(4-methyl-piperazin-1-ylmethyl)-benzoic acid (9) which is subsequently treated with thionyl chloride to give the corresponding acid chloride dihydrochloride (10). Subsequent condensation with N-(2-Methyl-5-aminophenyl)-4-(3-(6-methyl)-pyridyl)-2-pyrimidine-amine (7) in pyridine affords Formula 5 (WBZ4).

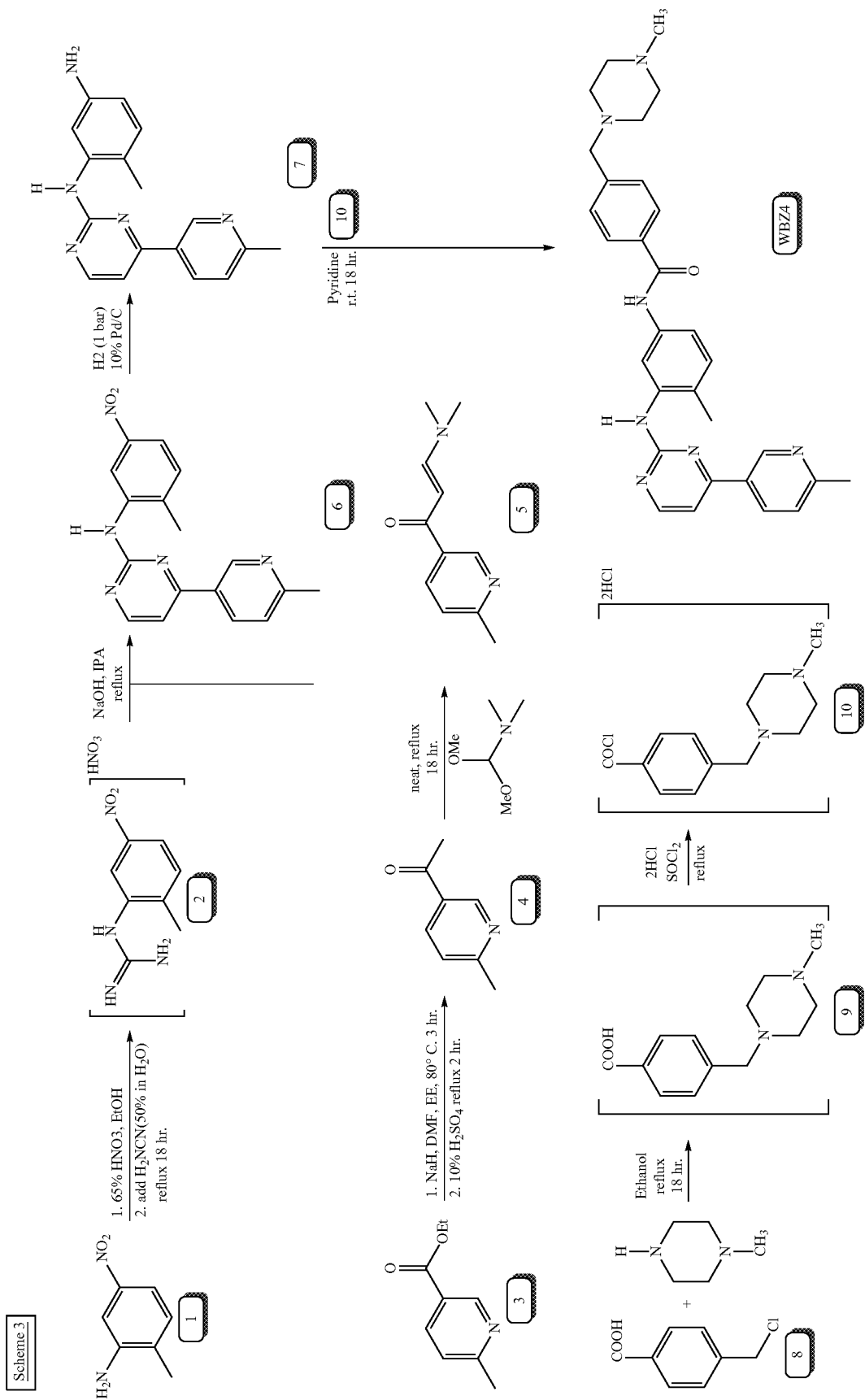

2-Methyl-5-nitroaniline (100 g, 0.657 mol) was dissolved in ethanol (250 ml), and 65% aqueous nitric acid solution (48 ml, 0.65 mol) was added thereto. When the exothermic reaction was stopped, cyanamide (41.4 g) dissolved in water (41.4 g) was added thereto. The brown mixture was reacted under reflux for 24 hours. The reaction mixture was cooled to 0° C., filtered, and washed with ethanol:diethyl ether (1:1, v/v) to give 2-methyl-5-nitrophenyl-guanidine nitrate (2) (98 g). Rf=0.1 (Methylene chloride:Methanol:25% Aqueous ammonia=150:10:1). MS: 195.2 (M+H); $^1$H-NMR (DMSO-$d_6$)=1.43 (s, 3H), 6.59 (s, 3H), 6.72-6.76 (d, 1H), 7.21-7.27 (m, 1H), 8.63-8.64 (br, 1H).

To a suspension of sodium hydride (5.2 g of a 60%, w/w, oil dispersion, 66 mmol) in toluene (80 mL) and N,N-dimethylformamide (6.6 mL) was added approximately 10% of a solution of methyl 5-methyl-nicotinate (3) (10 g, 66 mmol) in ethyl acetate (14 mL), and the mixture was heated at 80° C. for 30 min. The remainder of the solution was added slowly over 2 h while maintaining an internal temperature of approximately 80° C. After cooling to room temperature, the reaction mixture was diluted with water (100 ml) and thoroughly extracted with ethyl acetate (3×100 ml) and methylene chloride (2×100 ml). The combined organic extracts were evaporated in vacuo, and the residue was heated under reflux in 10% (v/v) sulfuric acid (30 mL) for 2 h. After cooling to 0° C., the reaction mixture was neutralized with solid $K_2CO_3$ and extracted with ethyl acetate (200 ml). The organic extract was dried ($Na_2SO_4$), filtered, and evaporated in vacuo to give the crude ketone as a red-orange viscous liquid. 3-Acetyl-6-methyl-pyridine (4) was purified with a gradient of 0-100% EtOAc in hexane to afford the desired methylketone as a clear, pale yellow, viscous liquid. 1.5 g (10 mmol, 17%). TLC ($R_f$=0.16; MS: 136.0 (M+H); $^1$H-NMR (DMSO) δ 9.05 (d, J=2.2 Hz, 1), 8.13 (dd, J=8.1, 2.2 Hz, 1), 7.27 (d, J=8.1 Hz, 1), 2.64 (s, 3), 2.62 (s, 3). $^{13}$C NMR δ 197.48, 163.20, 149.62, 136.24, 130.06, 123.56, 27.23, 24.70.

3-Acetyl-6-methyl-pyridine (4) (1.2 g, 8.8 mmol) was added to dimethylformamide dimethylacetal (3 ml, 22 mmol), and the mixture was reacted under reflux for 18 hours. After the reaction mixture was cooled to 0° C. The solution was evaporated to dryness and a mixture of diethyl ether and hexane (3:2, v/v) (10 ml) was added and the whole mixture was stirred for 4 hours. The resulting solid was filtered and washed with a mixture of diethyl ether and hexane (10 ml, 3/2, v/v) to give 3-dimethylamino-1-(3-(4-methyl-pyridyl))-2-propen-1-one (5) (1.5 g, 8 mmol, 90%). $R_f$=0.46 (Methylene chloride:Methanol=9:1). MS: 191.1 (M+H); $^1$H NMR (DMSO) δ 8.90 (s, 1H), 8.16 (d, J=7.9 Hz, 1H), 7.85 (d, J=12.0 Hz, 1H), 7.35 (d, J=8.0 Hz, 1H), 5.85 (d, J=12.0 Hz, 1H), 3.18 (s, 3H), 2.95 (s, 3H), 2.58 (s, 3H); $^{13}$C NMR δ 183.38, 158.91, 153.78, 146.11, 135.85, 131.45, 121.77, 89.36, 42.78, 34.00, 21.40.

3-dimethylamino-1-(3-(6-methyl-pyridyl))-2-propen-1-one (5) (1.5 g, 8 mmol), 2-methyl-5-nitrophenyl-guanidine nitrate (2) (2 g, 8 mol), and sodium hydroxide (350 mg, 9 mmol) were dissolved in isopropanol 100 ml and reacted under reflux for 18 hours. The reaction solution was cooled to 0° C., filtered, washed with isopropanol and methanol, and dried to give N-(2-methyl-5-nitrophenyl)-4-(6-methyl-pyridyl))-2-pyrimidine-amine (6). The residue was purified by silica gel chromatography using a linear gradient EtOAc-hexane to afford the product. TLC Rf=0.1 (50% EtOAc/hexane) $R_f$=0.6 (Methylene chloride:Methanol=9:1). MS 322.5 (M+H).

The above N-(2-methyl-5-nitrophenyl)-4-(6-methyl-pyridyl))-2-pyrimidine-amine (6) fractions, after flash chromatography, were subjected to hydrogenation with 10% Palladium on active carbon 200 mg at atmosphere for 18 hour. The solution was filtered through Whatman 0.45 μm PTFE Glass filter and the solvent were evaporated to give N-(2-methyl-5-aminophenyl)-4-(6-methyl-pyridyl))-2-pyrimidine-amine (7) (250 mg). MS: 292.2 (M+H); $^1$H NMR (CDCl$_3$) δ 8.62 (d, 1H), 8.45 (t, 1H), 8.41 (t, 1H), 7.43 (t, 1H), 7.32 (t, 1H), 7.14 (t, 1H), 6.92 (m, 1H), 6.77 (m, 1H), 6.34 (m, 1H), 2.42 (s, 3H), 2.15 (s, 3H); $^{13}$C NMR δ 165.13, 160.52, 158.62, 149.81, 149.61, 145.54, 145.23, 137.82, 134.27, 130.99, 125.87, 118.65, 111.94, 110.97, 109.07, 20.05, 17.18.

To a well-stirred suspension consisting of 17.1 g. (0.10 mole) of α-chloro-p-toluylic acid in 150 ml of absolute ethanol under a nitrogen atmosphere at room temperature (~20° C.), a solution consisting of 44.1 g. (0.44 mole) of N-methylpiperazine dissolved in 50 ml. of ethanol was added dropwise. The resulting reaction mixture was refluxed for a period of 16 hours and then cooled to room temperature. The cooled reaction mixture was concentrated in vacuo and the thus obtained residue partitioned between 100 ml of diethyl ether and 100 ml of 3N aqueous sodium hydroxide. The separated aqueous layer was then washed three times with 100 ml of diethyl ether, cooled in an ice-water bath and subsequently acidified with concentrated hydrochloric acid. The resulting solids were filtered and air-dried, followed by trituration with 150 ml of boiling isopropyl alcohol and stirring for a period of two minutes. After filtering while hot and drying the product there were obtained 9.4 g (35%) of pure 4-(4-methylpiperazinomethyl)benzoic acid dihydrochloride (9) as the hemihydrate, m.p. 310°-312° C. MS: 235.1 (M+H); $^1$H NMR (D$_2$O) δ 8.04 (d, J=8.21 Hz, 2H), 7.59 (d, J=8.21 Hz, 2H), 3.50 (s, 2H), 3.63 (br, 8H), 2.97 (s, 3H); $^{13}$C NMR δ 170.18, 133.13, 131.91, 130.90, 60.22, 50.61, 48.77, 43.25.

Preparation of 4-(4-methylpiperazinomethyl)benzoyl chloride dihydrochloride (10). To 20 g. (0.065 mole) of 4-(4-methylpiperazinomethyl)benzoic acid dihydrochloride (9) under a nitrogen atmosphere, there were added 119 ml. of thionyl chloride (194 g, 1.625 mole) to form a beige-white suspension. The reaction mixture was refluxed for 24 hours and then cooled to room temperature (~20° C.). The resulting suspension was filtered, and the recovered solids were washed with diethyl ether and dried to ultimately afford 17.0 g (81%) of pure 4-(4-methylpiperazinomethyl)benzoyl chloride dihydrochloride (10).

Preparation of N-{5-[4-(4-methyl piperazine methyl)-benzoylamido]-2-methylphenyl}-4-[3-(4-methyl)-pyridyl]-2-pyrimidine amine. A mixture of N-(2-methyl-5-aminophenyl)-4-(6-methyl-pyridyl))-2-pyrimidine-amine (7) 250 mg (0.85 mmol) and 4-(4-methylpiperazinomethyl)benzoyl chloride dihydrochloride (10) 325 mg (1 mmol) were stirred in 20 ml anhydrous pyridine at 20° C. for 18 hours. The reaction mixture was concentrated in vacuum. The residue was subjected to silica gel chromatography using 5% Methanol (7M NH$_3$) in DCM. MS: 508.4 (M+H); $^1$H NMR (DMSO) δ 10.18 (s, 1H), 9.15 (d, J=2.1 Hz, 1H), 8.96 (s, 1H), 8.47 (d, J=5.1 Hz, 1H), 8.37 (dd, J=5.1, 2.1 Hz, 1H), 8.05 (d, J=2.1 Hz, 1H), 7.90 (d, J=8.61 Hz, 2H), 7.48 (dd, J=8.24, 2.1 Hz, 1H), 7.43 (d, J=8.61 Hz, 2H), 7.39 (d, J=6.0 Hz, 1H), 7.37 (d, J=5.2 Hz, 1H), 7.19 (d, 1H), 3.52 (s, 2H), 2.52 (s, 3H), 2.50 (br, 8H), 2.21 (s, 3H), 2.15 (s, 3H); $^{13}$C NMR δ 165.12, 161.61, 161.02, 160.18, 159.17, 147.48, 142.00, 137.73, 137.06, 134.50, 133.64, 129.89, 129.34, 128.51, 127.48, 122.98, 117.08, 116.55, 107.05, 61.50, 54.59, 52.48, 45.65, 23.91, 17.57.

Formula 5 (WBZ4)

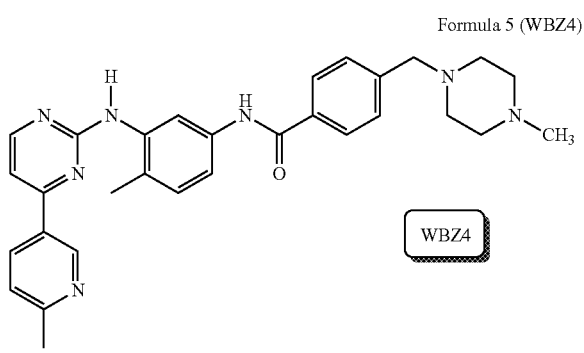 [SMILES: Cc1ccc(-c2ccnc(Nc3cc(NC(=O)c4ccc(CN5CCN(C)CC5)cc4)ccc3C)n2)cn1]

WBZ4

F. Synthesis of WBZ5

Preparation of 5-(Phenyl)-3-acetylpyridine (step 5.1). A mixture of 5-Bromo-3-acetylpyridine (2 g, 10 mmol), phenylboronic acid (1.5 g, 12 mmol), trans-dibromobis(triphenylphosphine) palladium (II) (0.4 g, 0.5 mmol), toluene (60 ml), ethanol (20 ml) and 2M aqueous sodium carbonate (40 ml) was refluxed for 1 hour under a nitrogen atmosphere. The mixture was diluted with ethyl acetate and the organic phase was washed with water and brine, dried and evaporated. The crude product was chromatographed on silica gel eluting with a gradient of 0-100% EtOAc in hexane to afford the: 5-(Phenyl)-3-acetylpyridine as a solid. 2 g (10 mmol, 100%). TLC $R_f$ 0.3 (1:1 hexane/EtOAc); MS: 198.5 (M+H); $^1$H NMR (DMSO) δ 9.12 (dd, J=2.2 Hz, 2H), 8.50 (t, J=2.1 Hz, 1H), 7.83 (d, J=8.1 Hz, 2H), 7.54 (t, J=7.7 Hz, 2H), 7.49 (t, J=7.7 Hz, 1H), 3.02 (s, 3H); $^{13}$C NMR δ 197.51, 151.30, 148.12, 136.14, 135.51, 134.05, 133.34, 132.00, 129.91, 129.78, 129.19, 127.64, 27.14.

Step 5.1

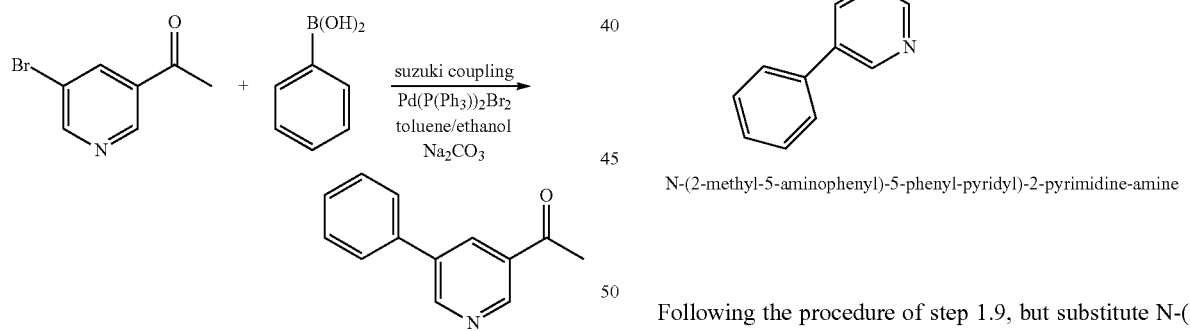

Following the procedure of step 1.3, but substituting 3-Acetyl-4-methyl-pyridine for 3-Acetyl-5-phenyl-pyridine, 5-(Phenyl)-3-acetylpyridine was obtained as a solid. (2 g, 90%). Rf=0.46 (Methylene chloride:Methanol=9:1). MS: 253.3 (M+H); $^1$H NMR (DMSO) δ 9.02 (s, 1H), 8.93 (d, H), 8.44 (d, 1H), 7.91 (d, J=12.0 Hz, 1H), 7.75 (d, J=7.1 Hz, 2H), 7.53 (t, 2H), 7.46 (d, J=7.3 Hz, 2H), 5.85 (d, J=12.0 Hz, 1H), 3.15 (s, 3H), 3.02 (s, 3H); $^{13}$C NMR δ 183.38, 162.14, 154.72, 148.22, 146.17, 136.04, 135.27, 134.87, 132.09, 128.23, 127.44, 126.13, 123.31, 90.38, 43.56, 35.90. MS: 292.2 (M+H); $^1$H NMR (CDCl$_3$) δ 8.62 (d, 1H), 8.45 (t, 1H), 8.41 (t, 1H), 7.43 (t, 1H), 7.32 (t, 1H), 7.14 (t, 1H), 6.92 (m, 1H), 6.77 (m, 1H), 6.34 (m, 1H), 2.42 (s, 3H), 2.15 (s, 3H); $^{13}$C NMR δ 165.13, 160.52, 158.62, 149.81, 149.61, 145.54, 145.23, 137.82, 134.27, 130.99, 125.87, 118.65, 111.94, 110.97, 109.07, 20.05, 17.18.

Following the procedure of step 1.5 and 1.6, but substituting 3-dimethylamino-1-(3-(4-methyl-pyridyl))-2-propen-1-one for 3-dimethylamino-1-(3-(5-phenyl-pyridyl))-2-propen-1-one, the 3-dimethylamino-1-(3-(5-phenyl-pyridyl))-2-propen-1-one (was obtained as a solid. MS: 355.5 (M+H).

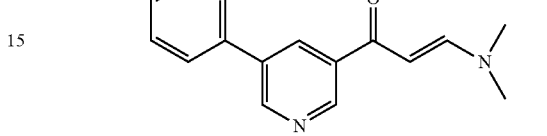

3-dimethylamino-1-(3-(5-phenyl-pyridyl))-2-propen-1-one

Following the procedure of step 1.5 and 1.6, but substituting 3-dimethylamino-1-(3-(4-methyl-pyridyl))-2-propen-1-one for 3-dimethylamino-1-(3-(5-phenyl-pyridyl))-2-propen-1-one, N-(2-methyl-5-aminophenyl)-5-phenyl-pyridyl)-2-pyrimidine-amine was obtained. MS: 355.5 (M+H)

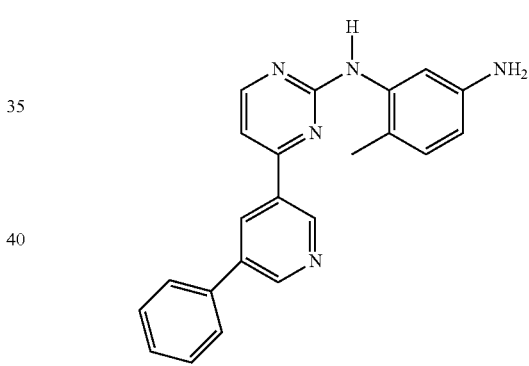

N-(2-methyl-5-aminophenyl)-5-phenyl-pyridyl)-2-pyrimidine-amine

Following the procedure of step 1.9, but substitute N-(2-methyl-5-aminophenyl)-4-(4-methyl-pyridyl))-2-pyrimidine-amine for N-(2-methyl-5-aminophenyl)-5-phenyl-pyridyl)-2-pyrimidine-amine, N-{5-[4-(4-methyl piperazine methyl)-benzoylamido]-2-methylphenyl}-4-[3-(5-phenyl)-pyridyl]-2-pyrimidine amine (Formula 6) was obtained as a solid. MS: 570.4 (M+H); $^1$H NMR (DMSO) δ 10.20 (s, 1H), 9.28 (s, 1H), 9.04 (s, 1H), 9.00 (s, 1H), 8.71 (s, 1H), 8.56 (s, 1H), 8.20 (s, 1H), 7.88 (d, J=7.5 Hz, 2H), 7.76 (d, J=6.1 Hz, 2H), 7.70 (d, J=8.0 Hz, 1H), 7.59 (m, 1H), 7.40 (m, 4H), 7.19 (d, J=8.3 Hz, 1H), 3.52 (s, 2H), 2.50 (s, 8H), 2.25 (s, 3H), 2.15 (s, 3H); $^{13}$C NMR δ 165.16, 161.25, 161.11, 159.59, 149.38, 147.02, 142.07, 137.76, 137.23, 136.52, 135.47, 133.64, 132.31, 132.17, 131.67, 131.58, 129.99, 129.05, 128.64, 128.58, 128.27, 127.19, 127.57, 126.92, 116.79, 116.38, 107.74, 61.59, 54.69, 52.56, 45.73, 17.60.

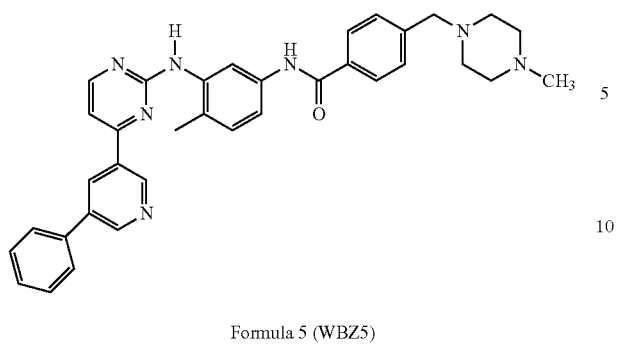

Formula 5 (WBZ5)

G. Synthesis of WBZ6

Referring to scheme 2, nicotinate (11) was first treated with sodium hydrate and refluxed with ethyl acetate to form methyl 6-methylnicotinylacetate. The intermediate acetate was then hydrolyzed to form 3-Acetyl-6-methylpyridine(13) (U.S. Patent Application Publication 20040248918). The WBZ2 compound can be synthesized similarly using pyridine(13).

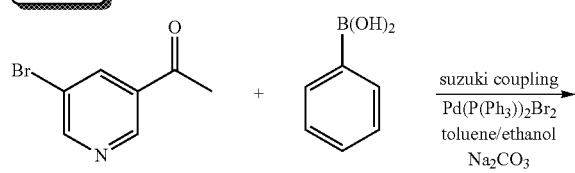

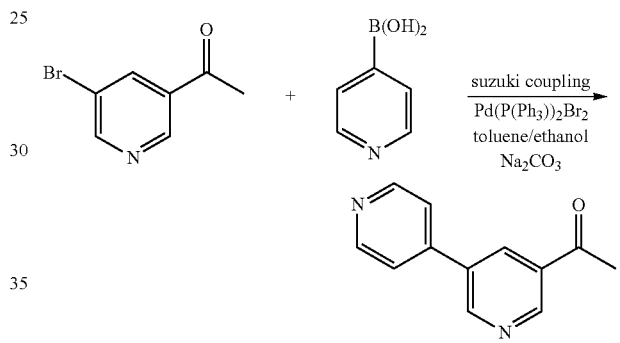

Following the procedure of step 5.1, but substituting pheylbornonic acid for 4-pyridineboronic acid, 5-(4-pyridinyl)-3-acetylpyridine (step 6.1) was obtained as a solid. 1 g (5 mmol, 50%). TLC Rf=0.1 (50% EtOAc/hexane); MS: 199.5 (M+H); TLC Rf 0.3 (1:1 hexane/EtOAc); MS: 198.5 (M+H); $^1$H NMR (DMSO) δ 9.25 (d, J=1.6 Hz, 1H), 9.19 (d, J=1.6 Hz, 1H), 8.73 (d, J=4.7 Hz, 2H),), 8.63 (s, 1H), 7.90 (d, J=4.6 Hz, 2H), 2.73 (s, 3H); $^{13}$C NMR δ 197.32, 151.68, 150.54, 149.02, 143.36, 134.20, 133.02, 132.34, 132.08, 132.01, 121.65, 27.14.

Step 6.1

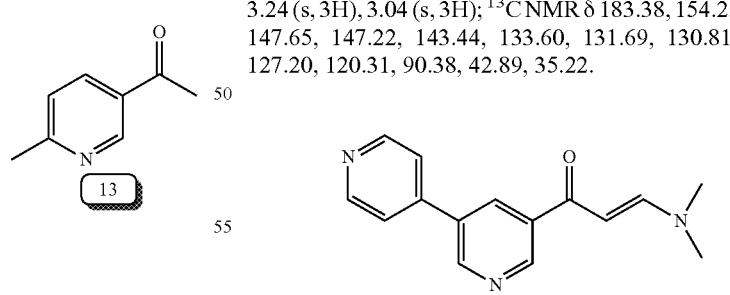

Following the procedure of step 1.3, but substituting 3-acetyl-4-methyl-pyridine for 3-Acetyl 5-(4-pyridinyl)-pyridine, 3-dimethylamino-1-(3-(5-(4-pyridinyl)-pyridyl))-2-propen-1-one was obtained as a solid. (1.5 g, 90%). Rf=0.46 (Methylene chloride:Methanol=9:1). MS: 254.2 (M+H); 1H NMR (DMSO) δ 9.12 (s, 1H), 9.05 (d, J=5.2 Hz, 1H), 8.70 (d, J=5.9 Hz, 2H), 8.57 (d, J=5.2 Hz, 1H), 7.84 (d, J=5.9 Hz, 2H), 3.24 (s, 3H), 3.04 (s, 3H); $^{13}$C NMR δ 183.38, 154.25, 148.39, 147.65, 147.22, 143.44, 133.60, 131.69, 130.81, 130.13, 127.20, 120.31, 90.38, 42.89, 35.22.

3-dimethylamino-1-(3-(5-(4-pyridinyl)-pyridyl))-2-propen-1-one

Following the procedure of step 1.5 and 1.6, but substituting 3-dimethylamino-1-(3-(4-methyl-pyridyl))-2-propen-1-one for 3-dimethylamino-1-(3-(5-(4-pyridinyl)-pyridyl))-2-propen-1-one, N-(2-methyl-5-aminophenyl)-5-(4-pyridinyl)-pyridyl)-2-pyrimidine-amine was obtained as a solid. MS: 356.5 (M+H).

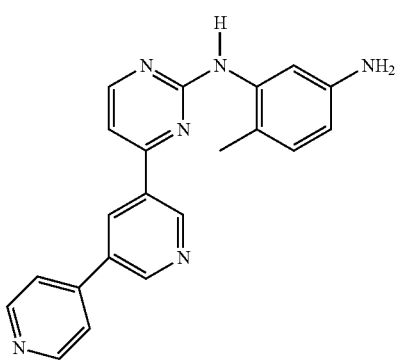

N-(2-methyl-5-aminophenyl)-5-(4-pyridinyl)-2-pyrimidine-amine

Following the procedure of step 1.9, but substituting N-(2-methyl-5-aminophenyl)-4-(4-methyl-pyridyl))-2-pyrimidine-amine for N-(2-methyl-5-aminophenyl)-5-(4-pyridinyl)-pyridyl)-2-pyrimidine-amine, N-{5-[4-(4-methyl piperazine methyl)-benzoylamido]-2-methylphenyl}-4-[3-(5-(4-pyridinyl)-pyridyl]-2-pyrimidine amine (Formula 7, WBZ6) was obtained as a solid. MS: 571.4 (M+H); 1H NMR (DMSO) δ 10.18 (s, 1H), 9.45 (d, J=1.2 Hz, 1H), 9.12 (d, J=2.1 Hz, 1H), 9.05 (s, 1H), 8.83 (t, J=2.2 Hz, 1H), 8.58 (d, J=5.1 Hz, 1H), 8.55 (d, J=5.1 Hz, 1H), 8.24 (s, 1H), 7.86 (d, J=7.9 Hz, 2H), 7.82 (d, J=5.1 Hz, 2H), 7.61 (d, J=5.2 Hz, 1H), 7.48 (dd, 8.2, 1.6 Hz, 1H), 7.40 (d, J=7.9 Hz, 2H), 7.19 (d, J=8.3 Hz, 1H), 3.52 (s, 2H), 2.50 (s, 8H), 2.25 (s, 3H), 2.15 (s, 3H); $^{13}$C NMR δ 165.17, 161.09, 160.95, 159.71, 150.26, 149.55, 148.60, 143.74, 142.15, 137.72, 137.21, 133.60, 132.79, 132.54, 132.51, 130.02, 128.59, 127.53, 127.10, 121.40, 116.71, 116.36, 107.86, 61.59, 54.69, 52.56, 45.73, 17.60

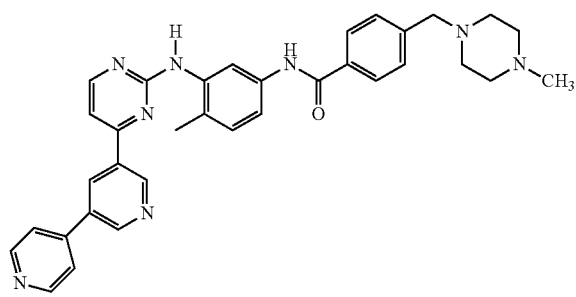

Formula 7 (WBZ6)

H. Synthesis of WBZ7

Following the procedure of step 1.3, but substituting N,N-dimethylformamide for N,N-dimethylacetamide, 3-dimethylamino-1-pyridyl-2-butene-1-one was obtained as a solid. (2 g, 90%). $R_f$=0.46 (Methylene chloride:Methanol=9:1). MS: 191.3 (M+H); $^1$H NMR (DMSO) δ 9.00 (s, 1H), 8.62 (d, J=4.2 Hz, 1H), 8.15 (d, J=7.8 Hz, 1H), 7.43 (dd, J=7.2, 4.8 Hz, 1H), 5.64 (s, 1H), 3.08 (s, 6H), 2.60 (s, 3H); $^{13}$C NMR δ 183.40, 164.43, 150.84, 148.20. 137.65, 134.39, 123.26, 90.79, 16.00.

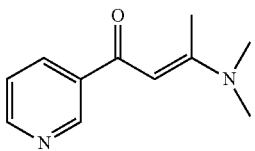

3-dimethylamino-1-pyridyl-2-butene-1-one

Following the procedure of step 1.5 and 1.6, but substituting 3-dimethylamino-1-(3-(4-methyl-pyridyl))-2-propen-1-one for 3-dimethylamino-1-pyridyl-2-butene-1-one, N-(2-methyl-5-aminophenyl)-4-pyridyl-6-methyl-2-pyrimidine-amine was obtained as a solid. MS: 292.3 (M+H); $^1$H NMR (DMSO) δ 9.22 (d, J=1.2 Hz, 1H), 8.68 (dd, J=4.8, 1.2 Hz, 1H), 8.55 (s, 1H), 8.38 (d, J=8.4 Hz, 1H), 7.53 (dd, J=7.8, 5.4 Hz, 1H), 6.87 (d, J=8.4, 1H), 6.85 (s, J=1.8 Hz, 1H), 6.33 (dd, J=8.4, 2.4 Hz, 1H), 4.84 (s, 2H), 2.38 (s, 3H), 2.07 (s, 3H). $^{13}$C NMR δ 168.78, 161.15, 161.06, 151.08, 148.05, 146.67, 138.10, 134.18, 132.48, 130.25, 123.74, 119.09, 110.85, 110.65, 106.52, 23.86, 17.26.

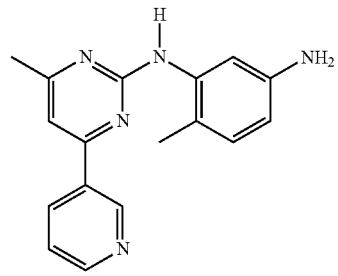

N-(2-methyl-5-aminophenyl)-4-pyridyl-6-methyl-2-pyrimidine-amine

Following the procedure of step 1.9, but substituting N-(2-methyl-5-aminophenyl)-4-(4-methyl-pyridyl))-2-pyrimidine-amine for N-(2-methyl-5-aminophenyl)-4-pyridyl-6-methyl-2-pyrimidine-amine, N-{5-[4-(4-methyl piperazine methyl)-benzoylamido]-2-methylphenyl}-6-methyl-4-(3-pyridyl)-2-pyrimidine amine (Formula 8) was obtained as a solid. MS: 508.5 (M+H); 1H NMR (CDCl$_3$) δ 9.21 (s, 1H), 8.74 (s, 1H), 8.65 (d, J=4.2 Hz, 1H), 8.53 (d, J=7.8 Hz, 1H), 7.95 (s, 1H), 7.83 (d, J=7.8 Hz, 2H), 7.83 (d, J=7.8 Hz, 2H), 7.38 (dd, J=7.8, 4.8 Hz, 1H), 7.23 (d, J=7.8 Hz, 1H), 7.18 (d, J=7.8 Hz, 1H), 7.06 (s, 1H), 6.99 (s, 1H), 3.56 (s, 2H), 2.50 (s, 3H), 2.46 (br, 8H), 2.34 (s, 3H), 2.29 (s, 3H). $^{13}$C NMR δ 169.20, 165.39, 162.34, 160.39, 151.21, 148.47, 142.54, 138.16, 136.62, 135.10, 134.03, 132.99, 130.64, 129.31, 127.01, 123.70, 123.60, 114.78, 112.75, 108.03, 62.53, 55.13, 53.15, 24.41, 17.71.

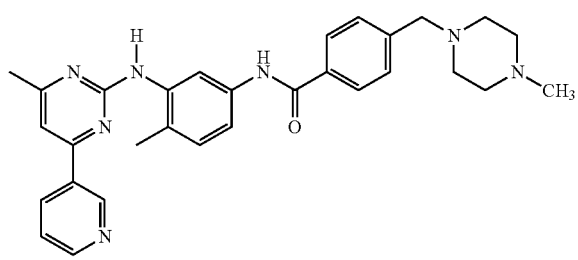

Formula 8 (WBZ7)

I. Compound Assessment

Prototype re-engineered compounds will be assessed for cell inhibitory effects using cancer cell line model systems. Cancer cells are usually dependent on specific tyrosine kinase signaling pathways for survival. In certain situations a biological pathway is abnormally active due to mutations that keep such kinases continuously activated. This is the case of the Bcr-Abl fusion protein where the regulatory domain (normally located at the end of the ABL gene) of the Abl kinase is lost (Pluk et al., 2002) and the C-Kit receptor where certain gain-of-function mutations keep it activated (DeMatteo et al., 2002). Inhibition of these active tyrosine kinases leads to apoptosis and cell growth arrest (Beran, 1998). In this way, the efficacy of an inhibitor can be determined as the capacity to inhibit cell growth, as clearly demonstrated herein. Cell-line selection will be based on specific expression of the target protein and documented growth inhibition when treated with the initial lead compound.

When tyrosine kinases are activated, two reactions take place: (1) Dimerization of two monomeric kinases that include formation of dimers with the same tyrosine kinase (homodimers) or with similar but not identical tyrosine kinases (heterodimers). (2) Phosphorylation of the partner kinase within the dimer (autophosphorylation) that opens up the kinase domain to allow ATP binding (Tibes et al., 2005). The activity of an inhibitor can be determined by examining the phosphorylation status of the target kinase. If the inhibitor is active, an absence or decrease of the phosphorylation status will be seen (Gambacorti-Passerini et al., 1997). The dominant assay to determine activity of an inhibitor is to examine the phosphorylation status of specific substrates. For example, crkl, a specific substrate for Bcr-Abl, is usually used as an indicator for Bcr-Abl activation (Dan et al., 1998). In order to determine phosphorylation status of the protein, immunoblots are typically used. Proteins are blotted with antibodies that recognized phosphorylation sites of specific proteins or by immunoprecipitating a specific protein and latter blotting with an antibody that recognized phosphorylated sites.

III. Imaging and Diagnosis

In certain aspects of the invention, wrapping ligands are engineered to contain optically active reporters which enable high spatial and temporal resolution imaging of drug localization in cell lines, animal models and eventually in patients. High throughput optical screening assays will be carried out using optically active reporters to assess the cellular and tissue distribution of wrappers designed to have enhanced target specificity. Because of the optical signal associated with the wrappers, these assays will provide high spatial and temporal resolution images of drug localization, enabling subcellular visualization of molecular pharmacology. Further aspects include the use of optically active wrapping ligands targeted towards cancer-related kinases as imaging vectors capable of generating a detectable signal for cancer diagnosis for use in tumor detection. This approach will take advantage of the enhanced target specificity to increase the image contrast between tumor/normal tissue, reducing adventitious signals and ambiguity in imaging diagnosis of cancer. In certain non-limiting aspects, the inventors will focus on particular types of cancer associated with specific pharmacokinomes susceptible of selectivity modulation using the wrapping technology. Thus, of particular interest are chronic myeloid leukemia, colorectal cancer, and sarcomas, since certain kinases directly associated with them (Bcr-Abl, C-kit, and SRC respectively) may be selectively targeted using the wrapping technology, as indicated below.

1. Optically Active Reporters.

In certain aspects of the invention fluorophores can be introduced to the wrapping ligands, e.g., at least 1, 2, 3, or more: Eu(III) chelates and near-infrared fluorescence (NIRF) organic dyes, such as indocyanine green. Eu(III) chelates emit fluorescence (575-790 nm) when excited by ultraviolet light. Eu(III) chelates are of interest because of their long life time (milliseconds) and their narrow emission spectrum which can increase contrast in fluorescence imaging when autofluorescence is a problem. The use of NIRF dyes will allow extension of fluorescence imaging from in vitro system to in vivo animal imaging studies. For example, for the introduction of Eu(III), p-Succinamidobenzyl-DTPA-t-butyl ester will be conjugated to Gleevec analogues at the demethylated piperazine amine site with or without a linker group according to previously reported procedures (Wang et al., 2005). The t-butyl protection group will then be removed followed by chelation with Eu(III). For the introduction of organic NIRF dyes, N-hydroxysuccinimide activated esters of Cy5.5 (ex/em: 675/694) and indocyanine green analogue IRDye800 (ex/em: 765/792 nm) will be conjugated to Gleevec analogues with or without a linker group according to previously reported procedures (Wang et al., 2004)

2. Optical Imaging

Real time optical imaging systems have been developed to image morphologic and molecular features of neoplasia at two length scales. In the first, low resolution, widefield microscopes, capable of imaging areas with a large field of view (5-15 cm) are used to identify areas suspicious for neoplasia. In the second approach, high resolution microscopes, operating near the diffraction resolution limit, are used to image the morphologic and molecular characteristics of neoplastic lesions.

Simple, inexpensive systems have been developed to image tissue at video rate in vivo, providing information to guide placement of higher resolution imaging systems. In one approach, the inventors modified a colposcope to enable collection of quantitative images of autofluorescence and targeted contrast agent fluorescence—the resulting device is a multi-spectral, digital colposcope (MDC) that can capture autofluorescence images at video rate in vivo (Benavides et al., 2003; Park et al., 2005).

These systems have been used to image fluorescence in intact small animal models of neoplasia. FIG. 3 shows white light and fluorescence images of subcutaneous MDA-MB-435 tumors in a nude mouse model. Tumors formed with RFP expressing cells show easily detectable autofluorescence as early as 2 weeks following injection, while RFP negative control tumors do not show detectable fluorescence. Micrometastases in the excised lung can easily be detected via the RFP fluorescence. This concept has been extended to assessing application of wrapping ligands targeted with NIRF agents in small animal models.

To image the distribution of wrapping ligands with subcellular resolution in vivo, higher resolution microscopes are required that can be used to image intact tissues. In vivo confocal microscopes have been developed that can provide detailed images of tissue architecture and cellular morphology in living tissue in near real time. In epithelial tissue, 1 micron resolution has been achieved with a 200-400 micron field of view and penetration depth up to 500 microns (Collier et al., 2000, 2002; Drezek et al., 2000; Rajadhyaksha et al., 1995, 1999a,b, 2001a,b; Selkin et al., 2001; White et al., 1999; Delaney and Harris, 1995). The inventors have developed a version of this microscope that measures both fluorescence and reflectance images in real time. This microscope can be used to image the distribution of optically active wrapping ligands in small animal model systems. Widefield microscopy will be used to identify regions of interest for high resolution imaging.

Fiber optic confocal microscopes are needed to obtain images of areas that are located deep beneath the tissue surface (Liang et al., 2002; Sung et al., 2002a, b). A number of fiber optic confocal microscopes have been developed that are currently being tested in vivo to image precancerous lesions in the uterine cervix and the oral cavity at the M. D. Anderson Cancer Center (MDACC). These systems have a lateral resolution of approximately 2 microns, an axial resolution of approximately 5 microns and can obtain images throughout the entire epithelial thickness. The inventors contemplate extending this concept of high resolution imaging, based on a much simpler alternative approach. The alternative approach is based on the observation that high resolution optical images of the top 1-2 layers of cells can be obtained without the need for a confocal imaging gate if the cells are placed in direct contact with a flat optical window. Using this principle, the inventors have developed a micro-imaging system which can be inserted in a small gauge needle and advanced through tissue to obtain images at video rate. The system is 300 microns in outer diameter and has a flat optical window at the distal tip which can be inserted into a tumor to image tissue fluorescence from the layer of cells in contact with this distal window with subcellular resolution.

IV. Administration of Wrapper Compounds

In additional embodiments, the present invention concerns formulation of wrapper compound compositions disclosed herein in pharmaceutically-acceptable solutions for administration to a cell, tissue, animal, or patient either alone, or in combination with one or more second agent or second therapy.

Aqueous pharmaceutical compositions of the present invention will have an effective amount of a wrapper compound that modulates a target protein of interest and/or its related biological functions or activities. Such compositions generally will be dissolved or dispersed in a pharmaceutically acceptable carrier or aqueous medium. An "effective amount," for the purposes of therapy, is defined at that amount that causes a clinically measurable difference in the condition of the subject. This amount will vary depending on the condition, the substance, the condition of the patient, the type of treatment, etc.

The phrases "pharmaceutically" or "pharmacologically acceptable" refer to molecular entities and compositions that do not produce a significant adverse, allergic, or other untoward reaction when administered to an animal, or human. As used herein, "pharmaceutically acceptable carrier" includes any and all solvents, dispersion media, coatings, antibacterial and antifungal agents, isotonic, absorption delaying agents and the like. The use of such media and agents for pharmaceutically active substances is well known in the art. Except insofar as any conventional media or agent is incompatible with the active ingredients, its use in the therapeutic compositions is contemplated. Supplementary active ingredients, such as other therapeutic agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including creams, lotions, inhalants and the like.

The active compounds of the present invention can be formulated for parenteral administration, e.g., formulated for injection via the intravenous, intramuscular, subcutaneous, or even intraperitoneal routes. The preparation of a composition that contains a wrapper compound alone or in combination with a second therapeutic agent as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injection include sterile aqueous solutions or dispersions; formulations including lipids, sesame oil, peanut oil, or aqueous propylene glycol; and sterile powders for the extemporaneous preparation of sterile injectable solutions or dispersions. In many cases, the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts and which are formed with inorganic acids such as, for example, hydrochloric or phosphoric acids, or such organic acids as acetic, oxalic, tartaric, mandelic, and the like. Salts formed can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous or lipid solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 1035-1038 and 1570-1580). Some variation in dosage will necessarily occur depending on the condition of the subject being treated. The person responsible for administration will, in any event, determine the appropriate dose for the individual subject.

In certain aspects of the invention, the route of administering a therapeutic composition may be by parenteral administration. The parenteral administration may be intravenous injection, subcutaneous injection, intramuscular injection, ingestion, or a combination thereof. In certain aspects, the composition comprising a wrapper compound is administered from about 0.01, 0.05, 0.1, 0.2, 0.3, 0.4, 0.5, 1.0, 2, 3, 4, 5, 6, 7, 8, 9, to about 10, 20, 30, 40, 50, 60, 70, 80, 90, or 100 nanogram or microgram/kg/body weight per dose, including integers and ranges derivable there between. In certain aspects, the composition comprising a wrapper compound is administered from about 1 to about 5 nanogram or microgram/kg/body weight per dose. In certain aspects, the composition comprising a wrapper compound is administered from about 1.2 to about 2.4 nanogram or microgram/kg/body weight per dose. In certain aspects, the amount of wrapper compound administered per dose may be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9. about 3.0, about 3.1, about 3.2, about 3.3, about 3.4, about 3 5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8. about 9.9 to about 10.0 or more nanogram/kg/body, microgram/kg/body or milligram/kg/body.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

A. Alimentary Delivery

The term "alimentary delivery" refers to the administration, directly or otherwise, to a portion of the alimentary canal of a subject or patient. The term "alimentary canal" refers to the tubular passage that functions in the digestion and absorption of food and the elimination of food residue, which runs from the mouth to the anus, and any and all of its portions or segments, e.g., the oral cavity, the esophagus, the stomach, the small and large intestines and the colon, as well as compound portions thereof such as, e.g., the gastro-intestinal tract. Thus, the term "alimentary delivery" encompasses several routes of administration including, but not limited to, oral, rectal, endoscopic and sublingual/buccal administration. A common requirement for these modes of administration is absorption over some portion or all of the alimentary tract and a need for efficient mucosal penetration of the nucleic acid(s) so administered.

1. Oral Delivery

In certain applications, the pharmaceutical compositions disclosed herein may be delivered via oral administration to an animal or human. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; U.S. Pat. Nos. 5,641, 515; 5,580,579 and 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

2. Endoscopic Administration

Endoscopy can be used for therapeutic delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., 1992). However, the procedure is unpleasant for the patient, and requires a highly skilled staff.

B. Rectal Administration

Therapeutics administered by the oral route can often be alternatively administered by the lower enteral route, i.e., through the anal portal into the rectum or lower intestine. Rectal suppositories, retention enemas or rectal catheters can be used for this purpose and may be preferred when patient compliance might a otherwise be difficult to achieve (e.g., in pediatric and geriatric applications, or when the patient is vomiting or unconscious). Rectal administration may result in more prompt and higher blood levels than the oral route, but the converse may be true as well (Remington's Pharmaceutical Sciences, 711, 1990). Because about 50% of the therapeutic that is absorbed from the rectum will bypass the liver, administration by this route significantly reduces the potential for first-pass metabolism (Benet et al., 1996).

C. Injectable Delivery

In certain circumstances it will be desirable to deliver the pharmaceutical compositions disclosed herein parenterally, intravenously, intramuscularly, or even intraperitoneally as described in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that it is easy to use a syringe.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration (see for example, Remington's Pharmaceutical Sciences, 1035-1038 and 1570-1580. Some variation in dosage will necessarily occur depending on the condition of the subject being treated. The person responsible for administration will, in any event, determine the appropriate dose for the individual subject.

Moreover, for human administration, preparations should meet sterility, pyrogenicity, and the general safety and purity standards as required by governmental regulations and standards.

The term "parenteral delivery" refers to the administration of a therapeutic of the invention to an animal in a manner other than through the digestive canal. Means of preparing and administering parenteral pharmaceutical compositions are known in the art (see, e.g., Remington's Pharmaceutical Sciences, pages 1545-1569, 1990).

D. Intraluminal Administration

Intraluminal administration, for the direct delivery of a therapeutic to an isolated portion of a tubular organ or tissue (e.g., such as an artery, vein, ureter or urethra), may be desired for the treatment of patients with diseases or conditions afflicting the lumen of such organs or tissues. To effect this mode of administration, a catheter or cannula is surgically introduced by appropriate means. After isolation of a portion of the tubular organ or tissue for which treatment is sought, a composition comprising a therapeutic of the invention is infused through the cannula or catheter into the isolated segment. After incubation for from about 1 to about 120 minutes, during which the therapeutic is taken up or in contact with the cells of the interior lumen of the vessel, the infusion cannula or catheter is removed and flow within the tubular organ or tissue is restored by removal of the ligatures which effected the isolation of a segment thereof (Morishita et al., 1993). Therapeutic compositions of the invention may also be combined with a biocompatible matrix, such as a hydrogel material, and applied directly to vascular tissue in vivo.

E. Nasal Delivery

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

F. Epidermal and Transdermal Delivery

Epidermal and transdermal delivery, in which pharmaceutical compositions containing therapeutics are applied topically, can be used to administer drugs to be absorbed by the local dermis or for further penetration and absorption by underlying tissues, respectively. Means of preparing and administering medications topically are known in the art (see, e.g., Remington's Pharmaceutical Sciences, 1596-1609, 1990).

G. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells or to subjects in need of treatment. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the wrapper compounds disclosed herein. The formation and use of liposomes is generally known to those of skill in the art (see below and see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Chonn, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. Nos. 5,567,434; 5,552,157; 5,565,213; 5,738,868 and 5,795,587, each specifically incorporated herein by reference in its entirety).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

The fate and disposition of intravenously injected liposomes depend on their physical properties, such as size, fluidity, and surface charge. They may persist in tissues for hours or days, depending on their composition, and half lives in the blood range from minutes to several hours. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998). Biodegradable polyalkyl-cyanoacrylate nanoparticles that meet these requirements are contemplated for use in the present invention. Such particles may be are easily made, as described (zur Muhlen et al., 1998; Pinto-Alphandary et al., 1995 and U.S. Pat. No. 5,145,684, specifically incorporated herein by reference in its entirety).

V. Lipid Formulations

The present invention includes liposomal drug formulations comprising a wrapper compound or optimized drug, and any type of lipid composition or liposome known in the art, including those exemplified below. As used herein, a liposome is a structure having lipid-containing membranes enclosing an aqueous interior. Liposomes may have one or more lipid membranes. The invention includes both single-layered liposomes, which are referred to as unilamellar, and multi-layer liposomes, which are referred to as multilamellar. In further aspects, lipid compositions need not contain significant levels of structure as long as the deliver of the wrapper compound is facilitated.

A. Liposome/Lipid Composition

Lipid compositions of the invention may include any of a wide variety of different lipids, including, e.g., amphipathic, neutral, cationic, and anionic lipids. Such lipids can be used alone or in combination, and can also include additional components, such as cholesterol, bilayer stabilizing components, e.g., polyamide oligomers (see, U.S. Pat. No. 6,320,017), peptides, proteins, detergents, and lipid-derivatives, such as PEG coupled to phosphatidylethanolamine and PEG conjugated to ceramides (see U.S. Pat. No. 5,885,613).

In numerous embodiments, amphipathic lipids are included in liposomes of the present invention. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidyicholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and t3-acyloxyacids, can also be used. Additionally, such amphipathic lipids can be readily mixed with other lipids, such as triglycerides and sterols.

Any of a number of neutral lipids can be included, referring to any of a number of lipid species which exist either in an uncharged or neutral zwitterionic form at physiological pH, including, e.g., diacyiphosphatidylcholine, diacylphosphatidylethanolamine, ceramide, sphingomyelin, cephalin, cholesterol, cerebrosides, diacylglycerols, and sterols.

Cationic lipids, which carry a net positive charge at physiological pH, can readily be incorporated into liposomes for use in the present invention. Such lipids include, but are not limited to, N,N-dioleyl-N,N-dimethylammonium chloride ("DODAC"); N-(2,3-d-ioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 313-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), d-ioctadecylamidoglycyl carboxyspermine ("DOGS"), 1,2-dileoyl-sn-3-phosphoethanolamine ("DOPE"), 1,2-dioleoyl-3-dimethylammonium propane (t1DODAP"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL).

Anionic lipids suitable for use in the present invention include, but are not limited to, phosphatidylglycerol, cardiolipin, diacylphosphatidylserine, diacyiphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

In one embodiment, cloaking agents, which reduce elimination of liposomes by the host immune system, can also be included in liposomes of the present invention, such as polyamide-oligomer conjugates, and PEG-lipid conjugates (see, U.S. Pat. Nos. 5,820,873, 5,534,499 and 5,885,613).

Also suitable for inclusion in the present invention are programmable fusion lipid formulations. Such formulations have little tendency to fuse with cell membranes and deliver their payload until a given signal event occurs. This allows the lipid formulation to distribute more evenly after injection into an organism or disease site before it starts fusing with cells. The signal event can be, for example, a change in pH, temperature, ionic environment, or time. In the latter case, a fusion delaying or "cloaking" component, such as a PEG-lipid conjugate, can simply exchange out of the liposome membrane over time. By the time the formulation is suitably distributed in the body, it has lost sufficient cloaking agent so as to be fusogenic. With other signal events, it is desirable to choose a signal that is associated with the disease site or target cell, such as increased temperature at a site of inflammation.

In certain embodiments, liposomes of the present invention comprises sphingomyelin (SM). As used herein, the general term sphingomyelin (SM) includes SMs having any long chain base or fatty acid chain. Naturally occurring SMs have the phosphocholine head group linked to the hydroxyl group on carbon one of a long-chain base and have a long saturated acyl chain linked to the amide group on carbon 2 of the long-chain base (reviewed in Barenholz, Y. In Physiology of Membrane Fluidity, Vol. 1. M. Shinitsky, editor. CRC Press, Boca Raton, Fla. 131-174(1984)). In cultured cells, about 90 to 95% of the SMs contain sphingosine (1,3-dihydroxy-2-amino-4-octadecene), which contains a trans-double bond between C4 and C5, as the long-chain base, whereas most of the remainder have sphinganine (1,3-dihydroxy-2-amino-4-octadecane) as the base and lack the trans double bond between carbons 4 and 5 of the long chain base. The latter SMs are called dihydrosphingomyelins (DHSM). DHSM may contain one or more cis double bonds in the fatty acid chain. In one embodiment, DHSM contains both a fully saturated fatty acid chain and a saturated long base chain. Liposomes comprising SM or, specifically, DHSM, are described in further detail in U.S. Provisional Patent Application No. 60/571,712.

In certain embodiments, it is desirable to target the liposomes of this invention using targeting moieties that are specific to a cell type or tissue. Targeting of liposomes using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044). The targeting moieties can comprise the entire protein or fragments thereof. A variety of different targeting agents and methods are described in the art, e.g., in Sapra and Allen (2003); and Abra et al (2002).

The use of liposomes with a surface coating of hydrophilic polymer chains, such as polyethylene glycol (PEG) chains, for targeting has been proposed (Allen et al., 1995; Blume et al., 1993; Klibanov et al., 1992; Zalipsky, 1994; Zalipsky, 1995). In one approach, a ligand, such as an antibody, for targeting the liposomes is linked to the polar head group of lipids forming the liposome. In another approach, the targeting ligand is attached to the distal ends of the PEG chains forming the hydrophilic polymer coating (Klibanov et al., 1992; Kirpotin, et al., 1992).

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen et al., (1990) and Leonetti et al. (1990). Other examples of antibody conjugation are disclosed in U.S. Pat. No. 6,027,726. Examples of targeting moieties also include other proteins, specific to cellular components, including antigens associated with neoplasms or tumors. Proteins used as targeting moieties can be attached to the liposomes via covalent bonds (see, Heath, 1987)). Other targeting methods include the biotin-avidin system.

B. Methods of Preparation

A variety of methods for preparing liposomes are known in the art, including e.g., those described in Szoka et al. (1980); U.S. Pat. Nos. 4,186,183, 4,217,344, 4,235,871, 4,261,975, 4,485,054, 4,501,728, 4,774,085, 4,837,028, 4,946,787; PCT Publication No. WO 91/1 7424; Deamer and Bangham (1976); Fraley et al. (1979); Hope et al. (1985); Mayer et al., (1986); Williams et al. (1988); Liposomes, 1983; Hope et al. (1986); and Liposomes: A Practical Approach (2003), and references cited therein. Suitable methods include, but are not limited to, sonication, extrusion, high pressure/homogenization, microfluidization, detergent dialysis, calcium-induced fusion of small liposome vesicles, and ether-infusion methods, all of which are well known in the art.

Alternative methods of preparing liposomes are also available. For instance, a method involving detergent dialysis based self-assembly of lipid particles is disclosed and claimed in U.S. Pat. No. 5,976,567. Further methods of preparing liposomes using continuous flow hydration are under development and can often provide the most effective large scale manufacturing process.

Unilamellar vesicles can be prepared by sonication or extrusion. Sonication is generally performed with a tip sonifier, such as a Branson tip sonifier, in an ice bath. Typically, the suspension is subjected to severed sonication cycles.

Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass.

Unilamellar vesicles can also be made by dissolving phospholipids in ethanol and then injecting the lipids into a buffer, causing the lipids to spontaneously form unilamellar vesicles. Also, phospholipids can be solubilized into a detergent, e.g., cholates, Triton X, or n-alkylglucosides. Following the addition of the drug to the solubilized lipid-detergent micelles, the detergent is removed by any of a number of possible methods including dialysis, gel filtration, affinity chromatography, centrifugation, and ultrafiltration.

Following liposome preparation, the liposomes that have not been sized during formation may be sized to achieve a desired size range and relatively narrow distribution of liposome sizes. A size range of about 0.2-0.4 microns allows the liposome suspension to be sterilized by filtration through a conventional filter.

The filter sterilization method can be carried out on a high throughput basis if the liposomes have been sized down to about 0.2-0.4 microns.

Several techniques are available for sizing liposomes to a desired size. General methods for sizing liposomes include, e.g., sonication, by bath or by probe, or homogenization, including the method described in U.S. Pat. No. 4,737,323. Sonicating a liposome suspension either by bath or probe sonication produces a progressive size reduction down to small unilamellar vesicles less than about 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield (1981), incorporated herein by reference. Liposomes of any size may be used according to the present invention. In certain embodiments, liposomes of the present invention have a size ranging from about 0.05 microns to about 0.45 microns, between about 0.05 and about 0.2 microns, or between 0.08 and 0.12 microns in diameter. In other embodiments, liposomes of the present invention are between about 0.45 microns to about 3.0 microns, about 1.0 to about 2.5 microns, about 1.5 to about 2.5 microns and about 2.0 microns.

VI. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are not intended as limitations on the scope of the invention. Changes therein and other uses which are encompassed within the spirit of the invention as defined by the scope of the claims will occur to those skilled in the art.

The inventors provide examples of the drug-redesign strategy for enhancing specificity in anticancer activity guided by a structural discriminator of alternative targets. The molecular impact of the prototypes is translated into assays for validation of the design concept. As described below, the inventors use two cancer-related targets as examples. The targets are kinase modulated by the powerful inhibitor imatinib (Gleevec, STI571) (Donato and Talpaz, 2000; Fabian et al., 2005): Bcr-Abl, the Abelson kinase target for treating CML (chronic myeloid leukemia) (Faderl et al., 1999; Gambacorti-Passeerini, et al., 1997; Schindler et al., 2000), and the C-Kit kinase, a target for GIST (gastrointestinal stromal) tumors (Attoub et al., 2002; DeMatteo, 2002; Noma et al., 2005). Also, the inventors use the kinase inhibitor staurosporine as an additional example.

Initial efforts to establish a wrapping technology for ligand engineering were directed at testing the feasibility of integrating such diverse fields as in-silico design, actual compound synthesis, and in vitro assays. The extent of success of the pilot project, with meaningful results in less than 5 months, attests to the capability of pursuing the approach.

Example 1

Ligand Design of a C-Kit Inhibitor Based on Imatinib (Gleevec)

In one instance, imatinib was reengineered to achieve specificity towards C-Kit based on a molecular marker that distinguishes its ATP-pocket from that of Bcr-Abl. The discriminating molecular design is reflected in selective anticancer activity on GIST cell lines. Validation is achieved by determining differences in competitive affinity between imatinib and the prototype variant, highlighting the higher specificity of the latter.

A. In Silico Design

To engineer the affinity discriminator for C-Kit, the inventors compare the patterns of residence times of water molecules that solvate the aligned interfacial regions of PDB-reported imatinib targets Bcr-Abl (PDB.1FPU), C-Kit (PDB.1T46) and Lck (lymphocyte specific tyrosine kinase, PDB.3LCK) (FIG. 4). Hydrating molecules with low residence times (FIG. 4) constitute a blueprint for ligand re-engineering since they signal a local propensity for water removal. The crux of the redesign strategy is then the sculpting in the ligand of nonconserved local de-wetting propensities in the aligned targets: the ligand is engineered to remove interfacial water upon association according to weaknesses in the target hydration shell. Since this blueprint is typically not conserved across targets—although most surface residues in the binding region are—the inhibitory impact of the compound can be modulated to a certain extent. The key de-wetting hot spots correspond to amide-carbonyl backbone hydrogen bonds pairing backbone-exposed residues (Chen et al., 2007). Such bonds become energetically enhanced and stabilized upon removal of surrounding water and thus constitute de-wetting sites.

The stochastic boundary molecular dynamics (SBMD) method (Brooks and Karplus, 1989) was employed to reduce simulation times while capturing localized interactions at the protein active site. The simulation used the CHARMM program (Brooks et al., 1983). Polar-hydrogen potential function (PARAM19) (Neria et al., 1996) was employed for the protein and a modified TIP3P water model (Jorgensen, 1981) was used for the solvent. Partial charges on the kinase were computed by ab initio quantum calculation and the van der Waals parameters of its atoms were adopted from amino acid side chains subsumed in the CHARMM force field. The system had a reaction zone and a reservoir region, and the reaction zone was further separated into a reaction region and a buffer region (Brooks and Karplus, 1989). The central point for partitioning was chosen to be at the substitution carbon atom on the imatinib molecule. The reaction region around the active site is defined by a sphere of radius r=14 Å, the buffer region is defined by the sector: 14 Å<r<16 Å, and the reservoir region, by r>16 Å. All the atoms in the reservoir region were omitted. For C-Kit kinase, the final simulation system had 84 protein residues, an imatinib molecule initially positioned as in PDB entry 1T46, and 239 water molecules. For Bcr-Abl kinase (PDB.1FPU), the final simulation system had 90 protein residues, an imatinib molecule, and 300 water molecules. Atoms inside the reaction region were propagated by molecular dynamics, and atoms in the buffer region were propagated by the Langevin dynamics. Atoms inside the buffer region were harmonically restrained by forces with constants derived from the temperature factors in crystal structures. Water molecules were confined to the active-site region by a deformable boundary potential. The friction constant in the Langevin dynamics was 250 $ps^{-1}$ for protein atoms and 62 $ps^{-1}$ for water molecules. A 1 fs time step was used for integrating the equations of motion. Initial random velocities were taken from the Boltzmann distribution. The system was equilibrated for 50 ps at 300K, and was then followed through a 1 ns-run. Five 1 ns-trajectories were generated for each inhibitor-protein complexation.

A de-wetting hot spot in C-Kit not conserved in the alternative targets is the residue pair C673-G676, which is mapped into the M318-G321 pair in Bcr-Abl and the M319-G322 pair in Lck. Thus, this local difference in dewetting propensity, prompted us to conceive and synthesize a methylated variant of imatinib, designated WBZ_4, as well as other related variants. To achieve a higher level of favorable and selective interactivity required an exogenous modulation of the target microenvironment, in turn, requiring a modification of the parental compound. As dictated by the de-wetting blueprint, the added methyl group would promote the favored dehydration of the pair C673-G676 upon binding to C-Kit, while it would hamper the association with Bcr-Abl and Lck, since the latter kinases favor hydration of the catalytic-loop residues aligned with the targeted C-Kit residues C673-G676.

As C-Kit associates with Gleevec, the loop facing the paraposition was found to be unstable. In all five simulation trajectories, the backbone hydrogen bond between Cys673 and Gly676 was irreversibly replaced by water-mediated interactions within 1 ns (FIG. 5). When WBZ_4 replaced Gleevec within the C-Kit complex, the same loop was found to be much more stable due to the improved dehydration of the hydrogen bond by the added methyl group on the ligand. Thus, for C-Kit, WBZ_4 introduces favorable interactions engaging the solvent-exposed preformed hydrogen bond and consequently stabilizes the inhibitor binding. The effect of WBZ_4 is the opposite on Bcr-Abl. Simulations demonstrated that, in this case, the Gleevec complex has a better stability in the same loop region, while WBZ_4 significantly destabilizes the loop. This is due to the fact that the Met318-Gly321 backbone hydrogen bond on the Bcr-Abl loop is well dehydrated intramolecularly and positioned closer to Gleevec, thus this bond is well wrapped by Gleevec and the addition of the methyl group clashes sterically with the loop. Thus, molecular dynamics provides a convincing rationale for the discriminatory power of WBZ_4 relative to Gleevec.

This difference in the ligand-induced dehydration pattern prompted the inventors to redesign imatinib to enhance its capability to protect the vulnerable Cys673-Gly676 hydrogen bond in C-Kit. Thus, WBZ_4 was synthesized, so that the added methyl would contribute to the dehydration of hydrogen bond Cys673-Gly676 upon binding to C-Kit, while it would sterically hinder the ligand association with Bcr-Abl. The specificity filter was validated at the molecular level and further translated into in vivo assays. The decisive tests entailed treating the GIST cell line ST882 (Noma et al., 2005) and the CML cell line K562 (Gambacorti-Passerini et al., 1997) with WBZ_4 and contrasting its inhibitory impact on cell proliferation and in-cell specificity with those associated with imatinib.

B. Biological Assay of WBZ_4

1. Kinetic Studies

The specificity of WBZ_4 towards C-Kit was established first in assays that dissect the kinetics of competitive inhibition (Schindler et al., 2000; Barker et al., 1995) independently of cancer-cell circuitry (Songyang et al., 1995; Clarkson et al., 2003). To determine the enhancement of specificity of WBZ_4 relative to imatinib, kinetic assays of the inhibition of the Bcr-Abl and C-Kit kinase were conducted. The rate of phosphorylation due to kinase activity in the presence of inhibitors, was spectrophotometrically assayed (Schindler et al., 2000; Barker et al., 1995): the adenosine diphosphate production was coupled to the NADH oxidation and determined by absorbance reduction at 340 nm. Reactions were carried out at 35° C. in 500 µl of buffer (100 mM Tris-HCl, 10 mM MgCl$_2$, 0.75 mM ATP, 1 mM phosphoenol pyruvate, 0.33 mM NADH, 95 units/ml pyruvate kinase, pH7.5). Autophosphorylation of the kinase is slow, requiring traces of hematopoietic cell kinase (Hck) to catalyze phosphorylation at sites Tyr393, Tyr412. The reactant concentrations are 10 nM (Bcr-Abl), 12 nM (C-Kit), [ATP]$_o$=10 mM and [phosphorylation substrate]$_o$=0.5 mM. The adopted peptide substrates (Invitrogen/Biaffin) for kinase phosphorylation are: EAIYAAPFAKKK for Tyr412-phosphorylated Bcr-Abl (Songyang et al., 1995; Clarkson et al., 2003), AEEEIYGEFEAKKKKG for unphosphorylated Bcr-Abl (Schindler et al., 2000; Songyang et al., 1995; Clarkson et al., 2003) and KVVEEINGNNYVYIDPTQLPY for Tyr703/Tyr721-phosphorylated C-Kit (Timokhina et al., 1998). The inhibitory impact of imatinib (triangles) and WBZ_4 (squares) on the rate of phosphorylation was determined by spectrophotometry, assaying for the activity of C-Kit and Bcr-Abl (FIG. 6A) (Schindler et al., 2000). These kinetic assays revealed a high specificity of WBZ_4 for C-Kit, in contrast with imatinib. WBZ_4 enhances the inhibition of C-Kit activity beyond imatinib levels, revealing a higher competitive affinity of the prototype compound for the ATP-binding pocket (KI (imatinib)≈55±7 nM; KI (WBZ_4)≈43±5 nM). On the other hand, the pattern of inhibition for Bcr-Abl is dependent on the phosphorylation state of this kinase (Clarkson et al., 2003). At 1 µM concentration, imatinib decreases 66% of the activity of Tyr412-phosphorylated kinase (Schindler et al., 2000) (KI≈5±1 µM) and ~100% of the activity of the unphosphorylated state (KI≈50±5 nM). By contrast, 1 µM WBZ_4 reduces by less than 20% the activity of both states of Bcr-Abl. The prototype compound has reciprocal affinity constants KI≈18±3 µM and KI≈11±2 µM, for phosphorylated and unphosphorylated Bcr-Abl, respectively.

Colorimetric assays were performed over a 1 pM-100 µM range in ligand concentration to assess the inhibition of phosphorylating activity by antibody recognition of phosphorylated peptide substrates. Phosphorylation assays of anti-enzymatic activity of imatinib (STI571) and WBZ_4 against Abl enzyme and C-Kit kinase were performed. Target paralogs EGFR, Chk1 and Pdk were also assayed. The biotinylated substrate peptide (25 µM Abl-tide for Abl or 150 nM Poly (Glu4-Tyr) for C-Kit) in 100 mM sodium bicarbonate buffer (pH=8.0) is coated onto 96-well plates by incubation for 1 hr at room temperature. Subsequently, non-specific binding sites are blocked by incubation with 3% BSA for 1 hr. Phosphorylation of peptide in 96-well plates is initiated by adding of 10 ng Abl or 25 ng c-KIT in assay buffer (20 mM TRIS, pH=7.4, 10 mM MgCl$_2$, 1 mM MnCl$_2$, 0.2 mM ATP, 1 mM dithiothretiol, 25 mM β-glycerol phosphate, 1 mM sodium orthovanadate, 5 mM EGTA). Different concentrations of drug inhibitors are added simultaneously to the wells and incubated for 1 hour at 37° C. Anti-phospho-Abl-tide or anti-phosphotyrosine and anti-rabbit antibodies (dilution 1:1000) are incubated, in consecutive order, for 1 hr at room temperature. The chromophore reaction is initiated by adding TMB, and absorbance at 450 nm is measured 10 min later. Working volume is 100 µl (300 µl for BSA). Washing procedure (PBS 5×300 µl) is performed after each step. The IC$_{50}$ (50%-inhibition concentration) for imatinib/Abl is ~1 µM, while the WBZ_4/Abl value is above 100 µM (FIG. 6B). The active recombinant Abl kinase and its substrate (Abl-tide) were incubated in the presence of various WBZ_4 or imatinib concentrations and ATP (100 nM). Phosphorylation of Abl-tide was detected by spectrophotometry following incubation with anti-rabbit phospho-Abl-tide antibody and subsequently with HRP antibody.

The specificity of the inhibitory impact on C-Kit is significantly enhanced as WBZ_4 substitutes imatinib (FIG. 6A), while C-Kit inhibition is 23±12% greater for WBZ_4 (FIG. 6B). The impact of our prototype ligand on alternative imatinib targets, such as the platelet dependent growth factor receptor (PDGFR) kinase, could not be modulated since such proteins are not reported in PDB and thus, no de-wetting pattern can be reliably identified (cf. high-throughput screening of WBZ_4 versus imatinib in FIGS. 7A and 7B).

2. Cell Culture Assay

To study the inhibitory impact of the variant imatinib methylated at position IV an assay of the inhibitor efficacy was conducted on cell lines derived from a gastro-intestinal stromal tumor (GIST cells), and the potency of the dehydron wrapper was compared with that of the parental compound. The anti tumor activity and efficacy of the compound on ST882 cell lines derived from GIST (gastro-intestinal stromal tumor), known to over-express the C-kit kinase, were studied. GIST cancer cells ST882 ($8 \times 10^3$ cells per well) and CML cells K562 ($1 \times 10^4$ cells per well) were seeded in 96 well plates in 100 µl of RPMI-1640 medium supplemented with 10% FBS and cultured for 24 h. Cells were treated for 48 hrs with 0.01, 0.1, and 1 µM/mL WBZ_4 and imatinib. Cell proliferation was determined by Alamar Blue assay (Bio Source International, Inc, Camarillo, Calif.). Following 48 h of exposure, 50 µl of medium was removed from each well and place into a new 96-well plate. To reach a final volume of 100 µl per well, 40 µl of fresh media and 10 µl of Alamar Blue probe were added. Plates were read at dual wavelength (570-595 nm) in an Elisa plate reader (Kinetic Microplate Reader, Molecular Devices Corporation, Sunnyvale, Calif.).

In addition to achieving higher efficacy as an inhibitor for GIST cells, WBZ_4 possesses higher specificity than the parental compound imatinib. Structural alignment of C-kit and the primary imatinib target, Bcr-Abl kinase (Schindler et al., 2000), reveals that the packing defect Cys673-Gly676 targeted by WBZ_4 is spatially displaced with respect to its corresponding dehydron Gly249-Gln252 in Bcr-Abl. Thus, the substituting methyl group in WBZ_4 is inefficient to wrap the dehydron in Bcr-Abl: the substitution would have to be made elsewhere for that purpose. This structural observation actually translated into virtually no activity of WBZ_4 on Chronic Myeloid Leukemia (CML) cell line K562, an overexpressor of Bcr-Abl, in sharp contrast to imatinib, which possesses antitumor activity on both cell lines.

Figure 8A:
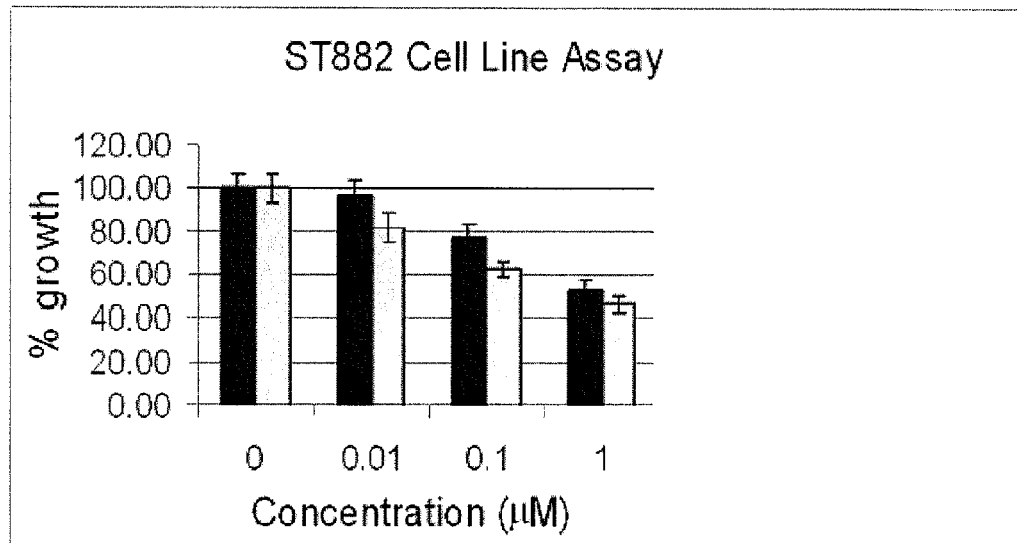
Figure 8B:
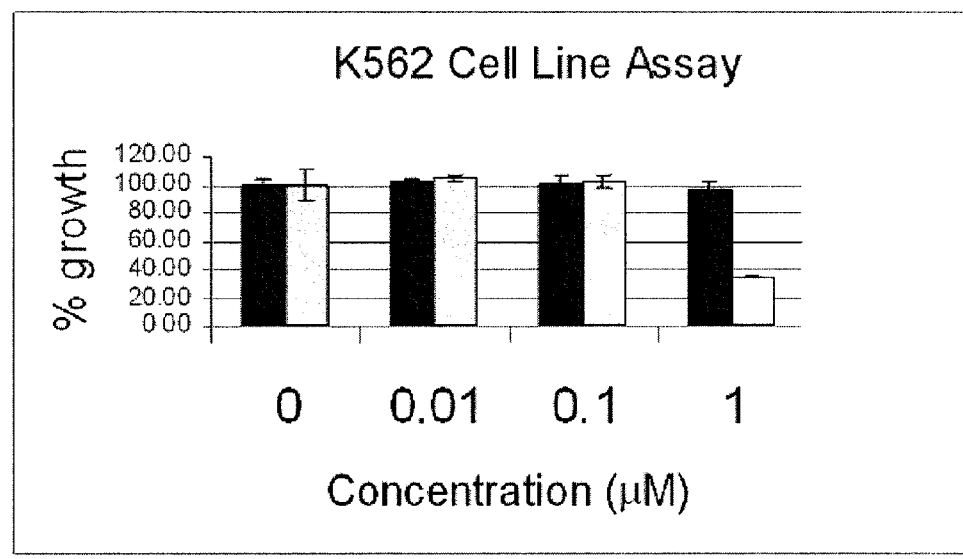

Because of its relative insolubility, WBZ_4 was incorporated into liposomes to promote cellular delivery (Estey et al., 1999). WBZ_4 was dissolved in DMSO was added to 1,2-Dimyristoyl-sn-Glycero-3-Phosphocholine (DMPC) (Avanti) at 1:10 w/w drug/lipid ratio in the presence of excess t-butanol. Tween 20 was added to the mixture in a 1:19 ratio Tween 20:WBZ_4/DMPC. The mixture was vortexed, frozen in an acetone/dry ice bath, and lyophilized. Before adding to cell cultures, this lyophilizate was reconstituted with normal 0.9% NaCl solution. The proliferation of C-Kit-positive ST882 cells treated with WBZ_4 was significantly inhibited in a quantitative dose-dependent manner similar to imatinib, with maximum impact at 1 µM bulk concentration (FIG. 8A). By contrast, the inhibitory impact of WBZ_4 on CML K562 cells at the same bulk physiological dose of 1 µM is almost negligible (cell proliferation less than 10% lower than the proliferation of untreated cells), while 1 µM imatinib promotes a decrease in cell proliferation of approximately 66% (FIG. 8B). These results demonstrate the higher specificity in anti-cancer activity of WBZ_4.

The specificity of the inhibitory impact on C-Kit is dramatically enhanced as WBZ_4 replaces imatinib (FIGS. 6B and 6C), and the C-Kit inhibition is 23±12% greater for WBZ_4 (FIG. 6C). The specificity of WBZ_4 was tested further by assaying for its inhibitory impact against alternative imatinib targets or target paralogs EGFR, Chk1 and Pdk8. No significant inhibition was detected at submilimolar concentrations.

Since imatinib is a micromolar inhibitor of phosphorylated Bcr-Abl (FIG. 6A), the attack on CML cells at 1 µM bulk concentration (growth decrease 63%, FIG. 8B) is attributed to the inhibition of phosphorylated Bcr-Abl (FIG. 8D) combined with the effective nanomolar inhibition of the unphosphorylated form (FIG. 6A). By contrast, WBZ_4 hinders the phosphorylation of Bcr-Abl only partially (FIG. 8D) and in any case, it is an ineffective (micromolar) inhibitor of both forms of Bcr-Abl (FIG. 6A). Hence, its anti-tumor activity is predictably minimal on CML cells (FIG. 8B). In the case of GIST cells, comparable anti-tumor activity of both compounds (FIG. 8A) is likely to arise from comparable inhibitory impact (~85%, FIG. 8C) on CKit phosphorylation, and the fact that both compounds are nanomolar-affinity inhibitors of C-Kit (FIG. 6A).

Figure 8C:
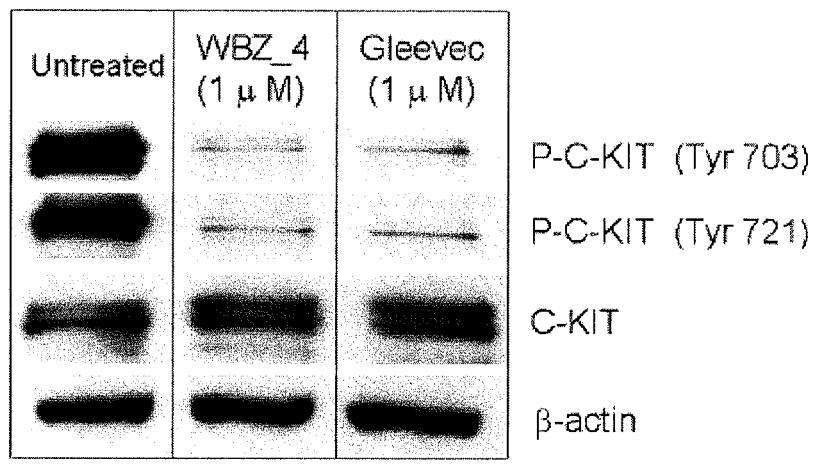
Figure 8D:
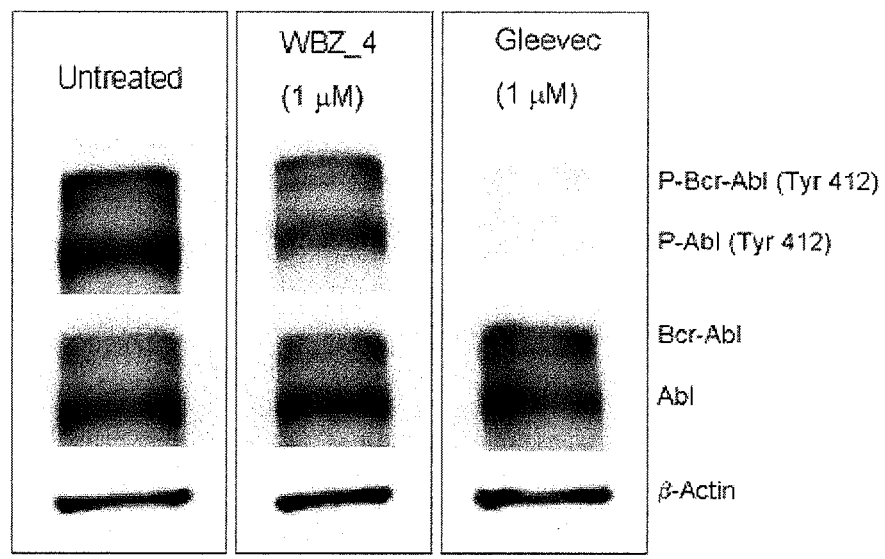

A Western blot assay on treated cancer-derived cell lines (FIGS. 8C and 8D) was performed to determine the in-cell specificity of WBZ_4. ST-882 cells were plated at $2.5 \times 10^5$ cells/well in 6-well plates in RPMI-1640 medium supplemented with 10% FBS. After allowing the cells to attach for 24 hours, the cells were treated with 1 µM of WBZ_4 or Gleevec for 6 hours. For Western blotting, 50 µg of total protein were separated on a SDS-PAGE (Bio-Rad) and blotted onto nitrocellulose membranes (Bio-Rad Laboratories, Life Science Research, Hercules, Calif.). Antibodies used: anti phospho-c-Kit polyclonal antibody, Tyr703 and Tyr721 (Zymed Laboratories Inc., South San Francisco, Calif.), anti-c-Kit monoclonal antibody (E-1): sc-17806 (Santa Cruz Biotechnology) and anti β-actin monoclonal antibody (Sigma, St. Louis, Mo.). K562 cells were plated at $5 \times 10^5$ cells/well. Two hours later, the cells were treated for 6 hours with 1 µM WBZ_4 and imatinib. Antibodies used: anti phospho-c-Abl (Tyr 412) monoclonal antibody 247C7 (Cell Signalling Technology Inc), anti-Abl monoclonal antibody (Sigma, St. Louis, Mo.). The immunoblots revealed specificity towards C-Kit consistent with the selective anticancer activity on the GIST882 cell line that expresses C-Kit. Thus, the activating phosphorylation of C-Kit at sites Tyr703 and Tyr721 in ST882 cells is inhibited by WBZ_4 in a dose-sensitive manner similar to imatinib (FIG. 8C). By contrast, phosphorylation of Bcr-Abl at Tyr 412 (Dorey et al., 2001) in K562 cells was not significantly inhibited (<15%) by WBZ_4, while densitometry revealed a imatinib-induced inhibition of ~85% (FIG. 8D).

3. Animal Studies

To study WBZ_4 for anticancer activity in vivo, an animal model for GIST growth based on female C.B-17/IcrHsd-Prkdc$^{SCID}$ mice was developed de novo. The model involved the subcutaneous injection of GIST882 cells (Prenen et al., 2006). The efficacy of WBZ_4 was found to be comparable to that of imatinib, as determined by the decrease in tumor volume and weight (FIGS. 9A and 9B). No obvious toxicities were observed in the animals during treatment as determined by behavioral changes, such as eating habits and mobility. Furthermore, mouse weights were not significantly different among the three groups of animals, suggesting that eating and drinking were not affected. Selectivity of WBZ_4 in the animal model using female C.B-17/IcrHsd-Prkdc$^{SCID}$ was corroborated by assaying on the xenograft induced by CML cells K562 (FIG. 9C). While imatinib is shown to significantly impair tumor growth (p<0.01), the prototype WBZ_4 has virtually no effect, in accord with its engineered specificity and hence lack of inhibitory impact on Bcr-Abl kinase.

These studies have been approved by the Institutional Animal Care and Utilization Committee, University of Texas—M. D. Anderson Cancer Center. Female C.B-17/IcrHsd-Prkdc$^{SCID}$ mice were purchased from the Harlan Sprague Dawley, Inc. (Indianapolis, Ind.) and housed in facilities approved by and in accordance with the American Association for Accreditation of Laboratory Animal Care, the United States Department of Agriculture, the United States Department of Health and Human Services, and the National Institutes of Health. Mice were used according to institutional guidelines when they were 8-12 weeks of age. GIST882 cells (Prenen et al., 2006) were harvested from subconfluent cultures by a brief exposure to 0.25% trypsin-EDTA (Invitrogen, Carlsbad, Calif.). Trypsinization was stopped with medium containing 10% FBS. The cells were then washed twice in serum-free medium and re-suspended in serum-free Hank's balanced salt solution (Invitrogen). Single-cell suspensions with greater than 95% viability, as determined by Trypan blue exclusion, were used for the injections. To produce tumors, $6\times10^6$ GIST882 cells per 100 μl were injected subcutaneously into the unilateral flank of each SCID mouse. Five mice per group in the vehicle and imatinib groups and seven mice in the WBZ__4 group were used.

Once tumors were palpable (11 weeks from injection), mice were started on therapy with daily intraperitoneal injections of normal saline (vehicle), imatinib (50 mg/kg), or liposomal WBZ__4 (50 mg/kg). Treatment was continued for 6 weeks with weekly 2-dimensional measurements of tumor size. All mice were sacrificed when the tumor size approached 1.5 cm in the control group. Tumors were collected, fixed in formalin, and analyzed by hematoxylin and eosin (H&E) staining. Representative images were taken from each tumor using a light microscope at 40× and 100× magnification.

For the K562 model, tumor cells were collected from subconfluent suspensions, as described above. To produce tumors, $1\times10^7$ K562 cells per 100 μl were injected subcutaneously into the unilateral flank of each SCID mouse. Once tumors were palpable (2 weeks after injection), the mice were then randomized into the following groups (n=7 per group): (1) normal saline (NS) daily, (2) empty liposomes daily, (3) imatinib (doses listed above), and (4) WBZ__4 (doses listed above). Treatment continued until mice in any of the groups developed large tumor burden, at which point, all animals were sacrificed. Tumors were measured weekly during treatment, and at necropsy.

Liposomal WBZ__4 was prepared for in vivo testing. WBZ__4 and 1,2-Dimyristoyl-sn-Glycero-3-Phosphocholine (DMPC) (Avanti Polar Lipids Inc, Alabaster, Ala.) were mixed in excess tert-butanol (Sigma, St. Louis, Mo.) in a 1:10 molar concentration. Tween-20 (Sigma, St. Louis, Mo.) was also added to the mixture. Following a quick freeze in a dry ice-acetone water bath, the mixture was lyophilized for 24 h. The liposomes were stored at −20° C. until ready to use. Immediately before each treatment, the liposomes were reconstituted in normal saline.

Continuous variables were compared with either the Student t-test or analysis of variance (ANOVA). Prior to analysis, all distributions were examined for outliers and non-normality. If appropriate, nonparametric tests (Mann-Whitney test) were utilized to compare differences. All statistical analyses were performed with SPSS (SPSS, Inc.). $P<0.05$ was considered statistically significant.

4. Cardiotoxicity

As previously noted, studies of imatinib-induced cardiotoxicity identified a protective JNK (JNK1) inhibition as a means to reduce the collapse of mitochondrial membrane potential (Kerkela et al., 2006). The inventors tested the molecular harnessing of WBZ__4 on the de-wetting pattern of JNK1 (PDB.2G01). This analysis required alignment of JNK1 with the imatinib-C-Kit complex (PDB.1T46) (FIG. 10). The high de-wetting propensity at JNK1 residue M111, the residue that aligns with C673 in C-Kit, instills confidence in the affinity of WBZ__4 for JNK.

Also, WBZ__4 was screened for affinity against a T7-bacteriophage library displaying 228 human kinases (Ambit Biosciences) (Fabian et al., 2005), using imatinib screening as control. The selective affinity of WBZ__4 for C-Kit kinase and JNK1 is noteworthy. Predictably, the affinity of WBZ__4 for ABL1 is reduced by 75% and by 95% or more on all other ABL variants, while, in contrast with imatinib, WBZ__4 shows no detectable affinity for Lck. The impact of WBZ__4 on all additional imatinib targets was comparable, while its controlled specificity is apparent.

This protective role of WBZ__4 has also been validated in vivo. Animals used in these studies were handled in accordance with National Institutes of Health "Guide for the Care and Use of Laboratory Animals" [Department of Health and Human Services Publication No. (NIH) 85-23, Revised 1985]. Cell extracts from imatinib and WBZ__4 treated cardiomyocites where evaluated by Western blots probed with antibodies specific for the phosphorylated forms of ERKs, JNKs or p38$^{MAPK}$. NRVM were isolated from the hearts of 2 day-old Sprague-Dawley rat pups via collagenase digestion as previously described (Samarel and Engelmann, 1991). Dissociated cells were pre-plated for 1 hour in serum-free PC-1 medium to selectively remove nonmuscle cells. Myocytes were then plated in PC-1 medium at a density of 1600 cells per mm$^2$ onto collagen-coated, plastic 35-mm dishes, and left undisturbed in a 5% $CO_2$ incubator for 24 h. Unattached cells were removed by aspiration, and the attached cells were maintained in a solution of DMEM/Medium 199 (4:1) containing antibiotic/antimycotic solution for 24 h. Thereafter, cells were maintained in control medium, or treated with imatinib or WBZ__4 (1-50 μM, 24 h). NRVM were homogenized in lysis buffer (Schlaepfer and Hunter, 1996). Equal amounts of extracted proteins were separated on 10% SDS-polyacrylamide gels with 5% stacking gels. Proteins were transferred to nitrocellulose membranes, and the Western blots probed with antibodies specific for the phosphorylated forms of ERKs, JNKs or p38$^{MAPK}$. To ensure equal loading, membranes were also probed with an antibody specific for GAPDH. Primary antibody binding was detected with horseradish-peroxidase conjugated goat anti-mouse or goat anti-rabbit secondary antibody, and visualized by enhanced chemiluminescence. Western blotting of cell extracts derived from imatinib- and WBZ__4-treated cardiomyocytes (FIG. 11A) revealed that both drugs increased the phosphorylation state of ERK1/2 and p38$^{MAPK}$ as compared to untreated cultures. In contrast, cells treated with WBZ__4 showed reduced levels of JNK1/2 activation at each concentration tested, as compared to untreated cells, or cells treated with imatinib. The results confirm the recent observations of Kerkela et al. (2006) demonstrating that imatinib induces the endoplasmic reticulum (ER) stress response and activates JNKs in neonatal rat ventricular myocytes (NRVM).

A direct inhibitory effect on INK activity would predict that WBZ__4 should have reduced cardiotoxicity in vivo. This expectation is indeed supported by observations using the surrogate marker brain natriuretic peptide (BNP), a most sensitive indicator of myocardial hypertrophy and cardiac impairment (Scheuermann-Freestone et al., 2001). The expected curbing of cardiotoxicity in WBZ__4 anticancer therapy was confirmed by examining the mRNA levels of BNP in the left ventricle of mice from the same groups assayed for anticancer activity. Total RNA was extracted from mouse heart samples using the RNeasy™ kit (Qiagen) according to the manufacturer's instructions. The mRNA levels of BNP were examined in the left ventricle of mice from a GIST animal model groups treated exclusively with either WBZ__4 or imatinib. The reverse transcription polymerase chain reaction (RT-PCR) was performed as described previously (Thaker et al., 2006). The primer sequences are as follows: BNP, 5'-AGCTGCTGGAGCTGATAAGA-3' (FWD) (SEQ ID NO:8) and 5'-TTACAGCCCAAACGACT-GAC-3' (REV) (SEQ ID NO:9) (Baines and Molkentin, 2005); β-actin, 5'-ATCTGGCACCACACCTTCTACA-ATGA-3' (FWD) (SEQ ID NO:10) and 5'-CGTCATACTC-CTGCTTGCTGATCCAC (REV) (SEQ ID NO:11). The BNP mRNA levels were about 58% higher in the ventricles from imatinib-treated animals (FIG. 11B), while no significant difference was detected in the WBZ_4-treated animals when compared with untreated mice.

Finally, the reduced cardiotoxicity of WBZ_4 was directly tested in mice by determination of the percentage ejection fraction (EF) in the left ventricle by magnetic resonance (MR) imaging of treated mice subject to imatinib or WBZ_4 therapy (FIG. 11C). Assessment of left ventricular function was performed as previously described (Thaker et al., 2006). In brief, representative in vivo axial images of the left ventricle in diastole and systole of control and test mice were acquired in a 4.7T MR scanner cardiac gating using a magnetization-prepared spoiled gradient echo sequence. To assess cardiac function, short axis cardiac cine images were acquired using a magnetization prepared, cardiac-gated spoiled gradient echo sequence (TE/TR 2.1 ms/~23.5 ms; 16 phases covering 1.5 R—R cycles; in-plane resolution 312 μm×312 μm; 1.25 mm slice thickness). For assessing EF, regions of interest encompassing the cavity of the left ventricle were drawn. For each animal, the average region of interest of four central slices in systole was divided by the average region of interest of four central slices in diastole taken at the same location in the left ventricle to derive the EF. Following 6 weeks of therapy, the cardiac EF was significantly lower in the imatinib group compared to controls (p=0.02), which is consistent with previous findings (Kerkela et al., 2006). Remarkably, WBZ_4 treatment had no effect on cardiac EF despite prolonged therapy (FIG. 11C).

Example 2

Ligand Design of a Bcr-Abl Inhibitor Based on Imatinib (Gleevec)

The evolutionary proximity of kinases fosters side effects arising from off-target ligand binding. Making use of the wrapping concept, the inventors have reported on how to sharpen the binding affinity within the pharmacokinome associated with a specific drug (Fernandez, 2005). Thus, the selective inhibition of the Bcr-Abl (Abelson tyrosine kinase), a major target in the treatment of chronic myeloid leukemia (CML, Schindler et al., 2000), was corroborated in biological assays using a re-designing imatinib (Schindler et al., 2000). Imatinib inhibits the Bcr-Abl tyrosine kinase, the constitutive abnormal tyrosine kinase created by the Philadelphia chromosome abnormality in chronic myeloid leukemia (CML). It inhibits proliferation and induces apoptosis in Bcr-Abl positive cell lines as well as fresh leukemic cells from Philadelphia chromosome positive chronic myeloid leukemia (FIG. 12). In colony formation assays using ex vivo peripheral blood and bone marrow samples, imatinib shows inhibition of Bcr-Abl positive colonies from CML patients. In vivo, it inhibits tumor growth of Bcr-Abl transfected murine myeloid cells as well as Bcr-Abl positive leukemia lines derived from CML patients in blast crisis. In vitro studies demonstrate that imatinib is not entirely selective; it also inhibits the receptor tyrosine kinases for platelet-derived growth factor (PDGF) and stem cell factor (SCF), c-Kit, and inhibits PDGF- and SCF-mediated cellular events. Of the alternative imatinib targets with reported structure, the C-kit tyrosine kinase has been recognized as a binding partner (Attoub et al., 2002; Skene et al., 2004). In addition, imatinib binds tightly to the lymphocyte kinase (Lck) (Fabian et al., 2005). Thus, the inventors sought to modify imatinib to improve its selectivity for Bcr-Abl by turning the ligand into a wrapper of dehydrons Gly249-Gln252, Gln300-Glu316, not conserved across the PDB-reported paralogs of Bcr-Abl. Thus, methylation at positions I and II improves the wrapping of dehydrons 249-252 and 300-316, respectively, and dramatically enhanced the selectivity of the dehydron wrapper towards Bcr-Abl when compared with the parental compound (Fernandez, 2005). Methylation at position III might enhance the wrapping of (271-286) salt bridge but since this salt bridge is extremely conserved across kinases, this substitution would do nothing to improve selectivity for Bcr-Abl. The enhanced selectivity of the I, II-methylated prototype has been corroborated by performing a spectrophotometric assay of the extent of inhibition of the phosphorylation rates for the set of imatinib targets (FIG. 13).

In vitro kinase assays are conducted to determine the activity of the modified inhibitors. All compounds synthesized are screened and those with the best inhibitory activity are assessed further. Logarithmic doses of the modified inhibitors are used to determine the $ID_{50}$. The time of incubation is based on previous reports where the parental compound had been used. In the case of the modified imatinib analogs, the $ID_{50}$, typically, is determined at 48 hours. Based on the $ID_{50}$ obtained, other time points are assessed (e.g., 12, 24, 48, 72 and 96 hours). Having established the duration of the incubation, a dose respond experiment is conducted to determine an optimal dose. After exposure to the modified inhibitors, the reversibility of the effects on cells is determined. This establishes the capacity of the cells to recover and proliferate as normal once the medium containing the compounds are replaced with medium not containing the compounds of interest.

The compound WBZ_1 is a modified inhibitor obtained by adding only a methyl group to imatinib at position I. The addition of this group targets a wrapping defect that is only present in the Bcr-Abl fusion protein and not in other paralogs. This modification should lead to a selective inhibition of the Bcr-Abl kinase, and indeed it does. Due to the apparent WBZ_1 insolubility, the prototype compound was incorporated into a lipid carrier containing 1,2-Dimyristoyl-sn-Glycero-3-Phosphocholine (DMPC). In order to determine the best lipid formulation to be used, the inventors tested different WBZ_1:MDPC ratios. Liposomal-WBZ_1 formulations were tested in K562 cells, a CML cell line known to have the Bcr-Abl fusion protein and to be sensitive to imatinib in vitro. Cell proliferation inhibition was determined by Alamar blue assay after 48 hours of incubation and calculated as percentage of inhibition comparing with the untreated control. All formulations were nontoxic for the cells and a dose response curve was observed. The effective concentration ranges between 0.1 and 1 μM regardless of the lipid:drug ratio used. Based on previous experiments (Tani et al., 1995) the uptake of WBZ_1 after 48 hours should have been 72 pmoles. DMSO solubilized WBZ_1 was compared to the lipid based WBZ_1.

Example 3

Engineering of Staurosporine

Perhaps the most stringent test on the feasibility of engineering selectivity by designing a wrapping ligand involves modifying staurosporine, the most promiscuous kinase ligand available (Hopkins, Mason and Overington, 2006). The aim here is to elicit a selective inhibitory impact that distinguishes packing differences across its multiple targets.

Thus, four PDB-reported staurosporine-binding kinases with significant pairwise packing distances (>0.4) and extremely low staurosporine-based pharmacological distance (<0.01) are considered: Src kinase (PDB.1BYG), CDK2 (PDB.1AQ1), Chk1 (PDB.1NVR) and PDK1 (PDB.1OKY). Wrapping analysis reveals that only the Src kinase possesses a nonconserved dehydron, the backbone hydrogen bond Gln250-Glu267, that may be wrapped by methylating staurosporine at the imide N6-position of the indole ring.

Upon structural alignment, the Src dehydron maps into well-wrapped backbone hydrogen bonds: Lys65-Glu81 in CDK2, Lys69-Glu85 in Chk1 and Lys144-Ser160 in PDK1. Thus, it was predicted that selectivity for Src kinase may be achieved by redesigning staurosporine to turn it into a wrapper of the Gln250-Glu267 dehydron, a packing defect not conserved in alternative targets CDK2, Chk1 and PDK1, of the parental compound.

The chemical modification of staurosporine (Link et al., 1995; Bregman et al., 2004; Knoelker and Reddy, 2002) entails replacing the imide hydrogen in the indole ring with a methyl group, a substitution known to severely impair the capacity of the ligand to become engaged as donor in an intermolecular hydrogen bond with the ATP pocket. Methylation at indole N6 may be achieved by two routes: a) Recapitulating the staurosporine synthesis using methyl substitution on the indole N6 as protective group, and retaining the substitution throughout the synthesis; b) using staurosporine as starting point and methylating with NaH/DMF (sodium hydride/dimethyl formamide) with prior protection of alternative N-methylation sites (Knoelker and Reddy, 2002). The latter route was selected for simplicity.

To assess the specificity and affinity for Src, the staurosporine derivative is compared with the parental compound. Kinase packing defects around the ligand indole region in staurosporine-kinase complexes show a microenvironment of dehydron Gln250-Glu267 in Src kinase is framed by the desolvation spheres centered at the α-carbons of Gln250 and Glu267. Methylation at the indole N5-position would turn the ligand into a wrapper of the nonconserved packing defect in Src kinase. Wrapping environment of the intramolecularly dehydrated backbone hydrogen bond Lys65-Glu81 in CDK2 aligns with dehydron Gln250-Glu267 in Src kinase. The Lys65-Glu81 backbone hydrogen bond in CDK2 that aligns with the 250-267 dehydron in Src kinase is actually an intramolecularly well-packed hydrogen bond. Kinetic spectrophotometric assays where performed as indicated above. These assays were geared at measuring the phosphorylation rate of peptide substrates in the presence of the kinase inhibitor at different concentrations. The inhibition of Src by the drug-wrapper of dehydron Gln250-Glu267 improved when compared with staurosporine (Sigma-Aldrich) levels (FIG. 14).

Furthermore, the inhibitory impact of the ligand-wrapper in the form of a methylated staurosporine derivative became selective for Src vis-à-vis CDK2, Chk1, and PDK1. Dehydron Gln250-Glu267 is either absent or well-wrapped in the latter PDB-reported kinases, and consistently, the drug designed to better wrap this dehydron has very low inhibitory impact against the other PDB-reported paralog kinases. Thus, the inventors have shown that packing differences across protein paralogs may be taken into account to achieve specificity by suitably modifying even the most promiscuous kinase inhibitor.

REFERENCES

The following references, to the extent that they provide exemplary procedural or other details supplementary to those set forth herein, are specifically incorporated herein by reference.

U.S. Pat. No. 4,186,183
U.S. Pat. No. 4,217,344
U.S. Pat. No. 4,235,871
U.S. Pat. No. 4,261,975
U.S. Pat. No. 4,485,054
U.S. Pat. No. 4,501,728
U.S. Pat. No. 4,603,044
U.S. Pat. No. 4,623,486
U.S. Pat. No. 4,623,486
U.S. Pat. No. 4,737,323
U.S. Pat. No. 4,774,085
U.S. Pat. No. 4,837,028
U.S. Pat. No. 4,946,787
U.S. Pat. No. 4,957,773
U.S. Pat. No. 5,145,684
U.S. Pat. No. 5,399,363
U.S. Pat. No. 5,466,468
U.S. Pat. No. 5,534,499
U.S. Pat. No. 5,543,158
U.S. Pat. No. 5,552,157
U.S. Pat. No. 5,565,213
U.S. Pat. No. 5,567,434
U.S. Pat. No. 5,580,579
U.S. Pat. No. 5,641,515
U.S. Pat. No. 5,725,871
U.S. Pat. No. 5,738,868
U.S. Pat. No. 5,741,516
U.S. Pat. No. 5,756,353
U.S. Pat. No. 5,780,045
U.S. Pat. No. 5,792,451
U.S. Pat. No. 5,795,587
U.S. Pat. No. 5,804,212
U.S. Pat. No. 5,820,873
U.S. Pat. No. 5,885,613
U.S. Pat. No. 5,976,567
U.S. Pat. No. 6,027,726
U.S. Pat. No. 6,320,017
U.S. Patent Prov. Ser. 60/571,712.
U.S. Publication 20040102472A1
U.S. Publication 20040248918A1
Abra et al., *J. Liposome Res.,* 12:1-3, 2002.
Allen and Chonn, *FEBS Lett.,* 223(1):42-46, 1987.
Allen, et al., *Biochim. Biophys. Acta.,* 1237(2):99-108, 1995.
Attoub et al., *Cancer Res.,* 62:4879-4883, 2002.
Bain et al., *Biochem. J.,* 371(Pt 1):199-204, 2003.
Bain et al., *Biochem. J,* 371:199-204, 2000.
Barker et al., *Biochemistry,* 34:14843-14851, 1995.
Benavides et al., *Optics Express,* 11:1223-1236, 2003.
Beran et al., *Clin. Cancer Res.,* 4(7):1661-1672, 1998.
Bloomfield, *Ann. Rev. Biophys. Bioeng.,* 10:421-450, 1981.
Blume, et al., *Biochim. Biophys. Acta.,* 1149(1):180-184, 1993.
Bregman et al., *J. Am. Chem. Soc.,* 126:13594-13595, 2004.
Brooks and Karplus, *J. Mol. Biol.,* 208:159, 1989.
Brooks et al., *J. Comput. Chem.,* 4:187-217, 1983.
Brown et al., *Nat. Cell Biol.,* 1(7):438-443, 1999.
Chandran et al., *Indian J. Exp. Biol.,* 35(8):801-809, 1997.
Chen et al., *Bioinformatics,* 23:563-572, 2007.
Cheng et al., *J. Biol. Chem.,* 267:9248-9256, 1992.
Clarkson et al., *Leukemia,* 17:1211-1262, 2003.
Collier et al., *Academic Radiology,* 9(5): 504-512, 2002.
Collier et al., *Optics Express,* 6(2): 40-48, 2000.
Couvreur et al., *Pharm. Res.,* 8(9):1079-1086, 1991.
Couzin, *Science,* 307:1711, 2005.
Dan et al., *Cell Death Differ.,* 5(8):710-715, 1998.
Deamer and Bangham, *Biochim. Biophys. Acta.,* 443:629-634, 1976.

Delaney and Harris, Fiber Optics in Confocal Microscope, in Handbook of Confocal Microscopy, J. B. Pawley, Editor, Plenum Press: New York. p. 515-523, 1995.
DeMatteo, *Ann. Surg. Oncol.*, 9(9):831-39, 2002.
Deremble and Lavery, *Curr. Opin. Struc. Biol.*, 15:171-75, 2005.
Donato and Talpaz, *Clin. Cancer Res.*, 6:2965-66, 2000.
Dorey et al., *Oncogene*, 20:8075-8081, 2001.
Drezek et al., *Am. J. Obstet. Gynecol.*, 182(5):1135-1139, 2000.
Druker, *Oncologist*, 9:357-360, 2004.
Estey et al., *Blood*, 94(7):2230-2235, 1999.
Fabian et al., *Nature Biotechnology*, 23:329-336, 2005.
Faderl et al., *N. Engl. J. Med.*, 341:164-172, 1999.
Fernández and Berry, *Proc. Natl. Acad. Sci. USA*, 101:13460-13465, 2004.
Fernández and Scheraga, *Proc. Natl. Acad. Sci. USA*, 100: 113-118, 2003.
Fernández and Scott, *Biophys. J.*, 85:1914-1928, 2003b.
Fernández and Scott, *Phys. Rev. Lett.*, 91:018102, 2003a.
Fernández et al., *Proc. Natl. Acad. Sci. USA*, 101:11640-11645, 2004.
Fernández, *Nature Biotechnol.*, 22:1081-1084, 2004.
Fernández, *Structure*, 13:1829-1836, 2005.
Fraley et al., *Proc. Natl. Acad. Sci. USA*, 76:3348-3352, 1979.
Gabizon and Papahadjopoulos, *Proc. Natl. Acad. Sci. USA*, 85(18):6949-6953, 1988.
Gambacorti-Passerini et al., *Blood Cells Mol. Dis.*, 23(3): 380-394, 1997.
Heath, In: *Covalent Attachment of Proteins to Liposomes*, Methods in Enzymology, 111-119. Academic Press, Inc., 1987.
Hirahata et al., *Gan To Kagaku Ryoho.*, 19(10 Suppl):1591-1594, 1992.
Hope, et al., *Biochim. Biophys. Acta*, 812:55-65, 1985.
Hope, et al., *Chem. Phys. Lip.*, 40:89, 1986.
Hopkins et al., *Curr. Opin. Struct. Biol.*, 16:127-136, 2006.
Hopkins, Mason and Overington, *Curr. Opin. Struct. Biol.*, 16(1):127-136, 2006.
Jones et al., *J. Mol. Biol.*, 267:727, 1997.
Jorgensen, *J. Am. Chem. Soc.*, 103:335-340, 1981.
Kellenberger et al., *Proteins*, 57:225, 2004.
Kerkela et al., *Nature Medicine*, 12:908-916, 2006.
Kirpotin et al., *Biochemistry*, 36(1):66-75, 1997.
Knight and Shokat, *Chem. Biology*, 12:621-637, 2005.
Knölker and Reddy, *Chem. Rev.*, 102:4303-4427, 2002.
Kramer et al., *Proteins*, 37:228, 1999.
Kuntz et al., *J. Mol. Biol.*, 161:269, 1982.
Lasic, *Trends Biotechnol.*, 16(7):307-321, 1998.
Le Good et al., *Science*, 281:2042-2045, 1998.
Leonetti, et al., *Proc. Natl. Acad. Sci., USA*, 87:2448-2451, 1990.
Levitski and Gazit, *Science*, 267:1782-1788, 1995.
Li et al., In: *Contemporary Drug Synthesis*, Wiley Interscience, Hoboken, N.J., 2004.
Li, In: *Molecular Evolution*, Sinauer Associates Publishers, Sunderland, Mass., 1997.
Liang et al., *Applied Optics*, 41(22): 4603-4610, 2002.
Link et al., *J. Am. Chem. Soc.*, 117:552-553, 1995.
Liposomes, Marc J. Ostro, ed., Marcel Dekker, Inc., New York, Chapter 1, 1983.
Liposomes: A Practical Approach, Torchilin, V. P. et al., ed., Oxford University Press, 2003.
Ma and Karplus, *J. Mol. Biol.*, 274:114-131, 1997b.
Ma and Karplus, *Proc. Natl. Acad. Sci. USA*, 94:11905-11910, 1997a.
Ma et al., *Proc. Natl. Acad. Sci. USA*, 100:5772-5777, 2003.
Ma et al., *Proc. Natl. Acad. Sci. USA*, 95:14640, 1998.
Manning et al., *Science*, 298:1912-1934, 2002.
Margalit, *Crit. Rev. Ther. Drug Carrier Syst.*, 12(2-3):233-261, 1995.
Marshall, *Cell*, 80:179-185, 1995.
Mathiowitz et al., *Nature*, 386(6623):410-414, 1997.
Mayer, et al., *Biochim. Biophys. Acta*, 858:161-168 (1986)
McGary et al., *Clin. Cancer Res.*, 8(11):3584-3591, 2002.
Mol et al., *J. Biol. Chem.*, 279:31655-31663, 2004.
Morishita et al., *Proc. Natl. Acad. Sci. USA*, 90(18):8474-8478, 1993.
National Institutes of Health "Guide for the Care and Use of Laboratory Animals" Dept of Health and Human Services Publication No. (NIH) 85-23, Revised 1985.
Neria et al., *J. Chem. Phys.*, 105:1902-1921, 1996.
Noma et al., *Oncol. Rep.*, 14(3):645-650, 2005.
Park and Levitt, *J. Mol. Biol.*, 258:367, 1996.
Park et al., *Optics Express*, 13:749-762, 2005.
Patel et al., *Cell Signal.*, 17(9):1098-1110, 2005.
PCT Appln. WO/03027100
PCT Appln. WO/2004108699
PCT Appln. WO/91/1 7424
PCT Appln. WO/03027100A1
PCT Appln. WO/2004108699A1
Perlmutter et al., *J. Cell. Biochem.* 38:117-126, 1988.
Pinto-Alphandary et al., *J. Drug Target*, 3(2):167-169, 1995.
Pluk et al., *Cell*, 108(2):247-259, 2002.
Prenen et al., *Anticancer Res.*, 26:1247-1252, 2006.
Quintanar-Guerrero et al., *Pharm. Res.*, 15(7):1056-1062, 1998.
Rajadhyaksha et al, *J. Invest. Dermatology*, 117(5):1137-1143, 2001a.
Rajadhyaksha et al., *Applied Optics*, 38(10): 2105-2115, 1999a.
Rajadhyaksha et al., *J. Invest. Dermatology*, 113(3): 293-303, 199b.
Rajadhyaksha et al., *J. Invest. Dermatology*, 104(6): 946-952, 1995.
Rajadhyaksha et al., *Optics & Photonics News*, 30, 2001b.
Remington's Pharmaceutical Sciences, 15th ed., pages 1035-1038 and 1570-1580, Mack Publishing Company, Easton, Pa., 1980.
Remington's Pharmaceutical Sciences, 18th Ed. Mack Printing Company, 711, 1990.
Remington's Pharmaceutical Sciences, 18th Ed. Mack Printing Company, pp. 1545-1569, 1990.
Samarel and Engelmann, *Am. J. Physiol.*, 261:H1067-1077, 1991.
Sapra and Allen, *Prog. Lipid Res.*, 42(5):439-62, 2003.
Schellhammer and Rarey, *Proteins*, 57:504, 2004.
Scheuermann-Freestone et al., *Eur. J. Heart Fail.*, 3:535-543, 2001.
Schindler et al., *Science*, 289:1938-1942, 2000.
Schlaepfer and Hunter, *Mol. Cell. Biol.*, 16:5623-5633, 1996.
Selkin et al., *Dermatologic Clinics*, 19(2):369-377, 2001.
Shoichet et al., *Science*, 259:1445, 1993.
Skene et al., *J. Biol. Chem.*, 279:31655-31663, 2004.
Songyang et al., *Nature*, 373:536-39, 1995.
Sung et al., *IEEE Transactions on Biomedical Engineering*, 49(10): 1168-1172, 2002b.
Sung et al., *J. Microscopy*, 207(Pt) 2: 137-145, 2002a.
Szoka et al., *Ann. Rev. Biophys. Bioeng.*, 9:467, 1980.
Takakura, *Nippon Rinsho.*, 56(3):691-695, 1998.
Takenaga et al., *J. Control Release*, 52(1-2):81-87, 1998.
Tanis et al., *J. Med. Chem.*, 39:5053-5063, 1996.
Taylor et al., *J. Comput. Aided Mol. Des.*, 16:151, 2002.
Thaker et al., *Nature Medicine*, 12:939-944, 2006.

Tibes et al., *Annu. Rev. Pharmacol. Toxicol.*, 45:357-384, 2005.
Timokhina et al., *EMBO J.*, 17:6250-6262, 1998.
Wang and Wang, *J. Chem. Inf. Comput. Sci.*, 41:1422, 2001.
Wang et al., *Cancer Biother. Radiopharm.*, 20(5):547-556, 2005.
Wang et al., *Molecular Imaging*, 3:343-351, 2004.
White et al., *Laryngoscope*, 109(10):1709-1717, 1999.
Williams, et al., *Proc. Natl. Acad. Sci. USA*, 85:242-246, 1988.
Zalipsky, *Bioconjug Chem.*, 6(6):705-708, 1995.
Zalipsky, *FEBS Lett.*, 353(1):71-74, 1994.
Zhang et al., *Protein Sci*, 13:400, 2004.
Zhao et al., *Proc. Natl. Acad. Sci. USA*, 99:14795-14800, 2002.
zur Muhlen et al., *Eur. J. Pharm. Biopharm.*, 45(2):149-155, 1998.

---

What is claimed is:

1. A protein ligand represented by the following structural formula:

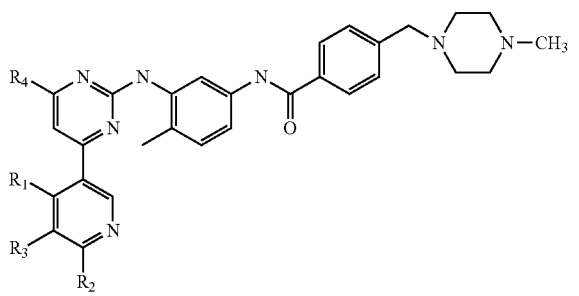

and stereoisomers and pharmaceutically acceptable salts thereof, wherein:
(a) R1 is hydrogen, alkyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl;
(b) R2 is hydrogen, alkyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl;
(c) R3 is hydrogen, alkyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl; and
(d) R4 is hydrogen, alkyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl
wherein at least one of R1, R2, R3 or R4 is not hydrogen.

2. The ligand of claim 1, wherein:
(a) R1 is alkyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl;
(b) R2 is hydrogen;
(c) R3 is hydrogen; and
(d) R4 is hydrogen.

3. The ligand of claim 1, wherein:
(a) R1 is hydrogen;
(b) R2 is alkyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl;
(c) R3 is hydrogen; and
(d) R4 is hydrogen.

4. The ligand of claim 1, wherein:
(a) R1 is hydrogen;
(b) R2 is hydrogen;
(c) R3 is alkyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl; and
(d) R4 is hydrogen.

5. The ligand of claim 1, wherein:
(a) R1 is hydrogen;
(b) R2 is hydrogen;
(c) R3 is hydrogen; and
(d) R4 is alkyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl.

6. The ligand of claim 1, wherein the ligand is:
N-{5-[4-(4-methyl piperazine methyl)-benzoylamido]-2-methylphenyl}-4-[3-(4-ethyl)-pyridyl]-2-pyrimidine amine;
N-{5-[4-(4-methyl piperazine methyl)-benzoylamido]-2-methylphenyl}-4-[3-(4-(2-propyl)-pyridyl)]-2-pyrimidine amine;
N-{5-[4-(4-methyl piperazine methyl)-benzoylamido]-2-methylphenyl}-4-[3-(4-methyl)-pyridyl]-2-pyrimidine amine;

N-{5-[4-(4-methyl piperazine methyl)-benzoylamido]-2-methylphenyl}-4-[3-(5-phenyl)-pyridyl]-2-pyrimidine amine;

N-{5-[4-(4-methyl piperazine methyl)-benzoylamido]-2-methylphenyl}-4-[3-(5-(4-pyridinyl)-pyridyl]-2-pyrimidine amine; or N-{5-[4-(4-methyl piperazine methyl)-benzoylamido]-2-methylphenyl}-6-methyl-4-(3-pyridyl)-2-pyrimidine amine.

7. The ligand of claim 1, wherein the ligand is N-{5-[4-(4-methyl piperazine methyl)-benzoylamido]-2-methylphenyl}-4-[3-(4-methyl)-pyridyl]-2-pyrimidine amine.

8. The ligand of claim 1, wherein the ligand is N-{5-[4-(4-methyl piperazine methyl)-benzoylamido]-2-methylphenyl}-4-[3-(4-ethyl)-pyridyl]-2-pyrimidine amine.

9. The ligand of claim 1, wherein the ligand is N-{5-[4-(4-methyl piperazine methyl)-benzoylamido]-2-methylphenyl}-4-[3-(4-(2-propyl)-pyridyl)]-2-pyrimidine amine.

10. The ligand of claim 1, wherein the ligand is N-{5-[4-(4-methyl piperazine methyl)-benzoylamido]-2-methylphenyl}-4-[3-(4-methyl)-pyridyl]-2-pyrimidine amine.

11. The ligand of claim 1, wherein the ligand is N-{5-[4-(4-methyl piperazine methyl)-benzoylamido]-2-methylphenyl}-4-[3-(5-phenyl)-pyridyl]-2-pyrimidine amine.

12. The ligand of claim 1, wherein the ligand is N-{5-[4-(4-methyl piperazine methyl)-benzoylamido]-2-methylphenyl}-4-[3-(5-(4-pyridinyl)-pyridyl]-2-pyrimidine amine.

13. The ligand of claim 1, wherein the ligand is N-{5-[4-(4-methyl piperazine methyl)-benzoylamido]-2-methylphenyl}-6-methyl-4-(3-pyridyl)-2-pyrimidine amine.

14. A lipid formulation comprising the ligand of claim 1.

15. The lipid formulation of claim 14, wherein the lipid formulation comprises one or more cationic lipids.

16. The lipid formulation of claim 15, wherein the one or more cationic lipids are selected from 1,2-dimyristoyl-sn-glycero-3-phosphocholine (DMPC), N,N-dioleyl-N,N-dimethylammonium chloride (DODAC); N-(2,3-d-ioleyloxy) propyl-N,N—N-triethylammonium chloride (DOTMA); N,N-distearyl-N,N-dimethylammonium bromide (DDAB); N-(2,3-dioleoyloxy)propyl)-N,N,N-trimethylammonium chloride (DOTAP); 313-(N—(N',N'-dimethylaminoethane)-carbamoyl)cholesterol (DC-Chol), N-(1-(2,3-dioleyloxy) propyl)-N-2-(sperminecarboxamido)ethyl)-N,N-dimethylammonium trifluoracetate (DOSPA), d-ioctadecylamidoglycyl carboxyspermine (DOGS), 1,2-dileoyl-sn-3-phosphoethanolamine (DOPE), 1,2-dioleoyl-3-dimethylammonium propane (t1DODAP), or N-(1,2-dimyristyloxyprop-3-yl)-N,N-dimethyl-N-hydroxyethyl ammonium bromide (DMRIE).

17. The lipid formulation of claim 15 further comprising cholesterol.

18. A method of treating a gastrointestinal stromal tumor or chronic myeloid leukemia in a subject having said gastrointestinal stromal tumor or chronic myeloid leukemia, the method comprising providing an effective amount of a protein ligand to a subject having gastrointestinal stromal tumor or chronic myeloid leukemia, wherein the protein ligand selectively inhibits a protein kinase, wherein the protein ligand is the ligand of claim 1.

19. The method of claim 18, wherein the subject has a gastrointestinal stromal tumor.

20. The method of claim 19, wherein the subject has chronic myeloid leukemia.

* * * * *